(12) United States Patent
Basile

(10) Patent No.: US 9,616,106 B2
(45) Date of Patent: *Apr. 11, 2017

(54) IL-12 FOR RADIATION PROTECTION AND RADIATION-INDUCED TOXICITY MITIGATION

(71) Applicant: Neumedicines, Inc., Pasadena, CA (US)

(72) Inventor: Lena A. Basile, Tujunga, CA (US)

(73) Assignee: Neumedicines, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/372,738

(22) PCT Filed: Jan. 18, 2013

(86) PCT No.: PCT/US2013/022319
§ 371 (c)(1),
(2) Date: Jul. 16, 2014

(87) PCT Pub. No.: WO2013/154647
PCT Pub. Date: Oct. 17, 2013

(65) Prior Publication Data
US 2014/0369958 A1 Dec. 18, 2014

Related U.S. Application Data

(60) Provisional application No. 61/588,098, filed on Jan. 18, 2012, provisional application No. 61/734,364, filed on Dec. 6, 2012.

(51) Int. Cl.
*A61K 38/20* (2006.01)

(52) U.S. Cl.
CPC .................... *A61K 38/208* (2013.01)

(58) Field of Classification Search
CPC .................................. A61K 38/208
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,485,045 A | 11/1984 | Regen |
| 4,496,689 A | 1/1985 | Mitra |
| 4,544,545 A | 10/1985 | Ryan et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 5,013,556 A | 5/1991 | Woodle et al. |
| 5,573,764 A | 11/1996 | Sykes et al. |
| 5,648,072 A | 7/1997 | Trinchieri et al. |
| 5,648,467 A | 7/1997 | Trinchieri et al. |
| 5,744,132 A * | 4/1998 | Warne ............... A61K 47/26 424/85.2 |
| 5,756,085 A | 5/1998 | Sykes et al. |
| 5,853,714 A | 12/1998 | Deetz et al. |
| 6,683,046 B1 | 1/2004 | Gately et al. |
| 7,052,685 B1 * | 5/2006 | Rook ............... A61K 38/208 424/85.1 |
| 7,939,058 B2 | 5/2011 | Chen et al. |
| 2003/0147849 A1 | 8/2003 | Warne et al. |
| 2005/0136034 A1 * | 6/2005 | Chen ............... A61N 5/10 424/85.2 |
| 2010/0015134 A1 | 1/2010 | Parren et al. |
| 2011/0206635 A1 | 8/2011 | Chen et al. |
| 2012/0010229 A1 | 1/2012 | MacDougall et al. |

FOREIGN PATENT DOCUMENTS

| | | |
|---|---|---|
| WO | WO 2011/005406 | 1/2011 |
| WO | WO-2011/022339 A1 | 2/2011 |
| WO | WO-2011/146574 A1 | 11/2011 |

OTHER PUBLICATIONS

Basile et al., J Transl Med. May 19, 2008;6:26.*
Teicher et al., Int J Cancer. Jan. 3, 1996;65(1):80-84.*
Office Action issued in related U.S. Appl. No. 13/745,698, dated Sep. 22, 2015.
Basile, et al., "HemaMax™, a Recombinant Human Interleukin-12, is a Potent Mitigator of Acute Radiation Injury in Mice and Non-Human Primates," PLOS One, vol. 7, No. 2, 23 pages (2012).
Barda Grants $273m to ramp up Neumedicines HemaMax development, Pharmaceutical Business Review, 2 pages (2011).
P0S23-20. Mitigation of "Radiation Combined Injury" (RCI) by Interleukin-12, 2 pages (2011).
European Communication issued in related European Patent Application No. 13 77 5478, dated Nov. 3, 2015.
"Neumedicines Wins U.S. Federal Government Contract for up to $273 million to Fund Late-Stage Development of HemaMax™, a Novel Radiation Medical Countermeasure," 2 pages (2011).
Ahmed et al., "Cytokine-induced expansion of human $CD34^+$stem/progenitor and $CD34^+CD41^+$ early megakaryocytic marrow cells cultures on normal osteoblasts," Stem Cells, 1999, 17:92-99.
Akimoto et al., "Erythropoietin regulates vascular smooth muscle cell apoptosis by a phosphatidylinositol 3 kinase-dependent pathway," Kidney Int., 2000, 58:269-282.
Anagnostou et al, "Erythropoietin receptor mRNA expression in human endothelial cells," Proc. Natl. Acad. Sci. USA, 1994, 91:3974-3978.
Barker et al., "Identification of stem cells in small intestine and colon by marker gene Lgr5," Nature, Oct. 25, 2007, 449:1003-1008.
Barker et al., "Lgr5($^{+ve}$) stem cells drive self-renewal in the stomach and build long-lived gastric units in vitro," Cell Stem Cell., Jan. 8, 2010, 6:25-36.
Basile et al., "Multilineage hematopoietic recovery with concomitant antitumor effects using low dose Interleukin-12 in myelosuppressed tumor-bearing mice," J. Transl. Med., May 19, 2008, 6:26, 27 pages.
Bekaii-Saab et al., "A phase I trial of paclitaxel and trastuzumab in combination with interleukin-12 in patients with HER2/neu-expressing malignancies," Mol. Cancer Ther., Nov. 2009, 8(11):2983-2991.
Bellone et al., "Dual stimulatory and inhibitory effect of NK cell stimulatory factor/IL-12 on human hematopoiesis," J. Immunol., 1994, 153:930-937.
Brines et al., "Emerging biological roles for erythropoietin in the nervous system," Nat. Rev. Neurosci., Jun. 2005, 6:484-494.

(Continued)

Primary Examiner — Daniel C Gamett
(74) Attorney, Agent, or Firm — Foley & Lardner LLP

(57) ABSTRACT

Aspects and embodiments of the instant disclosure provide therapeutic methods and compositions comprising interleukin 12 (IL-12) useful for treating radiation-induced damage in a subject. In particular, the instant disclosure provides methods and compositions for radiation protection and/or radiation toxicity mitigation for the treatment of acute radiation syndrome and radiation induced toxicity associated with the treatment of cutaneous T-cell lymphoma.

20 Claims, 43 Drawing Sheets

(56) References Cited

OTHER PUBLICATIONS

Broxmeyer et al., "Comparative analysis of the influences of human gamma, alpha and beta interferons on human multipotential (CFU-GEMM, erythroid (BFU-E) and granulocyte-macrophage (CFU-GM) progenitor cells," *J. Immunol.*, Sep. 1983, 131(3):1300-1305.
Buemi et al., "The pleiotropic effects of erythropoietin in the central nervous system," *J. Neuropathol. Exp. Neurol.*, Mar. 2003, 62(3):228-236.
Burdelya et al., "An agonist of toll-like receptor 5 has radioprotective activity in mouse and primate models," *Science*, Apr. 11, 2008, 320:226-230.
Cetin et al., "Novel evidence suggesting an anti-oxidant property for erythropoietin on vancomycin-induced nephrotoxicity in a rat model," *Clin. Exp. Pharmacol. Physiol.*, 2007, 34:1181-1185.
Chao, "Accidental or intentional exposure to ionizing radiation: biodosimetry and treatment options," *Exp. Hematol.*, 2007, 35:24-27.
Chen et al., "Growth hormone mitigates against lethal irradiation and enhances hematologic and immune recovery in mice and nonhuman primates," *PLoS One*, Jun. 2010, 5(6):e11056, 12 pages.
Chen et al., "IL-12 facilitates both the recovery of endogenous hematopoiesis and the engraftment of stem cells after ionizing radiation," *Exp. Hematol.*, 2007, 35:203-213.
Chong et al., "Erythropoietin is a novel vascular protectant through activation of Akt1 and mitochondrial modulation of cysteine proteases," *Circulation*, Dec. 3, 2002, 106:2973-2979.
Chong et al., "Hematopoietic factor erythropoietin fosters neuroprotection through novel signal transduction cascades," *J. Cereb. Blood Flow Metab.*, 2002. 22(5):503-514.
Colombo et al., "Interleukin-12 in anti-tumor immunity and immunotherapy," *Cytokine Growth Factor Rev.*, 2002, 13:155-168.
de Barros et al., "Osteoblasts and bone marrow mesenchymal stromal cells control hematopoietic stem cell migration and proliferation in 3D in vitro model," *PLoS One*, Feb. 2010, 5(2):e9093, 13 pages.
Dinarello et al., "Interleukin-18 and host defense against infection," *J. Infect. Dis.*, 2003, 187(Suppl 2):S370-S384.
Dominici et al., "Restoration and reversible expansion of the osteoblastic hematopoietic stem cell niche after marrow radioablation," *Blood*, Sep. 10, 2009, 114(11):2333-2343.
Donnelly et al., "Acute radiation syndrome: assessment and management," *South. Med. J.*, Jun. 2010, 103(6):541-544.
Drouet et al., "Radiation victim management and the haematologist in the future: time to revisit therapeutic guidelines?" *Int. J. Radiat. Biol.*, Aug. 2010, 86(8):636-648.
Dumont et al., "Radiation countermeasure agents: an update," *Expert Opin. Ther. Pat.*, 2010, 20(1):73-101.
Fraser et al., "Expression of specific high-affinity binding sites for erythropoietin on rat and mouse megakaryocytes," *Exp. Hematol.*, Jan. 1989, 17(1):10-16 (abstract only).
Fuchs et al., "Neopterin as a marker for activated cell-mediated immunity: application in HIV infection," *Immunol. Today*, 1988, 9(5):150-155.
Garcia et al., "LGR5 deficiency deregulates Wnt signaling and leads to precocious Paneth cell differentiation in the fetal intestine," *Dev. Biol.*, 2009, 331:58-67.
Gattoni et al., Interferon-gamma: biologic functions and HCV therapy (type I/II) (1 of 2 parts), *Clin. Ter.*, Jul.-Aug. 2006, 157(4):377-386 (abstract only).
Genc et al., "Erythropoietin restores glutathione peroxidase activity in 1-methyl-4-phenyl-1,2,5,6-tetrahydropyridine-induced neurotoxicity in C57BL mice and stimulates murine astroglial glutathione peroxidase production in vitro," *Neurosci. Lett.*, 2002, 321:73-76.
Gerosa et al., "Reciprocal activating interaction between natural killer cells and dendritic cells," *J. Exp. Med.*, 2002, 195(3):327-333.
Gimble et al., "Modulation of lymphohematopoiesis in long-term cultures by gamma interferon: direct and indirect action on lymphoid and stromal cells," *Exp. Hematol.*, Feb. 1993, 21(2):224-230 (abstract only).
Gracie et al., "Interleukin-18," *J. Leukoc. Biol.*, Feb. 2003, 73:213-224.
Hamada et al., "Transendothelial migration of megakaryocytes in response to stromal cell-derived factor 1 (SDF-1) enhances platelet formation," *J. Exp. Med.*, Aug. 3, 1998, 188(3):539-548.
Hérodin et al., "Cytokine-based treatment of accidentally irradiated victims and new approaches," *Exp. Hematol.*, 2005, 33:1071-1080.
Hirayama et al., "Synergistic interaction between interleukin-12 and steel factor in support of proliferation of murine lymphohematopoietic progenitors in culture," *Blood*, Jan. 1, 1994, 83(1):92-98.
Hodohara et al., "Stromal cell-derived factor-1 (SDF-1) acts together with thrombopoietin to enhance the development of megakaryocytic progenitor cells (CFU-MK)," *Blood*, Feb. 1, 2000, 95(3):769-775.
Jacobsen et al., "Cytotoxic lymphocyte maturation factor (interleukin 12) is a synergistic growth factor for hematopoietic stem cells," *J. Exp. Med.*, Aug. 1993, 178:413-418.
Jaquet et al., "Erythropoietin and VEGF exhibit equal angiogenic potential," *Microvasc. Res.*, 2002, 64:326-333.
Johnson et al., "Mitigation of hematologic radiation toxicity in mice through pharmacological quiescence induced by CDK4/6 inhibition," *J. Clin. Invest.*, Jul. 2010, 120(7):2528-2536.
Kiel et al., "Maintaining hematopoietic stem cells in the vascular niche," *Immunity*, Dec. 2006, 25:862-864.
Kumral et al., "Erythropoietin increases glutathione peroxidase enzyme activity and decreases lipid peroxidation levels in hypoxic-ischemic brain injury in neonatal rats," *Biol. Neonate*, 2005, 87:15-18.
Kurz et al., "Interferon-γ-mediated pathways are induced in human CD34$^+$haematopoietic stem cells," *Immunobiology*, 2010, 215:452-457.
Lacy et al., "Phase II study of interleukin-12 for treatment of plateau phase multiple myeloma (E1A96): a trial of the Eastern Cooperative Oncology Group," *Leuk. Res.*, 2009, 33:1485-1489.
Langrish et al., "IL-12 and IL-23: master regulators of innate and adaptive immunity," *Immunol. Rev.*, 2004, 202:96-105.
Lenzi et al., "Phase I study of intraperitoneal recombinant human interleukin 12 in patients with Müllerian carcinoma, gastrointestinal primary malignancies, and mesothelioma," *Clin. Cancer Res.*, Dec. 2002, 8:3686-3695.
Lenzi et al., "Phase II study of intraperitoneal recombinant interleukin-12 (rhIL-12) in patients with peritoneal carcinomatosis (residual disease <1 cm) associated with ovarian cancer or primary peritoneal carcinoma," *J. Transl. Med.*, 2007 5:66, 5 pages.
Leonard et al., "Effects of single-dose interleukin-12 exposure on interleukin-12-associated toxicity and interferon-γ production," *Blood*, Oct. 1, 1997, 90(7):2541-2548.
Lifshitz et al., "Non-erythroid activities of erythropoietin: Functional effects of murine dendritic cells," *Mol. Immunol.*, 2009, 46:713-721.
Little et al., "Phase 2 study of pegylated liposomal doxorubicin in combination with interleukin-12 for AIDS-related Kaposi sarcoma," *Blood*, Dec. 15, 2007, 110(13):4165-4171.
Liu et al., "Epo protects SOD2-deficient mouse astrocytes from damage by oxidative stress, " *GLIA*, 2006, 53:360-365.
Lodoen et al., "Natural killer cells as an initial defense against pathogens," *Curr. Opin. Immunol.*, 2006, 18:391-398.
MacDougall et al., "Erythropoietin resistance: the role of inflammation and pro-inflammatory cytokines," *Nephrol. Dial. Transplant*, 2002, 17(Suppl 11):39-43.
Means et al., "Inhibition of human erythroid colony-forming units by γ interferon can be corrected by recombinant human erythropoietin," *Blood*, Nov. 15, 1991, 78(10):2564-2567.
Melichar et al., "Intraperitoneal fluid neopterin, nitrate, and tryptophan after regional administration of interleukin-12," *J. Immunother.*, 2003, 26(3):270-276.
Morceau et al., "Pro-inflammatory cytokine-mediated anemia: regarding molecular mechanisms of erythropoiesis," *Mediators Inflamm.*, 2009, 2009:405016, 11 pages.
Nakanishi et al., "Interleukin-18 is a unique cytokine that stimulates both Th1 and Th2 responses depending on its cytokine milieu," *Cytokine Growth Factor Rev.*, 2001, 12:53-72.

(56) References Cited

OTHER PUBLICATIONS

Neta et al., "IL-12 protects bone marrow from and sensitizes intestinal tract to ionizing radiation," *J. Immunol.*, 1994, 153:4230-4237.

Parsa et al., "A novel protective effect of erythropoietin in the infarcted heart," *J. Clin. Invest.*, Oct. 2003, 112(7):999-1007.

Ploemacher et al., "Interleukin-12 enhances interleukin-3 dependent multilineage hematopoietic colony formation stimulated by interleukin-11 or steel factor," *Leukemia*, Sep. 1993, 7(9):1374-1380 (abstract only).

Ploemacher et al., "Interleukin-12 synergizes with interleukin-3 and steel factor to enhance recovery of murine hemopoietic stem cells in liquid culture," *Leukemia*, Sep. 1993, 7(9):1381-1388 (abstract only).

Prutchi Sagiv et al., "Erythropoietin effects on dendritic cells: potential mediators in its function as an immunomodulator?" *Exp. Hematol.*, 2008, 36:1682-1690.

Savino et al., "A paradigm shift for erythropoietin: no longer a specialized growth factor, but rather an all-purpose tissue-protective agent," *Cell Death Differ.*, 2004, 11(Suppl 1): S2-S4.

Sela et al., "The polymorphonuclear leukocyte—a new target for erythropoietin," *Nephron*, 2001, 88:205-210.

Singh et al., "Role of cytokines and growth factors in radioprotection," *Exp. Mol. Pathol.*, 2005, 78:156-169.

Stonier et al., "Trans-presentation: a novel mechanism regulating IL-15 delivery and responses," *Immunol. Lett.*, Jan. 4, 2010, 127(2):85-92 (author manuscript, 16 pages).

Terrell et al., "Comparative pathology of recombinant murine interferon-gamma in mice and recombinant human interferon-gamma in cynomolgus monkeys," *Int. Rev. Exp. Pathol.*, 1993, 34(Pt. B):73-101 (abstract only).

Trinchieri, "Interleukin-12: a cytokine at the interface of inflammation and immunity," *Adv. Immunol.*, 1998, 70:83-243.

U.S. Department of Health and Human Services, Food and Drug Administration, Center for Drug Evaluation and Research (CDER), "Guidance for Industry—estimating the maximum safe starting dose in initial clinical trials for therapeutics in adult healthy volunteers," http://www.fda.gov/downloads/Drugs/GuidanceComplianceRegulatoryInformation/Guidances/ucm078932.pdf., 2005, Accessed Jun. 13, 2011, 30 pages.

Varma et al., "Endotoxin-induced gamma interferon production: contributing cell types and key regulatory factors," *Clin. Diagn. Lab. Immunol.*, May 2002, 9(3):530-543.

Vijay-Kumar et al., "Flagellin treatment protects against chemicals, bacteria, viruses, and radiation," *J. Immunol.*, 2008, 180:8280-8285.

Wang et al., "The α-chemokine receptor CXCR4 is expressed on the megakaryocytic lineage from progenitor to platelets and modulates migration and adhesion," *Blood*, Aug. 1, 1998, 92(3):756-764.

Wang et al., "Erythropoietin protects retinal pigment epithelial cells from oxidative damage," *Free Radic. Biol. Med.*, 2009, 46:1032-1041.

Weiss et al., "History and development of radiation-protective agents," *Int. J. Radiat Biol.*, Jul. 2009, 85(7):539-573.

Werner et al., "Tetrahydrobiopterin biosynthetic activities in human macrophages, fibroblasts, THP-1, and T 24 cells," *J. Biol. Chem.*, Feb. 25, 1990, 265(6):3189-3192.

Williams et al., "Animal models for medical countermeasures to radiation exposure," *Radiat Res.*, Apr. 2010, 173(4):557-578 (author manuscript, 35 pages).

Yuan et al., "Erythropoietin: a potent inducer of peripheral immuno/inflammatory modulation in autoimmune EAE," *PLoS One*, Apr. 2008, 3(4):e1924, 11 pages.

Zhang et al., "Factors determining the formation and release of bioactive IL-12: regulatory mechanisms for IL-12p70 synthesis and inhibition," *Biochem. Biophys. Res. Commun.*, 2008, 372:509-512.

Zhao et al., "Brief report: interferon-γ induces expansion of Lin Sca-1$^+$C-Kit$^+$Cells," *Stem Cells*, 2010, 28:122-126.

Zou et al., "Structure-function analysis of the p35 subunit of mouse interleukin 12," *J. Biol. Chem.*, Mar. 17, 1995, 270(11):5864-5871.

Zoumbos et al., "Interferon is the suppressor of hematopoiesis generated by stimulated lymphocytes in vitro," *J. Immunol.*, Aug. 1984, 133(2):769-774.

www.atomicarchive.com, "Effects of radiation levels on human body," http://www.atomicarchive.com/Effects/radeffectstable.shtml, Accessed Jun. 19, 2011, 2 pages.

International Search Report and Written Opinion dated Oct. 16, 2013, from corresponding International Patent Application No. PCT/US13/22319, 18 pages.

Office Action issued in related U.S. Appl. No. 13/745,698, dated May 23, 2016.

Proceedings, the Japan Radiation Research Society, annual meeting, vol. 47, p. 99, No. P1-34 (2004).

Notice of Reasons for Rejection issued in related Japanese Patent Application No. 2014-553494, dated Jun. 6, 2016.

\* cited by examiner

Figure 5 (continued)
(f) Irradiation +
m-HemaMax at 24 hours
and 4 days
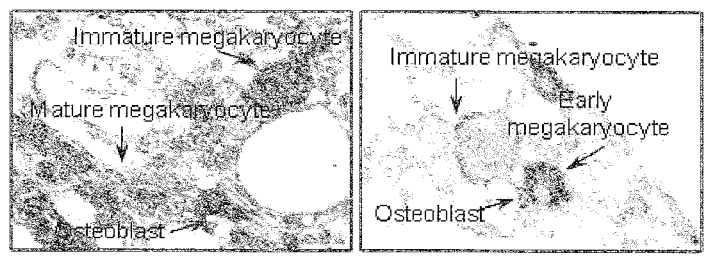
(g) Irradiation +
HemaMax at 24 hours
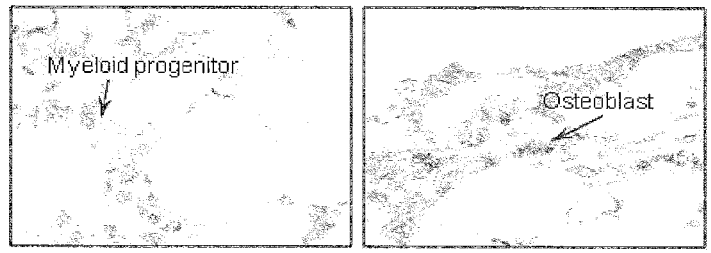

FIGURE 6
(a)
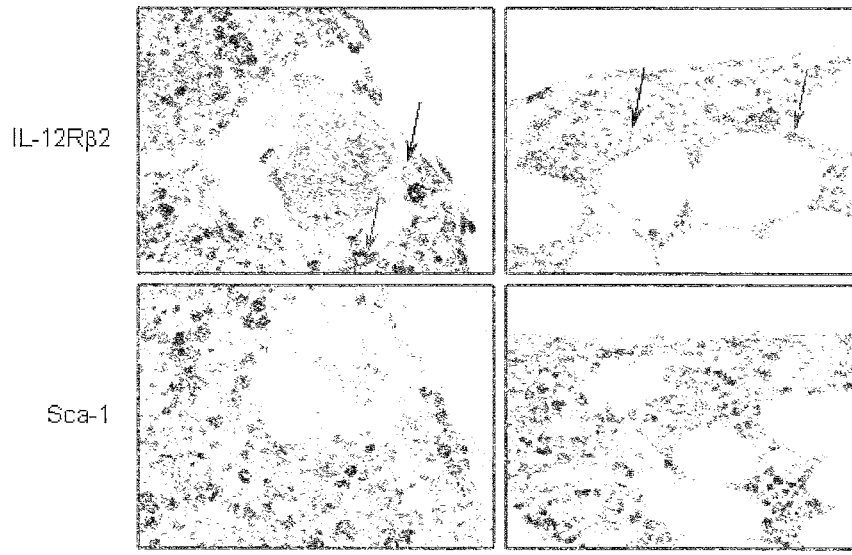
(b)
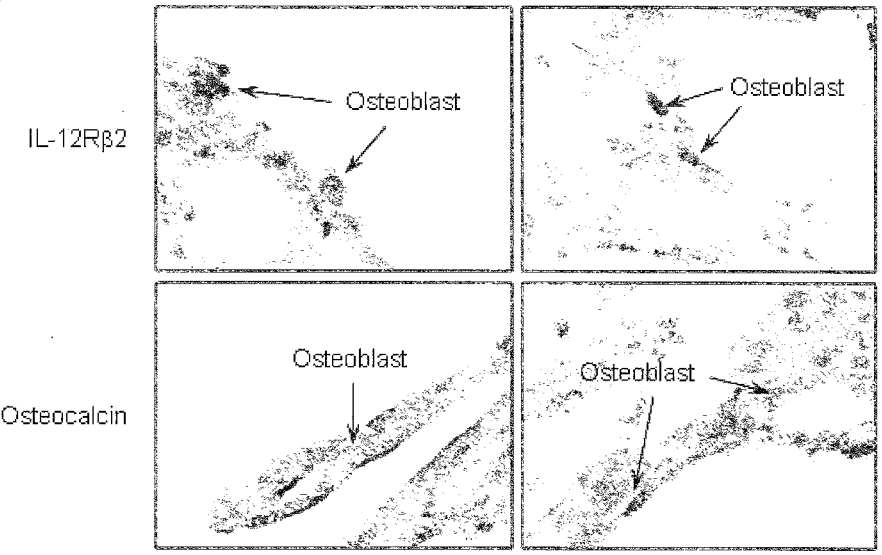
(c)

(a) Bone marrow (a) Small Intestine

~3.5-fold Increase in Survivors After Exposure to Radiation (LD90)

HemaMax Treatment Is Associated with Decreased Hemorrhage Scores in Deceased Irradiated NHP (LD90/60)

FIGURE 17
HemaMax Stimulates BM Regeneration Following Lethal Radiation Exposure
NHP, post-irradiation (LD90), day 12 bone marrow biopsies
Regenerating island          Megakaryocytes
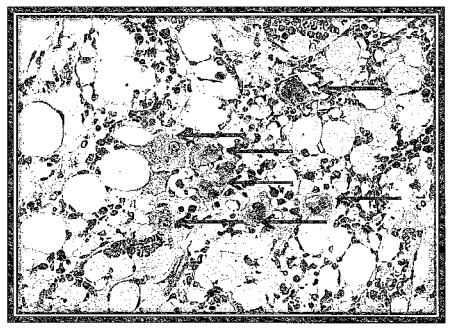

FIGURES 18A-18G

Irradiated Rhesus Monkey Bone Marrow

NHP, post-irradiation (LD90), day 12 bone marrow biopsies

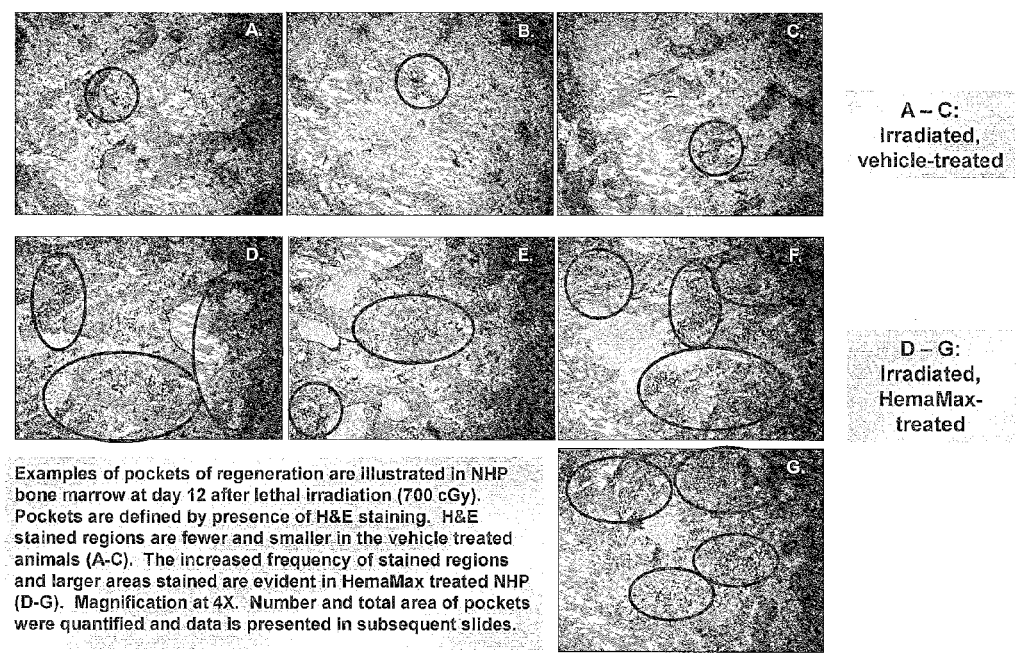

A – C: Irradiated, vehicle-treated

D – G: Irradiated, HemaMax-treated

Examples of pockets of regeneration are illustrated in NHP bone marrow at day 12 after lethal irradiation (700 cGy). Pockets are defined by presence of H&E staining. H&E stained regions are fewer and smaller in the vehicle treated animals (A-C). The increased frequency of stained regions and larger areas stained are evident in HemaMax treated NHP (D-G). Magnification at 4X. Number and total area of pockets were quantified and data is presented in subsequent slides.

HemaMax Treatment is Associated with Decreased Incidence of
Sepsis in Irradiated NHP Determined by positive blood cultures
In 6 animals w/o blood cultures (early death) ≥5 organs with >2 grade infection were Plasma Concentration-Time Profiles of HemaMax After a SC Dose in Non-Irradiated and Irradiated Monkeys ➢ Slightly prolonged distribution phase in irradiated animals (after SC dosing)?

Plasma Concentration-Time Profiles of HemaMax After an IV Dose (250 ng/kg) in Non-Irradiated and Irradiated Monkeys Log Scale ➢ There appeared to be a small increase in HemaMax half-life in irradiated animals.

Plasma Concentration-Time Profiles of HemaMax After an IV Dose
(250 ng/kg) in Non-Irradiated and Irradiated Monkeys Linear Scale ➢ PK profiles were very similar between groups on a linear scale.

FIGURE 31
Pharmacodynamics
IFN-γ
IFN-γ PD After a SC Dose of 0, 50, 100, 250 or 500 ng/kg, and a 250 ng/kg IV Dose of HemaMax in Non-Irradiated Animals
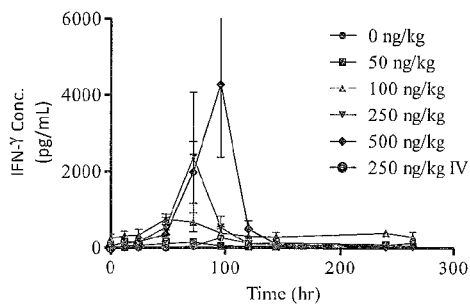
IFN-γ Response After HemaMax SC Dosing
➤ The $T_{max}$ of plasma IFN-γ occurred earlier after irradiation.
➤ The IFN-γ response increased with increasing dose.
IFN-γ PD After a SC Dose of 0, 50, 100, 250 or 500 ng/kg, and a 250 ng/kg IV Dose of HemaMax in Irradiated Animals
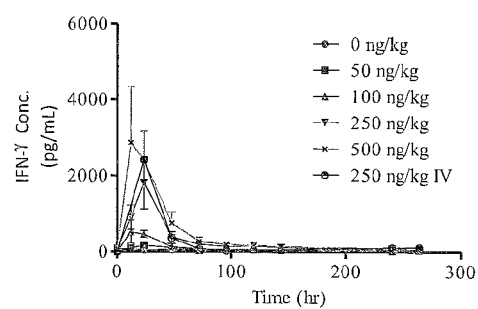

Pharmacodynamics of IFN-γ After an IV Dose of HemaMax in Non-Irradiated and Irradiated Monkeys ➢ The IFN-γ response was more pronounced after irradiation.

FIGURE 33

Pharmacodynamics

EPO

EPO PD After a SC Dose of 0, 50, 100, 250 or 500 ng/kg, and a 250 ng/kg IV Dose of HemaMax in Non-Irradiated Animals

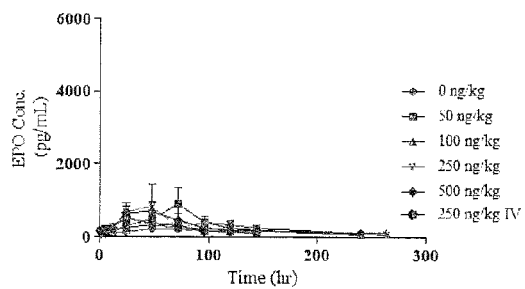

Pharmacodynamics of EPO After a SC Dose of HemaMax in Non-Irradiated and Irradiated Monkeys.

EPO PD After a SC Dose of 0, 50, 100, 250 or 500 ng/kg, and a 250 ng/kg IV Dose of HemaMax in Irradiated Animals

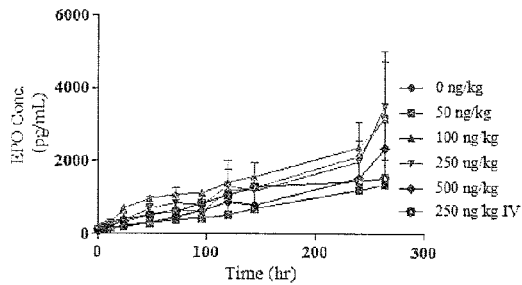

➢ Over the time frame studied (in irradiated animals), the EPO response continued to rise with time.

➢ The dose response in EPO concentrations was not strong.

Pharmacodynamics of EPO After an IV Dose of HemaMax in Non-Irradiated and Irradiated Monkeys > In irradiated animals, the EPO response continued to rise over time, similar to SC dosing.

IL18

Pharmacodynamics of IL-18 After a SC Dose of HemaMax in Non-Irradiated and Irradiated Monkeys ➢ The increase in IL-18 appeared to be more pronounced in irradiated animals.

➢ The IL-18 response increased with increasing dose in irradiated animals.

Pharmacodynamics of IL-18 After an IV Dose of HemaMax in Non-Irradiated and Irradiated Monkeys

➢ The increase in IL-18 appeared to be more pronounced in irradiated animals (similar to SC dosing).

Pharmacodynamics of IL-15 After a SC Dose of HemaMax in
Non-Irradiated and Irradiated Monkeys > The increase in IL-15 appeared to be more pronounced in irradiated animals.

> IL-15 concentrations generally increased with increasing dose.

Pharmacodynamics of IL-15 After an IV Dose of HemaMax in Non-Irradiated and Irradiated Monkeys ➢ The increase in IL-15 appeared to be more pronounced in irradiated animals.

SEQUENCE LISTING

<160> NUMBER OF SEQ ID NOS: 4

<210> SEQ ID NO 1
<211> LENGTH: 197
<212> TYPE: PRT
<213> ORGANISM: Homo Sapien

<400> SEQUENCE: 1

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 2
<211> LENGTH: 306
<212> TYPE: PRT
<213> ORGANISM: Homo Sapien

<400> SEQUENCE: 2

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
```

```
                115                 120                 125
Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
290                 295                 300

Cys Ser
305

<210> SEQ ID NO 3
<211> LENGTH: 194
<212> TYPE: PRT
<213> ORGANISM: Mouse

<400> SEQUENCE: 3

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
                35                  40                  45

Thr Arg Asp Gln Thr Ser Thr Leu Lys Thr Cys Leu Pro Leu Glu Leu
                50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
                100                 105                 110

Gln Ala Ile Asn Ala Ala Leu Gln Asn His Asn His Gln Ile Ile
                115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175
```

```
Ser Thr Arg Val Val Thr Ile Asn Arg Val Met Gly Tyr Leu Ser Ser
            180                 185                 190

Ala Met
```

<210> SEQ ID NO 4
<211> LENGTH: 312
<212> TYPE: PRT
<213> ORGANISM: mouse

<400> SEQUENCE: 4

```
Trp Glu Leu Glu Lys Asp Val Tyr Val Val Glu Val Asp Trp Thr Pro
1               5                   10                  15

Asp Ala Pro Gly Glu Thr Val Asn Leu Thr Cys Asp Thr Pro Glu Glu
            20                  25                  30

Asp Asp Ile Thr Trp Thr Ser Asp Gln Arg His Gly Val Ile Gly Ser
        35                  40                  45

Gly Lys Thr Leu Thr Ile Thr Val Lys Glu Phe Leu Asp Ala Gly Gln
    50                  55                  60

Tyr Thr Cys His Lys Gly Gly Glu Thr Leu Ser His Ser His Leu Leu
65                  70                  75                  80

Leu His Lys Lys Glu Asn Gly Ile Trp Ser Thr Glu Ile Leu Lys Asn
                85                  90                  95

Phe Lys Asn Lys Thr Phe Leu Lys Cys Glu Ala Pro Asn Tyr Ser Gly
            100                 105                 110

Arg Phe Thr Cys Ser Trp Leu Val Gln Arg Asn Met Asp Leu Lys Phe
        115                 120                 125

Asn Ile Lys Ser Ser Ser Ser Ser Pro Asp Ser Arg Ala Val Thr Cys
130                 135                 140

Gly Met Ala Ser Leu Ser Ala Glu Lys Val Thr Leu Asp Gln Arg Asp
145                 150                 155                 160

Tyr Glu Lys Tyr Ser Val Ser Cys Gln Glu Asp Val Thr Cys Pro Thr
                165                 170                 175

Ala Glu Glu Thr Leu Pro Ile Glu Leu Ala Leu Glu Ala Arg Gln Gln
            180                 185                 190

Asn Lys Tyr Glu Asn Tyr Ser Thr Ser Phe Phe Ile Arg Asp Ile Ile
        195                 200                 205

Lys Pro Asp Pro Pro Lys Asn Leu Gln Met Lys Pro Leu Lys Asn Ser
    210                 215                 220

Gln Val Glu Val Ser Trp Glu Tyr Pro Asp Ser Trp Ser Thr Pro His
225                 230                 235                 240

Ser Tyr Phe Ser Leu Lys Phe Phe Val Arg Ile Gln Arg Lys Lys Glu
                245                 250                 255

Lys Met Lys Glu Thr Glu Glu Gly Cys Asn Gln Lys Gly Ala Phe Leu
            260                 265                 270

Val Glu Lys Thr Ser Thr Glu Val Gln Cys Lys Gly Gly Asn Val Cys
        275                 280                 285

Val Gln Ala Gln Asp Arg Tyr Tyr Asn Ser Ser Cys Ser Lys Trp Ala
    290                 295                 300

Cys Val Pro Cys Arg Val Arg Ser
305                 310
```

IL-12 FOR RADIATION PROTECTION AND RADIATION-INDUCED TOXICITY MITIGATION

This application is a National Phase of International Patent Application No. PCT/US2013/022319, filed Jan. 18, 2013, which claims priority to U.S. Provisional Patent Application No. 61/588,098, filed Jan. 18, 2012, and U.S. Provisional Patent Application No. 61/734,364, filed Dec. 6, 2012. These applications are incorporated herein by reference in their entirety, including all figures and tables.

SEQUENCE LISTING

The present application contains a Sequence Listing which has been submitted electronically in ASCII format and is hereby incorporated by reference in its entirety.

FIELD

The present disclosure relates generally to novel methods and compositions for radiation protection and/or radiation-induced toxicity mitigation. In particular, the disclosure provides methods and compositions for radiation protection and/or radiation toxicity mitigation for the treatment of acute radiation syndrome and radiation induced toxicity associated with the treatment of cutaneous T-cell lymphoma.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

Humans and animals are highly susceptible to radiation-induced damage resulting in cellular, tissue, organ and systemic injuries. In accidental radiation exposure, such as a nuclear explosion or a disaster scenario, many victims will suffer from acute radiation syndrome (ARS) to varying degrees. The immediate objectives at a radiation disaster scene are quite different from the radiation treatment of cancer. In such a disaster scenario, early efforts would involve reaching as many afflicted individuals as possible with a treatment that could prolong life, so that victims could be successfully triaged and receive subsequent, in-depth medical care as dictated by their individual condition and afflictions. Another aspect of such an accidental, or intentional, radiation disaster is that any life-saving drugs or treatments would have to be active at protracted time points following the radiation disaster. This requirement is due to the time it would take to mobilize medical staff, drugs/treatments, and equipment to a disaster scene, so that life-saving drugs/treatments could be administered to victims in need.

In addition, radiation-induced damage to cells, tissues, organs and systems can be the result of radiation exposure in the course of a treatment for a disease, such as cancer, or incidental radiation exposure due to a disaster involving release or radiation, such as a nuclear explosion. Over 40% of cancer patients will require radiation therapy during management of their disease. Although radiation therapy improves the survival of a significant number of cancer patients, both acute radiation toxicity (that which manifests during a course of clinical radiotherapy or shortly thereafter), and late toxicity (developing months to years after completion of radiotherapy) compromise overall outcomes for successfully treated cancer patients.

For example, cutaneous T-cell lymphoma (CTCL) accounts for about 4% of all cases of non-Hodgkin lymphoma and is generally characterized in part by malignant proliferation of skin-homing T-helper cells within the outer layer of the epidermis and dermis. The most common subgroup of CTCL is mycosis fungoides (MF). The precise etiology of CTCL is unknown, but genetic, infective and environmental causes have been suggested. The incidence of CTCL increases with age, with an average onset between 50 and 60 years. CTCL is twice as common in men as in women. Although this disease is less prevalent in children, people of all ages can be affected. The initial course of patients with CTCL is usually followed by a progression from limited patches to more generalized patches, plaques, tumors and finally, nodal or visceral involvement. Patients with CTCL are classified according to clinical staging system based on the extent of skin involvement (T-stage), presence of lymph node and visceral involvement (TNM-classification system). The two most common subtypes of CTCL are mycosis fungoides which is often indolent (slow-growing) in early stages, and a more aggressive form called "Sézary syndrome". Other less common CTCL subtypes include cutaneous CD30 expressing anaplastic large cell lymphoma, panniculitis-like T-cell lymphoma, aggressive CD8 expressing epidermotropic T-cell lymphoma and gamma-delta T-cell lymphoma. Traditional treatment of patients with CTCL may include both topical and systemic therapies. The most common therapies include psoralene plus UVA irradiation (PUVA), total skin electron beam therapy (TSEBT) and topical and systemic chemotherapy.

TSEBT has been used in treatment of CTCL since the 1950's. Total skin electron beam therapy (TSEBT) or partial skin electron beam therapy (PSEBT) is an effective treatment for cutaneous T-cell lymphoma (CTCL) and mycosis fungoides (MF). Conventional total skin electron irradiation (TSEI) for mycosis fungoides (MF) causes radiation toxicity, requiring treatment interruptions that prolong the treatment period, making patient compliance poor. Prolonged overall treatment time can spare tumor cells and lower the chance of a cure, whereas delivering the total radiation dose over a shorter period provides greater radiobiological benefit and gives better tumor control. Conventionally, TSEI is administered on a daily basis (5 days per week), which invariably results in severe radiation-associated toxicity, requiring treatment interruptions and prolonging the total treatment duration. This may reduce the radiobiological efficiency, affecting the final outcome of the treatment and disease-free Currently, there are agents that can protect cells and tissues from radiation treatments used in cancer, but none have proven to be very effective. In terms of accidental or intentional radiation exposure, there are no known agents that can significantly prolong life when administered at protracted times after radiation exposure to date.

SUMMARY OF THE INVENTION

Accordingly, there is an unmet need for methods, agents and/or compositions that could protect from, or mitigate, radiation-induced damage to cells, tissues, organs and systems, thereby increasing the chance of recovery and restoration of health following acute or chronic radiation exposure. The present disclosure provides methods and therapeutic agents that can increase protection or mitigate of the effects of exposure to ionizing radiation that are useful for increasing the survival and restoration of normal cellular, tissue, organ and system functions following accidental exposure to ionizing radiation or in a radiation therapy setting.

In one aspect, a method of protecting a subject from system, organ, tissue, or cellular damage, following exposure of the subject to ionizing radiation comprising: administering a dose of therapeutically effective amount of a pharmaceutical composition comprising substantially isolated IL-12 to the subject following radiation exposure whereby system, organ or tissue, and/or cellular damage due to radiation is diminished, is provided.

In one aspect, the radiation is received as an acute lethal or near lethal dose sufficient to generate a characteristic associated with acute radiation damage. In another aspect, the radiation damage to the subject is chronic or systemic damage.

In one aspect, the radiation exposure results in a total body irradiation. In one embodiment, the radiation dose is between about 0.7 Gy and about 50 Gy, and as described herein, depending on the quality factor of the ionizing radiation source.

In one embodiment, the systems, organs or tissues protected are selected from the group consisting of: bone marrow, lymphatic system, immune system, mucosal tissue, mucosal immune system, gastrointestinal system, cardiovascular system, nervous system, reproductive organs, prostate, ovaries, lung, kidney, skin and brain.

In one embodiment, the effective dose of IL-12 is less than 300 ng/kg. In one embodiment the effective dose of IL-12 is given in two or more doses of less than 50 ng/kg for each dose. In one embodiment, the one or more effective dose(s) of IL-12 is less than 200 ng/kg. In one embodiment, the one or more effective dose(s) of IL-12 is less than 100 ng/kg. In one embodiment, the effective dose of IL-12 is given in two or more doses of less than 30 ng/kg for each dose.

In one embodiment, the one or more effective dose(s) of IL-12 are given before radiation exposure. In one embodiment, the one or more effective dose(s) of IL-12 are given before and after radiation exposure. In one embodiment, the one or more effective dose(s) of IL-12 are given after radiation exposure. In one embodiment, the one or more effective dose(s) of IL-12 is given at greater than 24 hours after radiation exposure. In one embodiment, the one or more effective dose(s) of IL-12 is given at greater than 48 hours after radiation exposure. In one embodiment, the one or more effective dose(s) of IL-12 is given at greater than 72 hours after radiation exposure. In one embodiment, the one or more effective dose(s) of IL-12 is given at greater than 96 hours after radiation exposure. In one embodiment, the one or more effective dose(s) of IL-12 is given at greater than 120 hours after radiation exposure.

In one embodiment, the administered IL-12 protects dermal tissue from radiation damage. In one embodiment, the administered IL-12 induces the production of erythropoietin. In one embodiment, the erythropoietin production enhanced protection of system, organ, tissue or cellular damage.

In one embodiment, the systems, organs or tissues protected comprise the kidney and lung. In one embodiment, the systems, organs or tissues protected comprise the brain and the cardiovascular system.

In one aspect, the effective dose of IL-12 protects more than one system, organ and/or tissue from radiation damage. In one embodiment, the systems, organs or tissues protected are selected from the group consisting of: bone marrow, gastrointestinal systems, lymphatic system, immune system and/or tissues, mucosal tissue, mucosal immune system, gastrointestinal system, cardiovascular system, nervous system, reproductive organs, prostate, ovaries, lung, kidney, skin, nails, sweat glands and brain.

In another aspect, the radiation is received during the treatment of disease and/or disorder associated with CTCL while the subject is receiving radiation therapy. In one embodiment, the disease and/or disorder associated with CTCL is Mycosis Fungoides. In another embodiment, the disease and/or disorder associated with CTCL is Sézary Syndrome. In one embodiment, the radiation exposure is associated with the treatment of CTCL using electron beam therapy.

In one-embodiment, the one or more effective doses of IL-12 are administered subcutaneously. In one embodiment, the one or more effective doses of IL-12 are administered intravenously. In one embodiment, the one or more effective doses of IL-12 are administered topically. In one embodiment, the IL-12 is administered near the site of susceptible organ damage. In one embodiment, the subject is receiving radiation treatment for CTCL and the IL-12 is administered at or near the site of irradiation.

In one aspect, the radiation is received as a fractionated dose in two or more fractions. In another embodiment, the radiation is received as a fractionated dose in a hyperfractionation therapy. In another aspect, the radiation is received as a fractionated dose in an accelerated fractionation therapy.

In one aspect, the effective dose of IL-12 is given in one or more doses of less than 30 ng/kg for each dose. In another aspect, the effective dose of IL-12 is given in one or more doses of less than 50 ng/kg for each dose. In another aspect, the one or more effective dose(s) of IL-12 is less than 100 ng/kg. In other aspects, the one or more effective dose(s) of IL-12 is/are less than 200 ng/kg. In one aspect, the effective dose of IL-12 is less than 300 ng/kg.

In one aspect, the one or more effective dose(s) of IL-12 are given before radiation exposure. In other aspects, the one or more effective dose(s) of IL-12 are given before and after radiation exposure. In another aspect, the one or more effective dose(s) of IL-12 are given after radiation exposure.

In certain aspects, the one or more effective dose(s) of IL-12 is given at greater than about 24, about 48, about 72, about 96 or about 120 hours after radiation exposure In one aspect, the one or more effective doses of IL-12 are administered topically, subcutaneously, intradermally, intravenously, intraperitoneally, intramuscularly, epidurally, parenterally, intranasally, and/or intracranially. In one embodiment, the IL-12 is administered intradermally. In another embodiment, the IL-12 is administered intratumorally.

In one aspect, the IL-12 is administered near, adjacent or at the site of susceptible organ damage.

In one aspect, the subject is receiving radiation treatment for head and neck cancer and the IL-12 is administered at or near the site of irradiation.

In one aspect, the administered IL-12 protects muscosal tissue from radiation damage.

In one aspect, the radiation damage is caused by a nuclear explosion. In another embodiment, the radiation damage is caused by a release of radiation from an ionizing radiation source.

In one aspect, the radiation damage is caused by a radiation therapy treatment modality. In another embodiment, the treatment modality comprises external-beam radiation therapy. In one aspect, the external-beam radiation therapy comprises 3-dimensional conformal radiation therapy (3-D CRT). In another aspect, the external-beam radiation therapy is selected from the group consisting of intensity-modulated radiation therapy (IMRT), image-guided radiation therapy (IGRT), tomotherapy, stereotactic radiosurgery, stereotactic body radiation therapy, photon beam, electron beam and proton therapy.

In other aspects, the radiation therapy comprises internal radiation therapy or brachytherapy. In another aspect, the radiation therapy comprises systemic radiation therapy. In another aspect, the radiation therapy comprises radioimmunotherapy (RIT).

In one aspect, a pharmaceutical composition comprising IL-12 in a suitable formulation for delivery to a subject in need for the prevention of radiation-induced damage, is provided.

In one aspect, the administered IL-12 induces the production of at least one of erythropoietin, chemokines, cytokine, IFN-g, MCP-1, IL-15, IL-18, IP-10, MG, Mip1 beta, or I-TAC, Eotaxin, Eotaxin-3, TARC and IL-8. In some embodiments, the erythropoietin production enhances protection of system, organ, tissue and/or cellular damage.

In one aspect, the protected systems, organs and/or tissues comprise the bone marrow and the gastrointestinal system. In another aspect, the protected systems, organs and/or tissues comprise the kidney and lung. In another aspect, the protected systems, organs or tissues comprise the brain and the cardiovascular system.

In one aspect, the exemplary pharmaceutical compositions can protect or prevent cells, tissue and/or organs from damage following exposure to radiation. For example, in some aspects the exemplary pharmaceutical compositions can protect or prevent damage in hematopoietic tissues, blood, lymph, parenchymal cells of the bone marrow, circulating marrow blast cells, circulating small lymphocytes, platelets, white blood cells, red blood cells, skin and oral mucosa, basement layer of the skin, basal cells, epidermis, stem cells, digestive organs and systems, stomach, bowels, intestinal epithelium, colon, rectum, male and female reproductive systems, germinal cells, testis, ovaries, oocytes, liver, thyroid, vascular endothelium, blood vessels; eyes, lens, cardiovascular system, endothelium, heart, lung, bone and cartilage, connective tissue, liver, kidneys, CNS, sense organs, glial cells, and adrenal medulla.

In one aspect, the subject requires radiation treatment for cancer. In another aspect, the subject also requires chemotherapy.

In one aspect, the cancer is a solid tumor. In another aspect, the solid tumor comprises sarcomas, carcinomas or lymphomas. In another aspect, the cancer is selected from the group consisting of: lung, breast, prostate, pancreatic, ovarian, bladder, head and neck, thyroid, brain, liver, gallbladder, skin colon, and kidney. In one aspect, the solid tumor is a poorly reoxygenating tumor.

In one aspect, each dose of IL-12 is between about 1 ng/kg and less than about 2000 ng/kg, and said dose is administered by a delivery route selected from the group consisting of intradermal, intramuscular, intraperitoneal, intramuscular, intravenous, parenteral, intranasal, intracranial, topical, subcutaneous, and epidural routes.

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

BRIEF DESCRIPTION OF THE FIGURES

FIG. 6(a)-(c). Mice Bone Marrow Hematopoietic Stem Cells, Osteoblasts, And Megakaryocytes Express IL-12Rβ2. Tissue sections obtained 30 days (a and c) and 12 days (b) after TBI (according to the protocol described in FIG. 5) were stained immunohistochemically for IL-12Rβ2 (a and b, upper panels), markers of hematopoietic stem cells, Sca-1 (a, lower panel), and osteoblasts, osteocalcin (b, lower panel), or both IL-12Rβ2 and Sca-1 (c). Also both immature and mature megakaryocytes showed intense immunohistochemical staining for the presence of IL-12Rβ2 (c). Red arrows in (a) indicate hematopoietic stem cells that express IL-12Rβ2 while black arrows indicate those that do not express IL-12Rβ2. In IL-12Rβ2 and Sca-1 double staining (c) IL-12Rβ2 is stained pink while Sca-1 is stained brown. The subpopulation of stem cells co-expressing IL-12Rβ2 and Sca-1 as well as subpopulations expressing only IL-12Rβ2 or Sca-1 are indicated (c). Magnification=100×.

FIG. 17 showed efficacy of exemplary IL-12 (HemaMax) in the Stimulation of BM Regeneration Following Lethal Radiation Exposure.

FIG. 18 A-18 G. Examples of pockets of regeneration are illustrated in NHP bone marrow at day 12 after lethal irradiation (700 cGy). Pockets are defined by presence of H&E staining H&E stained regions are fewer and smaller in the vehicle treated animals (A-C). The increased frequency of stained regions and larger areas stained are evident in HemaMax treated NHP (D-G). Magnification at 4×.

FIG. 21A—Hematology: Lymphocytes. FIG. 21B—Hematology Neutrophils. FIG. 21C—Hematology: Platelets.

FIG. 31. Pharmacodynamics IFN-γ. IFN-γ Response after HemaMax Dosing.

FIG. 33. Pharmacodynamics of EPO—After a SC Dose of HemaMax in Non-Irradiated and Irradiated Monkeys.

DETAILED DESCRIPTION

Figure 1A:
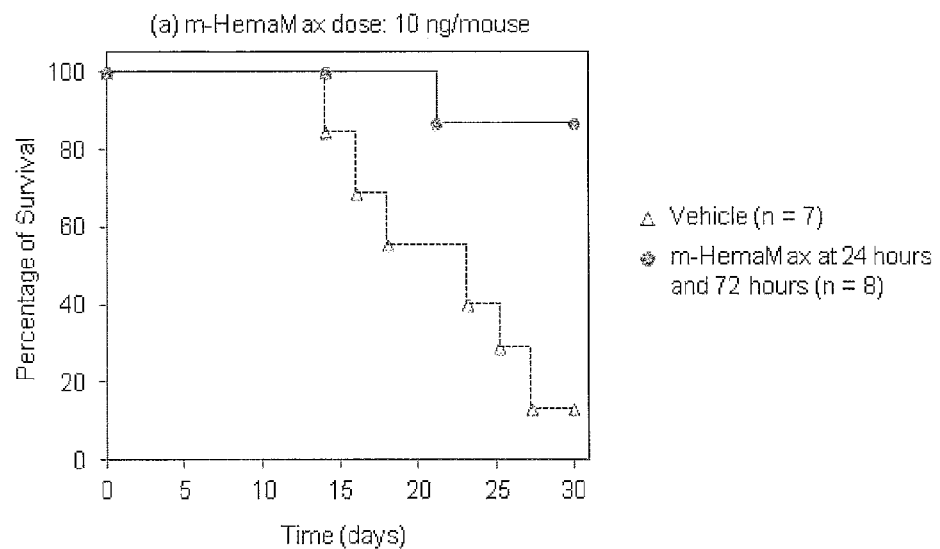
FIG. 1A-1C. Exemplary recombinant murine IL-12 (e.g. m HemaMax) administered at least 24 hours after TBI increased survival time of irradiated mice. (a) Animals received vehicle or recombinant murine IL-12 at an ostensible dose of 100 ng/mouse at 24 hours and 72 hours after a TBI of 8 Gy ($LD_{86/30}$). (b) Animals received vehicle or a single, ostensible dose of 300 ng/mouse of recombinant murine IL-12 at 24 hours, 48 hours, or 72 hours after a TBI of 9 Gy ($LD_{100/30}$). (c) Animals received vehicle or a single low dose of recombinant murine IL-12 (2 ng/mouse or 18 ng/mouse) at 24 hours after a TBI of 7.9 Gy ($LD_{85/30}$). Vehicle and recombinant murine IL-12 were injected subcutaneously. Vehicle was PBS in (a) and (b) and P5.6TT in (c). The delivered recombinant murine IL-12 dose was estimated to be 10 ng/mouse in (a) and 30 ng/mouse in (b) because subsequent studies showed that the actual recombinant murine IL-12 dose delivered was approximately 10% of the intended dose, most likely due to recombinant murine IL-12 sticking to surfaces of vials and syringes.

Accordingly, the present disclosure relates generally to novel methods and compositions for radiation protection and/or radiation-induced toxicity mitigation in connection with accidental radiation exposure (such as a nuclear explosion or a disaster scenario) and/or radiation therapy such as treatment of diseases and/or disorders associated with cutaneous T-cell lymphoma using electron beam therapy.

For example, the use of ionizing radiation or nuclear devices as weapons of terrorism is now recognized as a major public health threat. In the event of a nuclear detonation, terrorist radiological (e.g., "dirty") bomb, or attack on a nuclear power plant in a populated area, mass casualties will occur that will be in the need of immediate medical attention. At exposures approximating 4 Gy, it is estimated that 50% of individuals will die within 60 days unless there is medical intervention. The majority of deaths that occur from exposures of at least 2-10 Gy or more will result from the combined effects of immune, hematopoietic, and gastrointestinal (GI) failure, as these are the most radiosensitive tissues. There are no FDA approved therapeutic agents capable of increasing the chance for survival by simultaneously promoting or accelerating the recovery of the immune, hematopoietic and gastrointestinal compartments following radiation injury.

In the event of a radiation disaster or act of terrorism affecting a large civilian population, the goal would be to provide a potent frontline therapy that increases the chance for survival of the exposed, or potentially exposed, individuals. One of the challenges in such events is that medical care and treatments will not be available immediately following radiation exposure. It is envisioned that it will take 24 hours or more to mobilize medical teams and necessary life-saving drugs and equipment to the scene of a radiation disaster.

Since medical care will not be immediately available, a medical intervention capable of increasing the chance for survival as a frontline therapy would have to be efficacious when administered at protracted time points following radiation exposure. This is indeed a challenge in that total body irradiation (TBI) causes massive apoptosis to rapidly dividing cells in radiosensitive organs, such as the peripheral blood, bone marrow, and GI tract, starting immediately after radiation exposure. Moreover, the chance of successfully providing life-saving treatment to the exposed individuals decreases exponentially following radiation injury. Thus, the effectiveness of providing countermeasure treatments that could alleviate damage caused by radiation decreases rapidly with time Accordingly, certain aspects of the present disclosure relates generally to novel methods and compositions for radiation protection and/or radiation-induced toxicity mitigation due to acute radiation exposure.

In other aspects, the disclosure also provides methods and compositions for radiation protection or radiation toxicity mitigation for the treatment of diseases and/or disorders associated with cutaneous T-cell lymphoma using electron beam therapy.

Aspects and embodiments of the present disclosure address the unmet need for drugs that can protect and/or regenerate normal tissue while sparing cancerous tissue from the killing effects of radiation. To date there are no approved drugs that have these properties. Amifostine, a chemo- and radioprotectant is the only approved radiomitigation drug.

Amifostine is used therapeutically to (1) reduce the incidence of neutropenia-related fever and infection induced by DNA-binding chemotherapeutic agents including alkylating agents (e.g. cyclophosphamide) and platinum-containing agents (e.g. cisplatin); (2) decrease the cumulative nephrotoxicity associated with platinum-containing agents; and (3) reduce the incidence of xerostomia in patients undergoing radiotherapy for head and neck cancer. However, amifostine has the potential to promote the growth of tumor cells along with its potential to protect normal tissue. Consequently, this drug is used judiciously in cancer patients. Serious side effects of amifostine include: hypotension (found in 62% of patients), erythema multiforme, Stevens-Johnson syndrome and toxic epidermal necrolysis, immune hypersensitivity syndrome, erythroderma, anaphylaxis, and loss of consciousness (rare).

Small molecule kinase inhibitors are in early development as chemoprotectants but it is uncertain if these drugs will also protect cancer cells. Notably, there are no known radiomitigation drugs that concomitantly have anti-tumor effects. Recombinant human and/or murine IL-12 is the only radiomitigation drug in development that has been shown to have dual effects in animal models:

Recombinant human and/or murine IL-12 can protect and regenerate non-cancerous but damaged tissues following radiation exposure. Concomitant with its protective and regenerative properties following radiation, recombinant human and/or murine IL-12 can inhibit the growth of cancer cells. There is no other known drug that has these dual effects.

CTCL

As used herein, cutaneous T-cell lymphoma (CTCL) represents a group of lymphoid malignancies involving the skin. Primary cutaneous T-cell lymphoma (CTCL) represents a group of lymphoid malignancies involving the skin, representing approximately 60% to 70% of cutaneous lymphomas. Of the CTCL variants, mycosis fungoides (MF) is most common Staging is based on the Tumor, Node, Metastasis (TNM) system. Multiple options exist for the treatment of skin-limited MF, including photo (chemo)-therapy (psoralen plus ultraviolet A-PUVA), topical nitrogen mustard, carmustine BCNU), (radiotherapy such as total skin electron beam therapy (TSEBT), topical steroids, interferon alpha, retinoids such as bexarotene, receptor-targeted cytotoxic fusion proteins (e.g., Denileukin diftitox), and extracorporeal photopheresis. Because of the indolent but recurrent nature of MF, patients with MF often require multiple treatments.

Cutaneous T-cell lymphoma can generally be characterized by a group of lymphoproliferative disorders characterized by localization of neoplastic T lymphocytes to the skin. Cutaneous T cell lymphoma (CTCL) is a class of non-Hodgkin's lymphoma, which is a type of cancer of the immune system. Unlike most non-Hodgkin's lymphomas (which are generally B-cell related), CTCL is caused by a mutation of T cells. The malignant T cells in the body initially migrate to the skin, causing various lesions to appear. These lesions change shape as the disease progresses, typically beginning as what appears to be a rash which can be very itchy and eventually forming plaques and tumors before metastasizing to other parts of the body.

CTCL is a clonally derived malignant proliferation of skin-invasive CD41 T lymphocytes. Clinical manifestations of CTCL can encompass a broad spectrum of findings ranging from limited cutaneous patches and plaques with no overt peripheral blood or lymph node involvement to extensive skin involvement with tumors or erythroderma with concomitant blood, node, or visceral disease.

As used herein, cutaneous T-cell lymphomas may include but are not limited to the following types or classifications: Mycosis fungoides, Pagetoid reticulosis, Sézary syndrome, Granulomatous slack skin, Lymphomatoid papulosis, Pityriasis lichenoides chronica, Pityriasis lichenoides et varioliformis acuta, CD30+ cutaneous T-cell lymphoma, Secondary cutaneous CD30+ large cell lymphoma, Non-mycosis fungoides CD30– cutaneous large T-cell lymphoma, Pleomorphic T-cell lymphoma, Lennert lymphoma, Subcutaneous T-cell lymphoma, Angiocentric lymphoma, Blastic NK-cell lymphoma; Adult T-cell lymphoma/leukemia (human T-cell lymphotropic virus [HTLV]-positive); Nasal-type extranodal natural killer (NK)/T-cell lymphoma; primary cutaneous peripheral T-cell lymphoma, unspecified (PTCL-U).

As used herein, subjects suffering from CTCL can include clinical and/or subclinical presentation of characteristic features from the following CTCL related conditions:

WHO-EORTC Classification
Indolent Clinical Behavior
Mycosis fungoides
Mycosis fungoides variants and subtypes
Folliculotropic mycosis fungoides
Pagetoid reticulosis
Granulomatous slack skin
Primary cutaneous CD30+ lymphoproliferative disorder
Primary cutaneous anaplastic large cell lymphoma
Lymphomatoid papulosis
Subcutaneous panniculitis-like T-cell lymphoma (provisional)
Primary cutaneous CD4+ small/medium-sized pleomorphic T-cell lymphoma (provisional).
Aggressive Clinical Behavior
Sézary syndrome
Adult T-cell leukemia/lymphoma Moreover, CTCL can also include or be characterized by any of the following features and/or classifications:

Primary Cutaneous CD30-Positive Lymphoproliferative Disorder

The term CD30-positive lymphoproliferative disorders encompasses entities such as anaplastic large cell lymphoma (primary cutaneous and systemic type) and lymphomatoid papulosis. Although at times pathologically indistinct, these entities are clinically distinct. Thus, clinicopathologic correlation in the management of these disorders is desirable.

Anaplastic large cell lymphoma (ALCL), the primary cutaneous type, manifests as a solitary nodule or ulcerating tumor (>2 cm) in patients without a history of or concurrent mycosis fungoides or lymphomatoid papulosis and without evidence of extracutaneous disease. Extracutaneous dissemination, mainly to regional nodes, occurs 10% of the time. The disease is multifocal in skin approximately 30% of the time. CD30-positive (75% or more) membrane staining of the large lymphocytes or large clusters of CD30-positive atypical lymphocytes with pleomorphic or multiple nuclei and nucleoli are seen. Numerous mitotic figures can be observed. Unlike systemic anaplastic large cell lymphoma, anaplastic lymphoma kinase (ALK) staining is usually negative. A helpful tool for distinguishing cutaneous from systemic anaplastic large cell lymphoma is to test for the presence of the t(2;5) translocation. This translocation—although often, but not always, present in cases of systemic anaplastic large cell lymphoma—is usually absent in primary cutaneous cases. Differentiation from lymphomatoid papulosis is not always possible based on histologic criteria. Immunologically, atypical lymphocytes are CD4-positive, with variable loss of CD2, CD3, or CD5. Staging is required as per other non-Hodgkin lymphomas (e.g., using computed tomography [CT] scans, bone marrow examinations, blood work). Patients may experience spontaneous remissions with relapses. If no spontaneous remission occurs, radiation, surgical excision, or both are preferable. Chemotherapy is reserved for patients who have generalized lesions.

Lymphomatoid papulosis manifests as recurrent crops of self-healing, red-brown, centrally hemorrhagic or necrotic papules and nodules on the trunk or extremities; these can evolve to papulovesicular or pustular lesions. These lesions are much smaller than those of anaplastic large cell lymphoma (<2 cm). The lesions spontaneously resolve in 4-6 weeks, leaving hyperpigmentation or atrophic scars. Variable frequency and/or intensity of outbreaks can occur in different patients. Lymphomatoid papulosis is clinically benign, although clonal T-cell gene rearrangement can be demonstrated in 60-70% of cases. Hodgkin disease, mycosis fungoides, or cutaneous anaplastic large cell lymphoma is observed in 20% of cases.

Subcutaneous Panniculitis-Like T-Cell Lymphoma

In subcutaneous panniculitis-like T-cell lymphoma, erythematous subcutaneous nodules, which appear in crops, are localized to the extremities or trunk. These lesions may be confused with benign panniculitis and are often accompanied by fever, chills, weight loss, and malaise. They may also be accompanied by hemophagocytic syndrome, which may be associated with a rapidly progressive downhill course. Dissemination to extracutaneous sites is rare. Histologically, early lesions show focally atypical lobular lymphocytic infiltration of the subcutaneous fat that may also be confused with benign panniculitis. Later, infiltration of pleomorphic lymphoid cells into fat, with rimming of individual fat cells by the neoplastic cells, is accompanied by frequent mitoses, karyorrhexis, and fat necrosis. Cytophagic histiocytic panniculitis (histiocytes phagocytizing red and white blood cells) can also complicate the histologic picture. Immunologically, atypical lymphocytes stain positively for CD3 and CD8, with clonal rearrangement of the T-cell receptor gene documented. At least 2 groups of subcutaneous panniculitis-like T-cell lymphoma with different histologies, phenotypes, and prognoses can be distinguished. Cases with an alpha/beta-positive T-cell phenotype are usually CD8$^+$, are characterized by recurrent lesions that are restricted to the subcutaneous tissue (with no dermal or epidermal involvement), and tend to run an indolent clinical course. The WHO-EORTC term subcutaneous panniculitis-like T-cell lymphoma refers only to the alpha/beta type. Although affected patients were treated with chemotherapy or radiation in the past, it appears that patients treated with systemic steroids may remain in good clinical control. A similar-appearing lymphoma with a gamma/delta phenotype is CD8$^-$ and CD56$^+$. Histologically, the infiltration may not be limited to the subcutaneous tissue, and the course may be more aggressive. In the WHO-EORTC classification, this lymphoma is considered to be a different entity and is included in the group of cutaneous gamma/delta-positive lymphomas in a provisional category. Clinically, this lymphoma is more aggressive, with dissemination to mucosal and other extranodal sites.

Primary Cutaneous CD4$^+$ Small/Medium-Sized Pleomorphic T-Cell Lymphoma

This condition presents with solitary or localized plaques or tumors in the face, neck, and/or upper trunk area. The disease typically has an indolent course, and solitary lesions may be treated with surgical excision or radiation. Histologically, dermal to subcutaneous infiltration with CD3, CD4$^+$ malignant cells is seen, and focal epidermotropism may be seen.

Provisional categories, such as primary aggressive epidermotropic CD8$^+$ cytotoxic T-cell lymphoma and primary cutaneous CD4$^+$ small/medium-sized pleomorphic T-cell lymphoma, are also included. Cutaneous gamma/delta-positive T-cell lymphoma also belongs in this category. Sezary syndrome is also included as well as mycosis fungoides.

Adult T-Cell Lymphoma/Leukemia

Most patients with adult T-cell lymphoma/leukemia are those with antibodies to HTLV-1, a virus endemic to Southwest Japan, South America, Central Africa, and the Caribbean. Adult T-cell lymphoma/leukemia develops in 1-5% of seropositive individuals, often 20 years after exposure. In the acute form, cutaneous lesions, hepatosplenomegaly, lytic bone lesions, and infections are observed, along with an elevated white blood cell (WBC) count and hypercalcemia. In the chronic and smoldering forms, the skin rash is characterized by papules, nodules, plaques, or erythroderma with pruritus, which can resemble mycosis fungoides histologically and clinically. Cells with hyperlobate nuclei (in a clover-leaf pattern) infiltrate the dermis and subcutis. Epidermotropism with Pautrier microabscesses can be seen in one third of cases. Immunologically, the malignant cells are positive for CD2, CD3, and CD5 but negative for CD7; CD4 and CD25 are positive. The T-cell gene rearrangement is clonal, and the HTLV-1 genome is integrated into the neoplastic cells' genome. Standard treatment with chemotherapy does not appear to affect survival. The use of zidovudine and interferon has been advocated. The prognosis in patients with adult T-cell lymphoma/leukemia is poor, with a 6-month median survival for the acute form and a 24-month median survival for the chronic form.

Nasal-Type Extranodal NK/T-Cell Lymphoma

In nasal-type extranodal NK/T-cell lymphoma, a disease characterized by small, medium, and large cells, the nasal cavity/nasopharynx and the skin of the trunk and extremities are involved by multiple plaques and tumors. These lesions are frequently accompanied by systemic symptoms such as fever and weight loss, and an associated hemophagocytic syndrome may be observed. Cutaneous involvement may be primary or secondary. Because both primary involvement and secondary involvement are clinically aggressive and require the same type of treatment, distinction between the 2 cutaneous involvements seems unnecessary. This condition is more common in males and geographically is more common in Asia, Central America, and South America. Dermal and subcutaneous infiltration with invasion of the vascular walls and occlusion of the vessel lumen by lymphoid cells lead to tissue necrosis and ulceration. The malignant cells are usually CD2 and CD56 positive (NK phenotype), with cytoplasmic, but not surface, CD3 positivity. The cells contain cytotoxic proteins (T-cell intracellular antigen 1 [TIA-1], granzyme B, and perforin). Epstein-Barr virus (EBV) tests are commonly positive. Rarely, the cells may have a true cytotoxic T-cell phenotype. Nasal-type extranodal NK/T-cell lymphoma is an aggressive disease that requires systemic therapy, although the experience with systemic chemotherapy has generally been poor.

Primary Cutaneous Peripheral T-Cell Lymphoma, Unspecified

PTCL-U is a heterogeneous entity that manifests with localized or generalized plaques, nodules, and/or tumors. By definition, this group excludes all 3 provisional categories of PTCLs delineated in the WHO-EORTC classification. The absence of previous or concurrent patches or plaques consistent with mycosis fungoides differentiates these lesions from classic mycosis fungoides in transformation to diffuse large cell lymphoma. Pleomorphic infiltration of small/large lymphocytes is observed diffusely infiltrating the dermis.

Large, neoplastic T cells are present by greater than 30%. The immunophenotype is generally CD4+. Immunologically, most neoplastic lymphocytes show an aberrant CD4-positive phenotype with clonal rearrangement of T-cell receptor genes. Results from CD30 staining are negative. Patients with PTCL-U generally have a poor prognosis and should be treated with systemic chemotherapy. The 4-year survival rate approaches 22%. Although a small percentage of patients may undergo spontaneous remission, a more aggressive behavior is more likely. Staging for systemic lymphoma and multiagent chemotherapy is recommended. If the patient has solitary or localized disease, radiation therapy could be considered as an initial treatment.

Primary Cutaneous Aggressive Epidermotropic CD8+ Cytotoxic T-Cell Lymphoma

Primary cutaneous aggressive epidermotropic CD8+ cytotoxic T-cell lymphoma is a clinically aggressive, (sometimes) disseminated disease that presents with eruptive papules, nodules, and tumors with central ulceration. This entity can also present with superficial patches and/or plaques. Affected patients have typically been treated with anthracycline-based systemic chemotherapy. Histologically, epidermotropism with invasion and destruction of adnexal skin structures and angiocentricity with angioinvasion can be seen. The malignant cells are CD3- and CD8-positive and contain cytotoxic proteins. Clonal T-cell gene rearrangement is seen. EBV tests are typically negative in primary aggressive epidermotropic CD8+ cytotoxic T-cell lymphoma.

Mycosis fungoides is the most common type of cutaneous T-cell lymphoma (44%), which has led some authors to use this term synonymously with cutaneous T-cell lymphoma. Cutaneous T-cell lymphoma is a relatively common clonal expansion of T helper cells and, more rarely, T suppressor/killer cells or NK cells, that usually appears as a widespread, chronic cutaneous eruption. Mycosis fungoides itself is often an epidermotropic disorder and is characterized by the evolution of patches into plaques and tumors composed of small to medium-sized skin-homing T cells; some (or, rarely, all) of these T cells have convoluted, cerebriform nuclei. The term mycosis fungoides was first used in 1806 by Alibert, a French dermatologist, when he described a severe disorder in which large, necrotic tumors resembling mushrooms presented on a patient's skin. Approximately 1000 new cases of mycosis fungoides occur per year (i.e., 0.36 cases per 100,000 population). This condition is more common in black patients than in white patients (incidence ratio=1:6), and it occurs more frequently in men than in women (male-to-female ratio, 2:1). The most common age at presentation is 50 years; however, mycosis fungoides can also be diagnosed in children and adolescents and apparently has similar outcomes. Variants of mycosis fungoides that are recognized by WHO/EORTC include Sézary syndrome, folliculotropic mycosis fungoides, granulomatous slack skin, and pagetoid reticulosis (Woringer-Kolopp disease).

Sézary syndrome

Sézary syndrome accounts for about 5% of all cases of mycosis fungoides. The patient with Sézary syndrome has generalized exfoliative erythroderma and lymphadenopathy, as well as atypical T lymphocytes with cerebriform nuclei (more than 1000 per mm$^3$) circulating in the peripheral blood or other evidence of a significant malignant T-cell clone in the blood, such as clonal T-cell gene rearrangement identical to that found in the skin. (See the images below.)

The T-cell gene rearrangement is demonstrated by molecular or cytogenetic techniques and/or an expansion of cells with a malignant T-cell immunophenotype (an increase of CD4+ cells such that the CD4/CD8 ratio is >10, and/or an expansion of T cells with a loss of 1 or more of the normal T-cell antigens [e.g., CD2, CD3, CD5]). The circulating malignant cells tend to be CD7 and CD26 negative. Although Sézary syndrome may be part of a continuum from erythrodermic mycosis fungoides, the WHO-EORTC classification for cutaneous lymphoma considers its behavior "aggressive.

Folliculotropic Mycosis Fungoides

Folliculotropic mycosis fungoides manifests with follicular papules, patchy alopecia, and comedolike lesions, particularly in the head and neck area. An infiltration of atypical lymphocytes is observed in the epithelium of hair follicles, and mucinous degeneration of the hair follicles (follicular mucinosis) may be seen. Topical treatments may not be effective because of the depth of infiltration.

Pagetoid Reticulosis

Pagetoid reticulosis, or Woringer-Kolopp disease, manifests with a solitary, asymptomatic, well-defined, red, scaly patch or plaque on the extremities that may slowly enlarge. A heavy, strictly epidermal infiltrate of atypical lymphocytes is observed. The prognosis is excellent, with radiation therapy or surgical excision being the treatment of choice. The term pagetoid reticulosis should be restricted to the localized type and should not be used to describe the disseminated type (Ketron-Goodman type).

Granulomatous Slack Skin

Granulomatous slack skin is a condition characterized by the slow development of pendulous, lax skin, most commonly in the areas of the axillae and groin. Histologically, a granulomatous infiltration is seen, accompanied by multinucleate giant cells with elastophagocytosis and an almost complete loss of elastin in the dermis (demonstrated by elastin stain). Disease recurrence is common after surgical intervention. Radiation may be of use, but experience with it in this disease is limited. One third of patients have been reported to have concomitant Hodgkin lymphoma or mycosis fungoides.

Granulomatous cutaneous T-cell lymphomas are rare, so limited data on their clinicopathologic and prognostic features are available. Patients with either granulomatous mycosis fungoides or granulomatous slack skin display overlapping histologic features. The development of bulky skin folds in granulomatous slack skin differentiates this condition clinically from granulomatous mycosis fungoides.

Of all primary cutaneous lymphomas, 65% are of the T-cell type. The most common immunophenotype is CD4 positive. There is no common pathophysiology for these diseases, as the term cutaneous T-cell lymphoma encompasses a wide variety of disorders. Mycosis fungoides is a malignant lymphoma characterized by the expansion of a clone of CD4+ (or helper) memory T cells (CD45RO+) that normally patrol and home in on the skin. The malignant clone frequently lacks normal T-cell antigens such as CD2, CD5, or CD7. The normal and malignant cutaneous T cells home in on the skin through interactions with dermal capillary endothelial cells. Cutaneous T cells express cutaneous lymphocyte antigen (CLA), an adhesion molecule that mediates tethering of the T lymphocyte to endothelial cells in cutaneous postcapillary venules via its interaction with E selectin. Further promoting the proclivity of the cutaneous T cell to home in on the skin is the release by keratinocytes of cytokines, which infuse the dermis, coat the luminal surface of the dermal endothelial cells, and upregulate the adhesion molecules in the dermal capillary endothelial lumen, which react to CC chemokine receptor 4 (CCR4) found on cutaneous T cells.

Extravasating into the dermis, the cells show an affinity for the epidermis, clustering around Langerhans cells (as seen microscopically as Pautrier microabscesses). However, the malignant cells that adhere to the skin retain the ability to exit the skin via afferent lymphatics. They travel to lymph nodes and then through efferent lymphatics back to the blood to join the circulating population of CLA-positive T cells. Thus, mycosis fungoides is fundamentally a systemic disease, even when the disease appears to be in an early stage and clinically limited to the skin.

Treatment of CTCL

Treatment of patients with CTCL includes both topical and systemic therapies. The most common therapies include but not limited to psoralene plus UVA irradiation (PUVA), electron beam therapy, which includes local and total skin electron beam therapy (TSEBT); and topical- and systemic chemotherapy; or combinations thereof in a combined modality therapy.

Typical CTCL Treatment Options

| Treatment Option | 1) Nature of Treatment Approach |
|---|---|
| 2) Electron beam therapy | 3) Radiation therapy |
| 4) Topical or systemic chemotherapy | 5) Chemotherapy |
| 6) Phototherapy with UV light (PUVA) | 7) Radiation therapy |
| 8) Targretin (Bexarotene) | 9) RXR-selective retinoid |
| 10) Denileukin Difitox (Diphtheria toxin-Interleukin-2 fusion protein) | 11) mAb-targeted chemotherapy |
| 12) Interferon alpha + PUVA | 13) Biologic response modifier |

In one embodiment, the treatment for the CTCL is electron beam therapy. In one embodiment, the treatment for the CTCL is local electron beam therapy. In one embodiment, the treatment for the CTCL is total skin electron beam therapy. In one embodiment, the treatment for the CTCL is electron beam therapy in combination with at least one other modality and/or therapeutic agent.

As used herein, modalities and/or agents suitable for use in combined modality therapy in combination with electron beam therapy can include, for example, moisturizing cream, PUVA, bexarotene, topical steroids, extracorporeal photopheresis, UVB light therapy, interferon, nitrogen mustard, methotrexate cream, BCNU cream, nitrogen mustard, local radiation therapy, systemic chemotherapy, etanercept, Ontak, and antifungal cream. These prior therapies are a diverse admixture of topical and systemic modalities.

As used herein, other agents suitable for combined modality therapy with local or TSEBT in the treatment of CTCL can include, for example, Denileukin diftitox (Ontak); (2000) Bexarotene (Targretin) a retinoid; (2006) Vorinostat (Zolinza) a hydroxymate histone deacetylase (HDAC) inhibitor; (2009) Romidepsin (Istodax) a cyclic peptide histone deacetylase (HDAC) inhibitor; agents for off label Treatments such as, for example, topical and oral corticosteroids; Bexarotene (Targretin) gel and capsules; Carmustine (BCNU, a nitrosourea); Mechlorethamine (Nitrogen Mustard); Phototherapy (Broad & Narrow Band UVB or PUVA); Conventional Radiation Therapy; Photopheresis; Interferons; Alemtuzumab (Campath-1H); Methotrexate; Pentostatin and other purine analogues (Fludarabine, 2-deoxychloroadenosine); Liposomal doxorubicin (Doxil); Gemcitabine (Gemzar); Cyclophosphamide; Bone marrow/stem cells; Allogenic transplantation; Forodesine (Inhibits Purine Nucleoside phosphorylase); and/or panobinostat).

General Aspects of Electron Beam Therapy

EBT is one of the most effective therapies for CTCL. Unfortunately most patients develop dose limiting toxicity and are unable to receive repeated courses or larger doses EBT. Total skin EBT (TSEBT) may be considered as initial therapy for patients with extensive thick plaques, since the effective depth of treatment of TSEBT is more substantial than either topical nitrogen mustard or phototherapy, but usually it is reserved for later stages due to potential cumulative toxicity of radiation. EBT may also be appropriate for patients with rapid progression of disease and for those patients who failed other therapies such as topical nitrogen mustard, bexarotene gel and/or phototherapy. Many of these patients would benefit from TSEBT and local EBT for efficient control of disease. The most dramatic responses are observed in patients with tumorous disease, i.e., disease with thick plaques, and nearly all such patients are considered appropriate candidates for total skin irradiation. However, the majority of patients treated with total skin irradiation will eventually develop recurrent disease, although long-term remissions have been reported. In addition, acute side effects such as epitheliolysis, hypohidrosis, blisters/skin ulcers, mucositis, and alopecia can occur in most patients treated with EBT.

Maintenance Therapies for EBT

Because the majority of patients treated with total skin irradiation will eventually develop recurrent disease, a variety of adjunct or maintenance therapies are utilized after completion of electron beam therapy. These include topical nitrogen mustard, PUVA, oral etretinate, extracorporeal photopheresis and systemic chemotherapy. Topical nitrogen mustard in aquaphor provides the dual benefit of treatment for any residual disease and emolliation of the skin, which is often chronically dry after completion of TSEB therapy. These maintenance therapies may delay the time to relapse, but there is little evidence of improved long-term, disease-free survival.

Biological Response Modifiers

Biological response modifiers can provide a useful treatment for patients with CTCL. They include interferons, cytokines, a variety of retinoids, and combinations thereof. Alpha interferon is an effective single agent (50% response rate) and is usually given 3-5 million units three times weekly. Its efficacy is limited by the development of antibodies and its systemic flu-like symptoms and the remission duration is usually short with a median of six months. Combination therapy of interferon and PUVA or retinoids is highly effective, even in some stage IV or tumor patients. There are two classes of retinoid receptors, RAR and RXR. Once a retinoid enters the cell, it binds a receptor, forms RAR and RXR heterodimers, and is translocated into the nucleus where it interacts with transcription factors. In this way, retinoids interact with gene promoters to regulate transcription. Well known retinoids such as acitretin, etretinate, and 13-cis retinoic acid interact with RAR receptors, but Targretin is a new RXR selective retinoid. All of these retinoids have been used in CTCL. Small trials have shown similar efficacy for etretinate and 13-cis retinoic acid (50-60% response rate).

Local disease may be treated with low-energy X-rays or electrons. Electrons have an intrinsic advantage over X-rays since the depth of penetration of electrons can be controlled by the appropriate selection of electron energy. The relative dose contribution to the subcutaneous and deeper tissues is greater with even low-energy photons, compared to electrons. For indurated plaques, electron energies as low as 6 MeV are generally sufficient. Use of bolus may be indicated because of the relative "skin-sparing" effect of low energy electrons. For lower energy electrons, there is a relative "skin sparing" effect, i.e., the maximum dose is actually deep to the skin surface. Since the lesions of MF are so superficial, it is desirable to have the maximum dose at the skin surface. This can be achieved by the use of tissue-equivalent bolus material of 0.5-1.0 cm thickness. For treating individual lesions, an electron energy should be selected that provides an adequate depth of penetration through the entire depth of involvement by the patch, plaque or tumor, with at least 0.5 cm of penetration beyond. For the typical patch or thin plaque, treatment with 6-9 MeV electrons with 1.0 cm of bolus usually suffices. Exophytic tumors may require 9-12 MeV electrons. Peripheral margins of up to 2 cm are recommended, but may be dependent upon location and proximity to sensitive tissues.

TSEBT

The ability to irradiate the entire skin is dependent upon the development of electron beam therapy. The depth dose characteristics of the electron beam make it possible to treat large surfaces of the skin in a single field, concentrating the dose of irradiation in the epidermis and upper dermis, while limiting the dose to the deep dermis and subcutaneous tissue.

A linear accelerator accelerates electrons that are made to impinge on a target in order to produce high-energy photons (X-rays). The basic approach of the "Stanford technique" was to replace the target at the end of the linear accelerator with an electron scattering foil, thereby generating a diffuse electron beam. The patient stood about 10 feet/3 meters from the end of the accelerator, and her or his entire surface could be treated with the broad electron beam. By using multiple field techniques, it was possible to irradiate the entire cutaneous surface. At Stanford, a four-field technique was utilized at first, and later, a six-field technique of treatment was introduced.

In general, the dosimetry of total skin electron irradiation improves as the number of fields of treatment increases. With four-field treatment, there is significant overlap of adjacent fields, creating "hot spots" which may result in long-term telangiectasia, subcutaneous fibrosis and even necrosis. These complications may be accentuated by fractionation programs that use larger doses per fraction or fewer fractions per week. In a typical set up, patients are treated in the standing position at a distance of 3. 5 m from the isocenter (electron source). A ⅜-inch/1 cm Lucite plate is placed as close as possible to the patient surface in order to degrade and further scatter the electrons. During treatment, the machine is angled upwards or downwards at an angle of 18 Åã. The combination of these two fields for treating each body surface results in a very homogeneous dose distribution at the patient's surface and minimizes photon contamination, which is greatest in the central axis of the beam. Patients are now treated with a six-field technique that includes anterior, posterior and four opposed oblique fields. A full "cycle" of treatment is administered over a 2-day period. On day 1, the anterior and two posterior oblique fields are treated at each of the two accelerator angles. On day 2, the posterior and two anterior oblique fields are treated at each of the two accelerator angles. The dose administrated with each cycle is about 1.5-2 Gy. Most patients will tolerate about 2 Gy per cycle, but lower doses are used for patients with erythroderma, atrophic skin, or a previous course of electron beam therapy. The prescribed total dose is about 30-36 Gy administered over a about 9- to 10-week period. A one-week split has been introduced after a dose of about 18-20 Gy has been delivered in order to provide for some relief from the generalized skin erythema that usually accompanies treatment.

With this exemplary technique, certain portions of the body surface are "shadowed" and receive relatively lower total doses of irradiation. These areas include the top of the scalp, the perineum and the soles of the feet. Other areas may be problematic in individual patients because of body habitus, such as underneath the breasts of some women and under the panniculus of obese individuals. In order to compensate for this effect, we routinely treat the perineum and soles of the feet using about 6-MeV electrons (with 1-cm, tissue-equivalent bolus) with daily fractions of about 1.0 Gy to a total of about 20 Gy. Supplemental treatment is provided to the vertex of the scalp only if there is scalp involvement, since permanent alopecia may result. Supplemental treatment also is administered underneath the breasts and panniculus of individual patients, as indicated. In addition, some patients with a discrete number of tumorous lesions will receive boost treatment to these tumors at the outset of electron beam therapy in order to reduce their thickness and permit better penetration by the electrons. Usually, doses of about 15 Gy in about 1.5-3. 0-Gy fractions using about 6-9-MeV electrons are adequate for this purpose. In the standard course of treatment, only the eyes are shielded. Internal lead eye shields with an inner coating of paraffin or dental acrylic are used whenever disease is present on the face or scalp. The shields are placed under the lids after the eyes have been anesthetized topically. If disease is absent from these areas, external lead eye shields, which are taped over the closed eyes, are utilized. In addition, in the absence of involvement of the scalp or face, scalp shielding is utilized after a dose of 25 Gy in order to facilitate adequate regrowth of scalp hair. Complete scalp shielding is contraindicated and may result in extension of disease to this area. Individualized shielding is utilized as clinical circumstances demand. For example, some patients It has minimal penetration to dermis and deeper tissues and therefore causes relatively few side effects. TSEBT should be considered as initial therapy for patients with thickened plaques, because TSEBT is more effective in the depth of the plaques than topical therapies, such as nitrogen mustard and phototherapy. In patients with rapid progression of disease and patients, experiencing failure of local therapy TSEBT can be an effective treatment for achieving disease control. The total doses applied to the skin are usually about 30-36 Gy over about 8-10 weeks. The overall clinical response rates after TSEBT are nearly 100% and complete response rates range from 98% for limited plaque stage to 40% for tumor stage. However, the majority of the patients treated with TSEBT will experience recurrent disease. To delay the time to relapse, maintenance and adjuvant therapies are often used after TSEBT.

In one embodiment, the patients were treated with high-dose (about 30 Gy) local and/or total skin electron beam therapy. In another embodiment, the patients were treated with low-dose (about 4 Gy) local and/or total skin electron beam therapy.

Accordingly, aspects and embodiments of the instant disclosure provide therapeutic compositions and methods of use thereof comprising IL-12, including recombinant human interleukin-12 (IL-12) preparation for treating, reducing or preventing radiation induced damage effects, including acute radiation syndrome in humans and/or radiation induced cytotoxicity associated with local or total skin electron beam irradiation.

IL-12

As used herein, exemplary recombinant murine IL-12 (e.g. any suitable recombinant-murine IL-12 preparation, including, for example, a glycosylated version of recombinant murine IL-12 produced in CHO cells; hereinafter "recombinant murine IL-12" was obtained from Peprotech (Rocky Hill, N.J., USA) or provided by SBH Sciences (Natick, Mass., USA) to Neumedicines. Exemplary recombinant human IL-12, rHuIL-12 (e.g. any suitable recombinant-human IL-12 preparation, including, for example, a glycosylated version of recombinant human IL-12 produced in CHO cells; hereinafter "recombinant human IL-12") was provided by SBH Sciences (Natick, Mass., USA) to Neumedicines.

IL-12 is a heterodimeric cytokine, comprising both p40 and p35 subunits, that is well-known for its role in immunity. In numerous reports spanning about two decades, IL-12 has been shown to have an essential role in the interaction between the innate and adaptive arms of immunity by regulating inflammatory responses, innate resistance to infection, and adaptive immunity. Endogenous IL-12 is required for resistance to many pathogens and to transplantable and chemically induced tumors. The hallmark effect of IL-12 in immunity is its ability to stimulate the production of interferon-γ (IFN-γ) from natural killer (NK) cells, macrophages and T cells. Further, several in vitro studies in the early-mid nineties reported that IL-12 is capable of stimulating hematopoiesis synergistically with other cytokines. The hematopoiesis-promoting activity of IL-12 appears to be due to a direct action on bone marrow stem cells as these studies used highly purified progenitors or even single cells. The role of IFN-γ in the hematopoietic activity of IL-12 is not clear as several studies have linked both the promotion and suppression of hematopoiesis to IFN-γ.

As used herein, exemplary recombinants murine and human IL-12 compositions and formulations can be based on the following sequences, including for example, fragments, structural homologs, sequence homologs, functional homologs, and/or derivatives thereof in a pharmaceutically acceptable vehicle or carrier.

```
rHUIL-12:
IL12A (p35)
                                     (SEQ ID No 1)
RNLPVATPDPGMFPCLHHSQNLLRAVSNMLQKARQTLEFYPCTSEEID

HEDITKDKTSTVEACLPLELTKNESCLNSRETSFITNGSCLASRKTSF

MMALCLSSIYEDLKMYQVEFKTMNAKLLMDPKRQIFLDQNMLAVIDEL

MQALNFNSETVPQKSSLEEPDFYKTKIKLCILLHAFRIRAVTIDRVMS

YLNAS

IL12B (p40)
                                     (SEQ ID No 2)
IWELKKDVYVVELDWYPDAPGEMVVLTCDTPEEDGITWTLDQSSEVLG

SGKTLTIQVKEFGDAGQYTCHKGGEVLSHSLLLLHKKEDGIWSTDILK

DQKEPKNKTFLRCEAKNYSGRFTCWWLTTISTDLTFSVKSSRGSSDPQ

GVTCGAATLSAERVRGDNKEYEYSVECQEDSACPAAEESLPIEVMVDA

VHKLKYENYTSSFFIRDIIKPDPPKNLQLKPLKNSRQVEVSWEYPDTW

STPHSYFSLTFCVQVQGKSKREKKDRVFTDKTSATVICRKNASISVRA

QDRYYSSSWSEWASVPCS

Mouse IL-12:
Mouse IL-12A (p35)
                                     (SEQ ID No 3)
RVIPVSGPARCLSQSRNLLKTTDDMVKTAREKLKHYSCTAEDIDHEDI

TRDQTSTLKTCLPLELHKNESCLATRETSSTTRGSCLPPQKTSLMMTL

CLGSIYEDLKMYQTEFQAINAALQNHNHQQIILDKGMLVAIDELMQSL

NHNGETLRQKPPVGEADPYRVKMKLCILLHAFSTRVVTINRVMGYLSS

AM

Mouse IL-12 B (p40)
                                     (SEQ ID No 4)
WELEKDVYVVEVDWTPDAPGETVNLTCDTPEEDDITWTSDQRHGVIGS

GKTLTITVKEFLDAGQYTCHKGGETLSHSHLLLHKKENGIWSTEILKN

FKNKTFLKCEAPNYSGRFTCSWLVQRNMDLKFNIKSSSSSPDSRAVTC

GMASLSAEKVTLDQRDYEKYSVSCQEDVTCPTAEETLPIELALEARQQ

NKYENYSTSFFIRDIIKPDPPKNLQMKPLKNSQVEVSWEYPDSWSTPH

SYFSLKFFVRIQRKKEKMKETEEGCNQKGAFLVEKTSTEVQCKGGNVC

VQAQDRYYNSSCSKWACVPCRVRS
```

Interleukin-12 (IL-12) is shown to have a radioprotective function when used before or shortly after exposure to total body radiation (Neta et al. (1994) IL-12 protects bone marrow from and sensitizes intestinal tract to ionizing radiation; J Immunol 153: 4230-4237; Chen et al., (2007) IL-12 facilitates both the recovery of endogenous hematopoiesis and the engraftment of stem cells after ionizing radiation, Exp Hematol 35: 203-213); US20110206635 and U.S. Pat. No. 7,939,058. In the studies, mice were rescued from the deleterious effects of lethal total body radiation. The radioprotective effect was reported to reside within an unknown cell population in the bone marrow, likely long-term repopulating hematopoietic stem cells. In another study, IL-12 was shown to provide early recovery peripheral blood cell counts following sublethal radiation of tumor-bearing mice. (Basile et al. (2008) Multilineage hematopoietic recovery with concomitant antitumor effects using low dose Interleukin-12 in myelosuppressed tumor-bearing mice. J Transl Med 6: 26). In this latter study, it was shown that IL-12 was synergistic with radiation in reducing tumor volume. In particular, IL-12 did not to increase tumor volumes when administered either before or after radiation exposure.

Thus, IL-12 has potential in radioprotection of the bone marrow following total body radiation. However, early studies reported that although IL-12 had a radioprotective effect in the bone marrow, the gastrointestinal (GI) system was sensitized to radiation damage (Neta et al.). In a later report, the GI sensitization effect of IL-12 was found to be dependent on the dose of IL-12 administered (Chen et al.). There have been no reports of the radioprotective effects of IL-12 to other tissues or organs, other than bone marrow.

The present invention is based a surprising and unexpected discovery that certain murine recombinant IL-12 (e.g. m-HemaMax) and human recombinant IL-12 (e.g. HemaMax) have the ability to increase survival (including when administered at protracted time points post total body irradiation (TBI) in both mice, non-human primates (NHP) and humans respectively. In addition, aspects of the present invention are based on the surprising discovery that-recombinant human IL-12 have the ability to treat, prevent, and/or reduce radiation induced cytotoxicity or damage associated with radiation therapy, including electron beam therapy. In a model of radiomitigation, where single, low doses of recombinant murine IL-12 in mice or recombinant human IL-12 in NHP are administered subcutaneously at 24 hours or longer post irradiation, the inventor discovered that recombinant human IL-12 can provide potent mitigation of radiation injury to multiple tissues, including the immune, bone marrow, and GI compartments, leading to significant increases in survival for both murine and NHP radiomitigation models in the complete absence of supportive care. To our knowledge, this is the first report showing potent radiomitigation effects of a therapeutic agent in mice and NHP at protracted time points post radiation, such as 24 hours or longer, following acute ionizing radiation exposure.

The present invention provides embodiments of the multitissue or multi-organ radioprotective effects of IL-12 following radiation exposure based on the surprising and unexpected discovery that in addition to protection of the bone marrow compartment, the IL-12-mediated radioprotective effects include protection of various tissues, organs and system when administered in accordance with aspects and embodiments of the instant disclosure. The tissues, organs and systems include the bone marrow, lymphatic system, immune system, mucosal tissue, mucosal immune system, gastrointestinal system, cardiovascular system, nervous system, reproductive organs, prostate, ovaries, lung, kidney, skin and brain.

For the purpose of the current disclosure, the following definitions shall in their entireties be used to define technical terms and to define the scope of the composition of matter for which protection is sought in the claims.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating or controlling.

As used herein, the term "treating" refers to both therapeutic treatment and prophylactic or preventative measures, or administering an agent suspected of having therapeutic potential.

The term "a pharmaceutically effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

As used herein, an "effective amount" in reference to the pharmaceutical compositions of the instant disclosure refers to the amount sufficient to have utility and provide desired therapeutic endpoint.

As used herein, radiation induced damage following total body irradiation (TBI) can affect organ, tissues, systems associated with the following: bone marrow, lymphatic system, immune system, mucosal tissue, mucosal immune system, gastrointestinal system, cardiovascular system, nervous system, reproductive organs, prostate, ovaries, lung, kidney, skin and brain.

In certain embodiments, the treatment related radiation induced damage or toxicity can include, for example, erythema, hyperpigmentation, itching, alopecia, mucositis, desquamation, blisters, edema of the limbs (hands and feet) associated with total skin electron irradiation. Other side effects can include alteration in body temperature control due to radiation induced normal tissue damage to the sweat glands.

As used herein, radiation exposure may be associated with radiation-induced acute, chronic, and systemic damage effects. In one aspect, the instant disclosure provides therapeutic compositions and methods of use thereof for treating radiation induced acute damage effects. In one aspect, the instant disclosure provides compositions and methods of use thereof for treating radiation induced cytotoxicity associated with local and/or total skin electron beam irradiation associated with CTCL. Exemplary damage effects are not always limited to the normal tissue in the irradiation beam. Exemplary damage effect can extend beyond the treated area and can include, for example, esophagitis (difficulty swallowing); pneumonitis (cough, fever, lung fluid accumulation) in the lung; intestinal irradiation-induced inflammation (diarrhea, cramps, abdominal pain); nausea and vomiting; tiredness, fatigue, diarrhea, headache, tissue swelling, skin erythema, cough, and difficulty breathing. Exemplary damage effects can affect areas of the skin e.g. erythema, desquamation; oral mucosa, e.g. mucositis, nasopharynx; oropharynx; vocal cord; tonsil; skin, (squamous or carcinoma). In certain embodiments, exemplary effects can include telangiectasia, fibrosis, spinal cord myelitis, and cartilage fibrosis.

In certain embodiments, exemplary radiation induced damage effects can also include Blood-forming organ (Bone marrow) syndrome, characterized by damage to cells that divide at the most rapid pace (such as bone marrow, the spleen and lymphatic tissue). Exemplary symptoms include internal bleeding, fatigue, bacterial infections, and fever.

In certain embodiments, exemplary radiation induced damage effects can also include gastrointestinal tract syndrome, characterized by damage to cells that divide less rapidly (such as the linings of the stomach and intestines). Exemplary symptoms include nausea, vomiting, diarrhea, dehydration, electrolytic imbalance, loss of digestion ability, bleeding ulcers, and the symptoms of blood-forming organ syndrome.

In certain embodiments, exemplary radiation-induced damage effects can also include mucositis. In one embodiment, the radiation-induced mucositis is oral mucositis.

In certain embodiments, exemplary radiation induced effects can also include central nervous system syndrome, characterized by damage to cells that do not reproduce such as nerve cells. Exemplary symptoms include loss of coordination, confusion, coma, convulsions, shock, and the symptoms of the blood forming organ and gastrointestinal tract syndromes.

In certain embodiments, exemplary radiation induced damage effects can also include effects on the fetus due to prenatal radiation exposure. An embryo/fetus is especially sensitive to radiation, (embryo/fetus cells are rapidly dividing), particularly in the first 20 weeks of pregnancy.

In certain embodiments, exemplary radiation induced effects can also include damages due to ionizing irradiation-induced production of radical oxygen species (ROS) including superoxide, hydroxyl radical, nitric oxide and peroxynitrite from the interaction of ionizing irradiation with oxygen and water.

In one aspect, the instant disclosure provides therapeutic compositions and methods of use thereof for treating radiation induced chronic damage effects. Chronic irradiation effects are critically important in all patients, but particularly in those who receive total body irradiation (TBI). Total body irradiation is utilized in some cancer therapies particularly for patients who require a bone marrow transplant.

Exemplary radiation induced chronic damage effects can include, for example, features common to premature aging such as hair graying, skin thinning and dryness, formation of cataracts, early myocardial fibrosis, myocardial infarction, neurodegeneration, osteopenia/osteomalasia and neurocognitive defects.

In certain embodiments, exemplary radiation induced effects can also include fibrosis (the replacement of normal tissue with scar tissue, leading to restricted movement of the affected area); damage to the bowels, causing diarrhea and bleeding; memory loss; infertility and/or carcinogenesis/leukemogenesis.

In one aspect, the instant disclosure provides therapeutic compositions and methods of use thereof for treating radiation induced systemic damage effects. Exemplary systemic damage effects can include, for example, both acute and chronic effects as described above, but with several unique features. In particular, systemic effects include symptoms in areas that were not irradiated including overall tiredness and easy fatigability, and are associated with the persistent circulation of inflammatory cytokines.

In certain embodiments, systemic damage effects can include the central nervous system syndrome, nausea and vomiting, headache, sweating, rapid heart rate, gastrointestinal syndrome, destruction of intestinal crypt and endothelial cells in the intestine, dehydration, severe abdominal pain, infection, blood loss; hematopoietic syndrome; a decrease in peripheral white blood cell count, platelet count, red blood cell count, immunosuppression syndrome; decrease in peripheral blood lymphocyte count; irradiation-induced cutaneous syndrome skin burns (beta burns), erythema/redness, ulceration of the skin, heat loss, extravasation of fluids, lymphedema, hemorrhage and secondary infection.

In certain embodiments, radiation induced damage effects can include mucositis; loss of taste; xerostomia; erythema; damaged microvasculature, stem cell depletion, fibrosis, lymphedema, delayed wound healing, telangiectasis, dry mouth and ulceration.

In certain embodiments, the methods and compositions of the present disclosure are useful for treating radiation damage due to therapeutic radiation therapy, exemplary delivery modality/regimen can include, for example, conventional fractionation therapy, hyperfractionation, hypofractionation, and accelerated fractionation.

In one embodiment, the therapeutic modality/regimen is local or total skin electron beam irradiation (TSEBT) associated with CTCL treatment. In one embodiment, the electron beam irradiation is administered as high dose rate therapy (HDR). In another embodiment, the electron beam therapy is administered as low dose rate electron beam therapy.

In one embodiment, the therapeutic modality/regimen is hyperfractionation therapy. In hyperfractionation, the goal is to deliver higher tumor doses while maintaining a level of long-term tissue damage that is clinically acceptable. The daily dose is unchanged or slightly increased while the dose per fraction is decreased, and the overall treatment time remains constant.

In one embodiment, the therapeutic modality/regimen is accelerated fractionation therapy. In the accelerated fractionation therapy, the dose per fraction is unchanged while the daily dose is increased, and the total time for the treatment is reduced.

In one embodiment, the therapeutic modality/regimen is Continuous hyperfractionated accelerated radiation therapy (CHART) therapy. In (CHART) therapy, an intense schedule of treatment in which multiple daily fractions are administered within an abbreviated period.

In one embodiment, the therapeutic modality/regimen is IMRT.

Combination with Chemotherapy

A number of chemotherapeutic agents can enhance the effects of radiation therapy. In one aspect, the aspects and embodiments of the present disclosure can be utilized as a combined therapy with existing chemotherapeutic modalities. The combination (sequential or concurrent) therapy can be co-administration or co-formulation.

"Interleukin-12 (IL-12)" refers to IL-12 molecule that yields at least one of the hematopoietic properties disclosed herein, including native IL-12 molecules, variant IL-12 molecules and covalently modified IL-12 molecules, now known or to be developed in the future, produced in any manner known in the art now or to be developed in the future.

The IL-12 molecule may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 80%, 85%, or 90%, including, for example, at least about 95%, at least about 98% or at least about 99% of the peptide or dry mass of the preparation.

Generally, the amino acid sequences of the IL-12 molecule used in embodiments of the invention are derived from the specific mammal to be treated by the methods of the invention. Thus, for the sake of illustration, for humans, generally human IL-12, or recombinant human IL-12, would be administered to a human in the methods of the invention, and similarly, for felines, for example, the feline IL-12, or recombinant feline IL-12, would be administered to a feline in the methods of the invention.

Also included in the invention, however, are certain embodiments where the IL-12 molecule does not derive its amino acid sequence from the mammal that is the subject of the therapeutic methods of the invention. For the sake of illustration, human IL-12 or recombinant human IL-12 may be utilized in a feline mammal Still other embodiments of the invention include IL-12 molecules where the native amino acid sequence of IL-12 is altered from the native sequence, but the IL-12 molecule functions to yield the hematopoietic properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong S R, et al., Proc Natl Acad Sci USA. 2003 Feb. 4; 100 (3): 1163-8), where the variant IL-12 molecule is produced by a DNA shuffling method. Also included are modified IL-12 molecules are also included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. Nos. 4,640,835; 4,496,689; 4,301,144; 4,670,417;

4,791,192 or 4,179,337. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Both native sequence IL-12 and amino acid sequence variants of IL-12 may be covalently modified. Also as referred to herein, the IL-12 molecule can be produced by various methods known in the art, including recombinant methods. Other IL-12 variants included in the present disclosure are those where the canonical sequence is post-translationally-modified, for example, glycosylated. In certain embodiments, the IL-12 is expressed in a mammalian expression system or cell line. In one embodiment, the IL-12 is produced by expression in Chinese Hamster Ovary (CHO) cells.

Since it is often difficult to predict in advance the characteristics of a variant IL-12 polypeptide, it will be appreciated that some screening of the recovered variant will be needed to select the optimal variant. A preferred method of assessing a change in the hematological stimulating or enhancing properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

For general descriptions relating IL-12, see U.S. Pat. Nos. 5,573,764, 5,648,072, 5,648,467, 5,744,132, 5,756,085, 5,853,714 and 6,683,046. Interleukin-12 (IL-12) is a heterodimeric cytokine generally described as a proinflammatory cytokine that regulates the activity of cells involved in the immune response (Fitz K M, et al., 1989, J. Exp. Med. 170:827-45). Generally IL-12 stimulates the production of interferon-$\gamma$ (INF-$\gamma$) from natural killer (NK) cells and T cells (Lertmemongkolchai G, Cai et al., 2001, Journal of Immunology. 166:1097-105; Cui J, Shin T, et al., 1997, Science. 278:1623-6; Ohteki T, Fukao T, et al., 1999, J. Exp. Med. 189:1981-6; Airoldi I, Gri G, et al., 2000, Journal of Immunology. 165:6880-8), favors the differentiation of T helper 1 (TH1) cells (Hsieh C S, et al., 1993, Science. 260:547-9; Manetti R, et al., 1993, J. Exp. Med. 177:1199-1204), and forms a link between innate resistance and adaptive immunity. IL-12 has also been shown to inhibit cancer growth via its immuno-modulatory and anti-angiogenesis effects (Brunda M J, et al., 1993, J. Exp. Med. 178:1223-1230; Noguchi Y, et al., 1996, Proc. Natl. Acad. Sci. U.S.A. 93:11798-11801; Giordano P N, et al., 2001, J. Exp. Med. 194:1195-1206; Colombo M P, et al., 2002, Cytokine Growth factor rev. 13:155-168; Yao L, et al., 2000, Blood 96:1900-1905). IL-12 is produced mainly by dendritic cells (DC) and phagocytes (macrophages and neutrophils) once they are activated by encountering pathogenic bacteria, fungi or intracellular parasites (Reis C, et al., 1997, J. Exp. Med. 186:1819-1829; Gazzinelli R T, et al., 1994, J. Immunol. 153:2533-2543; Dalod M, et al., 2002, J. Exp. Med. 195:517-528). The IL-12 receptor (IL-12 R) is expressed mainly by activated T cells and NK cells (Presky D H, et al., 1996, Proc. Natl. Acad. Sci. U.S.A. 93:14002-14007; Wu C Y, et al., 1996, Eur J. Immunol. 26:345-50).

Generally the production of IL-12 stimulates the production of INF-$\gamma$, which, in turn, enhances the production of IL-12, thus forming a positive feedback loop. In in vitro systems, it has been reported that IL-12 can synergize with other cytokines (IL-3 and SCF for example) to stimulate the proliferation and differentiation of early hematopoietic progenitors (Jacobsen S E, et al., 1993, J. Exp Med 2: 413-8; Ploemacher R E, et al., 1993, Leukemia 7: 1381-8; Hirao A, et al., 1995, Stem Cells 13: 47-53).

In vivo administration of IL-12 was observed to decrease peripheral blood cell counts and bone marrow hematopoiesis (Robertson M J, et al., 1999, Clinical Cancer Research 5: 9-16; Lenzi R, et al., 2002, Clinical Cancer Research 8:3686-95; Ryffel B. 1997, Clin Immunol Immunopathol. 83:18-20; Car B D, et al., 1999, The Toxicol Pathol. 27:58-63). Using INF-$\gamma$ receptor knockout mice, Eng et al and Car et al demonstrated that high dose IL-12 did not induce the commonly seen toxicity effect, i.e., there was no inhibition of hematopoiesis (Eng V M, et al., 1995, J. Exp Med. 181:1893-8; Car B D, et al., 1995, American Journal of Pathology 147:1693-707). This observation suggests that the general phenomenon of IL-12 facilitated enhancement of differentiated hematopoietic cells, as reported previously, may be balanced in vivo by the production of INF-$\gamma$, which acts in a dominant myelo-suppressive fashion.

Figure 14:
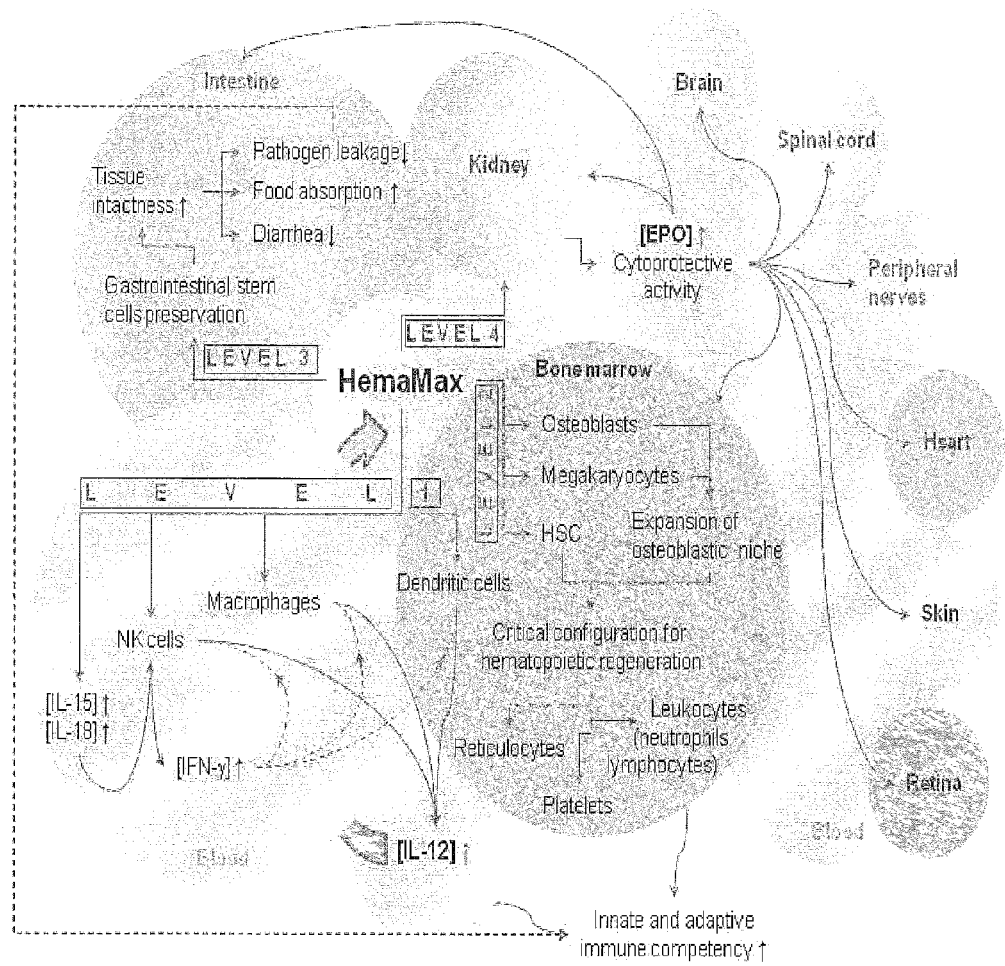
FIG. 14. AL Multilevel Model Of Recombinant Human IL-12 Mechanism Of Action In Increasing Survival Following Exposure To Radiation. Current evidence suggests that recombinant human IL-12 triggers responses in, at least, four levels in the body. At the Level 1 response, recombinant human IL-12 promotes proliferation and activation of extant, radiosensitive immune cells, namely NK cells, macrophages, and dendritic cells. Recombinant human IL-12-induced plasma elevations of IL-15 and IL-18 also facilitate maturation of NK cells, leading to the release of IFN-γ, which in turn, positively affects the production of endogenous IL-12 from macrophages and dendritic cells, and perhaps NK cells. These events enhance the innate immune competency early on following recombinant human IL-12 administration. At the Level 2 response, recombinant human IL-12 promotes proliferation and differentiation of the surviving hematopoietic stem cells, osteoblasts, and megakaryocytes into a specific cellular configuration that ensues optimal hematopoiesis. Recombinant human IL-12-induced secretion of EPO from CD34+, IL-12Rβ2-positive bone marrow cells may also suppress local over-production of IFN-γ in the bone marrow and, thus, provide a milieu that promotes expansion of hematopoietic cells. Hematopoietic regeneration in the bone marrow enhances both innate and adaptive immune competency. At the Level 3 response, recombinant human IL-12 preserves GI stem cells, leading to a reduction in pathogen leakage, an increase in food consumption, and a decrease in diarrhea. At the Level 4 response, recombinant human IL-12 likely directly increases renal release of EPO, a cytoprotective factor, which enhances cellular viability in a diverse set of organs/tissues. Continued production of endogenous IL-12 primarily from dendritic cells activated by pathogens and/or EPO serves as a positive feedback loop and plays a key role in sustaining the initial response to exogenous recombinant human IL-12, perhaps for weeks after radiation. ↑=increase; ↓=decrease; HSC=Hematopoietic stem cells; NK cells=natural killer cells.

Current evidence suggests that an exemplary IL-12 preparation, a recombinant human IL-12 (e.g., recombinant human IL-12), triggers responses at, at least, 4 levels in the body (see FIG. 14). At the Level 1 response, recombinant human IL-12 promotes proliferation and activation of extant, radiosensitive immune cells, namely NK cells, macrophages, and dendritic cells. Recombinant human IL-12-induced plasma elevations of IL-15 and IL-18 also facilitate maturation of NK cells, leading to the release of IFN-$\gamma$, which in turn, positively affects the production of endogenous IL-12 from macrophages and dendritic cells, and perhaps NK cells. These events enhance the innate immune competency early on following recombinant human IL-12 administration. At the Level 2 response, recombinant human IL-12 promotes proliferation and differentiation of the surviving hematopoietic stem cells, osteoblasts, and megakaryocytes into a specific cellular configuration that ensues optimal hematopoiesis. Recombinant human IL-12-induced secretion of EPO from CD34+, IL-12R$\beta$2-positive bone marrow cells may also suppress local over-production of IFN-$\gamma$ in the bone marrow and, thus, provide a milieu that promotes expansion of hematopoietic cells. Hematopoietic regeneration in the bone marrow enhances both innate and adaptive immune competency. At the Level 3 response, recombinant human IL-12 preserves GI stem cells, leading to a reduction in pathogen leakage, an increase in food consumption, and a decrease in diarrhea. At the Level 4 response, recombinant human IL-12 likely directly increases renal release of EPO, a cytoprotective factor, which enhances cellular viability in a diverse set of organs/tissues. Continued production of endogenous IL-12 primarily from dendritic cells activated by pathogens and/or EPO serves as a positive feedback loop and plays a key role in sustaining the initial response to exogenous recombinant human IL-12, perhaps for weeks after radiation.

Methods of Administration of IL-12

The instant disclosure provides methods of treatment by administration to a subject of one or more effective dose(s) of IL-12 for a duration to achieve the desired therapeutic effect. The subject is preferably a mammal, including, but not limited to, animals such as cows, pigs, horses, chickens, cats, dogs, etc., and is most preferably human.

Various delivery systems are known and can be used to administer IL-12 in accordance with the methods of the invention, e.g., encapsulation in liposomes, microparticles, microcapsules, recombinant cells capable of expressing IL-12, receptor-mediated endocytosis (see, e.g., Wu and Wu, 1987, J. Biol. Chem. 262:4429-4432), construction of nucleic acid comprising a gene for IL-12 as part of a retroviral or other vector, etc. Methods of introduction include but are not limited to topical, subcutaneous, intradermal, intramuscular, intraperitoneal, intravenous, subcutaneous, intranasal, epidural, and oral routes. For treatment of CTCL, topical, subcutaneous, intradermal, and systemic deliveries can be particularly efficacious.

IL-12 can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce pharmaceutical compositions comprising IL-12 into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising IL-12 locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as Silastic™ membranes, or fibers.

Other modes of IL-12 administration involve delivery in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

Still other modes of administration of IL-12 involve delivery in a controlled release system. In certain embodiments, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Forms and Dosages of IL-12

As used herein, for CTCL treatment, lyophilized formulation and liquid formulation suitable for injection are particularly efficacious. Suitable dosage forms of IL-12 for use in embodiments of the present invention encompass physiologically/pharmaceutically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, P6N (Neumedicines, Pasadena, Calif.) and PEG. Carriers for topical or gel-based forms of IL-12 polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nanocapsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and gamma-ethyl-L-glutamate (Sidman et al., supra), non-degradable ethylene-vinyl acetate (Langer et al, supra), degradable lactic acid-glycolic acid copolymers such as the Lupron Depot™ (injectable microspheres composed of lactic acid-glycolicacid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated IL-12 polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release IL-12 containing compositions also include liposomally entrapped polypeptides. Liposomes containing a IL-12 polypeptide are prepared by methods known in the art, such as described in Eppstein et al., Proc. Natl. Acad. Sci. USA 82:3688-3692 (1985); Hwang et al., Proc. Natl. Acad. Sci. USA 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal Wnt polypeptide therapy. Liposomes with enhanced circulation time are disclosed in U.S. Pat. No. 5,013,556.

For the treatment of disease, the appropriate dosage of a IL-12 polypeptide will depend on the type of disease to be treated, as defined above, the severity and course of the disease, previous therapy, the patient's clinical history and response to the IL-12 therapeutic methods disclosed herein, and the discretion of the attending physician. In accordance with the invention, IL-12 is suitably administered to the patient at one time or over a series of treatments.

Depending on the type and severity of the disease, about 10 ng/kg to 2000 ng/kg of IL-12 is an initial candidate dosage for administration to the patient, whether, for example, by one or more separate administrations, or by continuous infusion. Humans can safely tolerate a repeated dosages of about 500 ng/kg, but single dosages of up to about 200 ng/kg should not produce toxic side effects. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

IL-12 may be administered along with other cytokines, either by direct co-administration or sequential administration. When one or more cytokines are co-administered with IL-12, lesser doses of IL-12 may be employed. Suitable doses of other cytokines, i.e. other than IL-12, are from about 1 ug/kg to about 15 mg/kg of cytokine. For example, the dose may be the same as that for other cytokines such as G-CSF, GM-CSF and EPO. The other cytokine(s) may be administered prior to, simultaneously with, or following administration of IL-12. The cytokine(s) and IL-12 may be combined to form a pharmaceutically composition for simultaneous administration to the mammal. In certain embodiments, the amounts of IL-12 and cytokine are such that a synergistic repopulation of blood cells (or synergistic increase in proliferation and/or differentiation of hematopoietic cells) occurs in the mammal upon administration of IL-12 and other cytokine thereto. In other words, the coordinated action of the two or more agents (i.e. the 11-12 and one or more cytokine(s)) with respect to repopulation of blood cells (or proliferation/differentiation of hematopoietic cells) is greater than the sum of the individual effects of these molecules.

Therapeutic formulations of IL-12 are prepared for storage by mixing IL-12 having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween®, Pluronics™ or polyethylene glycol (PEG).

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers include but are not limited to histidine-buffers, citrate-buffers, succinate-buffers, acetate-buffers, phosphate-buffers, arginine-buffers or mixtures thereof. The above-mentioned buffers are generally used in an amount of about 1 mM to about 100 mM, of about 5 mM to about 50 mM and of about 10-20 mM. The pH of the buffered solution can be at least 4.0, at least 4.5, at least 5.0, at least 5.5 or at least 6.0. The pH of the buffered solution can be less than 7.5, less than 7.0, or less than 6.5. The pH of the buffered solution can be about 4.0 to about 7.5, about 5.5 to about 7.5, about 5.0 to about 6.5, and about 5.5 to about 6.5 with an acid or a base known in the art, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect protein formulations against mechanical stresses like agitation and shearing. Examples of pharmaceutically acceptable surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esthers are sold under the tradename Triton-X. When polysorbate 20 (Tween 20®) and polysorbate 80 (Tween 80®) are used they are generally used in a concentration range of about 0.001 to about 1%, of about 0.005 to about 0.2% and of about 0.01% to about 0.1% w/v (weight/volume).

As used herein, the term "stabilizer" can include a pharmaceutical acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., Crit. Rev. Ther. Drug Carrier Syst., 70(4):307-77 (1993); Wang, Int. J. Pharm., 7S5(2): 129-88 (1999); Wang, Int. J. Pharm., 203(1-2): 1-60 (2000); and Chi et al., Pharm. Res., 20(9): 1325-36 (2003). Stabilizers include but are not limited to sugars, amino acids, polyols, cyclodextrines, e.g. hydroxypropyl-beta-cyclodextrine, sulfobutylethyl-beta-cyclodextrin, beta-cyclodextrin, polyethylenglycols, e.g. PEG 3000, PEG 3350, PEG 4000, PEG 6000, albumine, human serum albumin (HSA), bovine serum albumin (BSA), salts, e.g. sodium chloride, magnesium chloride, calcium chloride, chelators, e.g. EDTA as hereafter defined. As mentioned hereinabove, stabilizers can be present in the formulation in an amount of about 10 to about 500 mM, an amount of about 10 to about 300 mM, or in an amount of about 100 mM to about 300 mM. In some embodiments, exemplary IL-12 can be dissolved in an appropriate pharmaceutical formulation wherein it is stable.

IL-12 also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

IL-12 to be used for in vivo administration must be sterile. This is readily accomplished by filtration through sterile filtration membranes, prior to or following lyophilization and reconstitution. IL-12 ordinarily will be stored in lyophilized form or in solution. Therapeutic IL-12 compositions generally are placed into a container having a sterile access port, for example, an intravenous solution bag or vial having a stopper pierceable by a hypodermic injection needle.

When applied topically, IL-12 is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, IL-12 formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the IL-12 molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and IL-12 is present in an amount of about 300-1000 mg per ml of gel.

An effective amount of IL-12 to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer IL-12 until a dosage is reached that achieves the desired effect. A typical dosage for systemic treatment might range from about 10 ng/kg to up to 2000 ng/kg or more, depending on the factors mentioned above. In some embodiments, the dose ranges can be from about 1, 2, 3, 4, 5, 6, 7, 8, 9, 10, 11, 12, 13, 14, 15, 16, 17, 18, 19 to about 20; to about 30; to about 50; to about 100, to about 200, to about 300 or to about 500 ng/kg. In one aspect, the dose is less than 500 ng/kg, In another aspect, the dose is less than 300 ng/kg. In another aspect, the dose is less than about 200 ng/kg. In another aspect, the dose is less than about 100 ng/kg. In another aspect, the dose is less than about 50 ng/kg. In other aspects, the dose can range from about 10 to 300 ng/kg, 20 to 40 ng/kg, 25 to 35 ng/kg, 50 to 100 ng/kg. In certain embodiments, the appropriate dosing can be determined based on an amount of IL-12 administered per surface area of the affected region.

In one aspect, exemplary therapeutic compositions described herein can be administered in combination with fractionation therapy. In one embodiment, the therapeutically effective dose is given before each fraction. In one embodiment, the therapeutically effective dose is given at about the same time as the administration of each fraction. In one embodiment, the therapeutically effective dose is given before each fraction, ranging from 5, 10, 15, 20, 25, 30, 35, 40 50, or 60 minutes before each fraction; or 2, 3, 4, 5, 6, 7, 8, 9, 10, 11, 12 hours after each fraction; or 1, 2, 3, 4, 5, 6, 7 days before each fraction. In one embodiment, the therapeutically effective dose is given after each fraction, ranging from 5, 10, 15, 20, 25, 30, 35, 40 50, or 60 minutes after each fraction; or 2, 3, 4, 5, 6, 7, 8, 9, 10, 11, 12 hours after each fraction; or 1, 2, 3, 4, 5, 6, 7 days after each fraction; or once, twice, three times, 4 times, 5 times, 6 times, 7 times weekly, biweekly, or bimonthly, during or after the radiation treatment. In another embodiment, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days both before and after each radiation dose in fractionated regimens of 1 to 10 doses/day for up to 30 days, administered either as TBI or locally, using each respective radiation source.

As an alternative general proposition, the IL-12 receptor is formulated and delivered to the target site or tissue at a dosage capable of establishing in the tissue an IL-12 level greater than about 0.1 ng/cc up to a maximum dose that is efficacious but not unduly toxic. This intra-tissue concentration should be maintained if possible by the administration regime, including by continuous infusion, sustained release, topical application, or injection at empirically determined frequencies. The progress of this therapy is easily monitored by conventional assays.

"Near the time of administration of the treatment" refers to the administration of IL-12 at any reasonable time period either before and/or after the administration of the treatment, such as about one month, about three weeks, about two weeks, about one week, several days, about 120 hours, about 96 hours, about 72 hours, about 48 hours, about 24 hours, about 20 hours, several hours, about one hour or minutes. Near the time of administration of the treatment may also refer to either the simultaneous or near simultaneous administration of the treatment and IL-12, i.e., within minutes to one day.

"Chemotherapy" refers to any therapy that includes natural or synthetic agents now known or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil for patients with locally advanced squamous cell carcinoma of the head (Tsukuda, M. et al., Int J Clin Oncol. 2004 June; 9 (3): 161-6), and fludarabine and bendamustine in refractory and relapsed indolent lymphoma (Konigsmann M, et al., Leuk Lymphoma. 2004; 45 (9): 1821-1827).

As used herein, exemplary sources of therapeutic or accidental ionizing radiation can include, for example, alpha, beta, gamma, x-ray, and neutron sources.

"Radiation therapy" refers to any therapy where any form of radiation is used to treat the disease state. The instruments that produce the radiation for the radiation therapy are either those instruments currently available or to be available in the future.

"High dose treatment modalities" refer to treatments that are high sub-lethal or near lethal. High dose treatment modalities are intended to have an increased ability to achieve therapeutic endpoint, but generally possess increased associated toxicities. Further, generally high dose treatment modalities exhibit increased hematopoietic damage, as compared with conventional treatment modalities. The protocols for high dose treatment modalities are those currently used or to be used in the future.

As used herein, radiation therapy "treatment modality" can include both ionizing and non-ionizing radiation sources. Exemplary ionizing radiation treatment modality can include, for example, external beam radiotherapy; Intensity modulated radiation therapy (IMRT); Image Guided Radiotherapy (IGRT); X Irradiation (e.g. photon beam therapy); electron beam (e.g. beta irradiation); local and total skin electron beam therapy; mega voltage photon treatment (about 4 to 10 MeV); proton irradiation; high linear energy transfer (LET) particles; stereotactic radiosurgery; gamma knife; linear accelerator mediated frameless stereotactic radiosurgery; robot arm controlled x irradiation delivery system; radioisotope radiotherapy for organ specific or cancer cell specific uptake; radioisotope bound to monoclonal antibody for tumor targeted radiotherapy (or radioimmunotherapy, RIT); brachytherapy (interstitial or intracavity) high dose rate radiation source implantation; permanent radioactive seed implantation for organ specific dose delivery.

"A dose dense treatment regimen" is generally a treatment regimen whereby the treatment is repeated sequentially in an accelerated manner to achieve the desired treatment outcome, as compared with conventional treatment regimens. The methods of the invention facilitate the use of dose dense treatment regimens by reducing or ameliorating the associated hematopoietic toxicities of the treatment, thereby permitting dose dense treatment regimens to be utilized and increasing the rate of success in treating a particular disease state. (see generally, Hudis C A, Schmits N, Semin Oncol. 2004 June; 31 (3 Suppl 8): 19-26; Keith B et al., J Clin Oncol. 2004 Feb. 15; 22 (4): 749; author reply 751-3; Maurel J et al., Cancer. 2004 Apr. 1; 100 (7): 1498-506; Atkins C D, J Clin Oncol. 2004 Feb. 15; 22 (4): 749-50.)

"Chemoprotection or radioprotection" refers to protection from, or an apparent decrease in, the associated hematopoietic toxicity of a treatment intended to target the disease state.

As used herein, "Acute Radiation Syndrome (ARS) (also known as radiation toxicity or radiation sickness), is characterized by an acute illness caused by receiving lethal or sublethal irradiation of the entire body (or most of the body) by a high dose of penetrating radiation in a very short period of time (e.g. a matter of minutes). Examples of people who suffered from ARS are the survivors of the Hiroshima and Nagasaki atomic bombs, the firefighters that first responded after the Chernobyl Nuclear Power Plant event in 1986, and some unintentional exposures to sterilization irradiators. In certain embodiments, the radiation dose associated with acute radiation syndrome is usually large (i.e., greater than 0.7 Gray (Gy) or 70 rads). In certain embodiments, mild symptoms may be observed with doses as low as 0.3 Gy or 30 rads.

As used herein, "acute damage effects" and "damage effects" can include radiation induced damage due to acute lethal and near lethal radiation dose.

In some embodiments, exemplary Acute Radiation Syndrome may include the following three syndromes: 1) Bone marrow syndrome (sometimes referred to as hematopoietic syndrome) the full syndrome will usually occur with a dose between 0.7 and 10 Gy (70-1000 rads) though mild symptoms may occur as low as 0.3 Gy or 30 rads. The survival rate of patients with this syndrome decreases with increasing dose. The primary cause of death is the destruction of the bone marrow, resulting in infection and hemorrhage; 2) Gastrointestinal (GI) syndrome: the full syndrome will usually occur with a dose greater than approximately 10 Gy (1000 rads) although some symptoms may occur as low as 6 Gy or 600 rads. Survival is extremely unlikely with this syndrome. Destructive and irreparable changes in the GI tract and bone marrow usually cause infection, dehydration, and electrolyte imbalance. Death usually occurs within 2 weeks; and 3) Cardiovascular (CV)/Central Nervous System (CNS) syndrome: the full syndrome will usually occur with a dose greater than approximately 50 Gy (5000 rads) although some symptoms may occur as low as 20 Gy or 2000 rads. Death occurs within 3 days. Death likely is due to collapse of the circulatory system as well as increased pressure in the confining cranial vault as the result of increased fluid content caused by edema, vasculitis, and meningitis.

In some embodiments, exemplary Acute Radiation Syndrome can include the following four stages: 1) prodromal stage (N-V-D stage): the classic symptoms for this stage are nausea, vomiting, as well as anorexia and possibly diarrhea (depending on dose), which occur from minutes to days following exposure. The symptoms may last (episodically) for minutes up to several days; 2) Latent stage: the patient looks and feels generally healthy for a few hours or even up to a few weeks; 3) manifest illness stage: the symptoms depend on the specific syndrome (see Table A) and last from hours up to several months; and 4) Recovery or death: most patients who do not recover will die within several months of exposure. The recovery process can lasts from about several weeks to up to about two years. Center for Disease Control and Prevention Fact Sheet for Physicians, Acute Radiation Syndrome; Radiation Studies Branch (RSB), Division of Environmental Hazards and Health Effects (EHHE), National Center for Environmental Health (NCEH), Coordinating Center for Environmental Health and Injury Prevention (CCEHIP); 2005.

TABLE A

Acute Radiation Syndromes

| Syndrome | Dose | Prodromal Stage | Latent Stage | Manifest Illness Stage | Recovery |
|---|---|---|---|---|---|
| Hematopoietic (Bone Marrow) | >0.7 Gy (>70 rads) (mild symptoms may occur as low as 0.3 Gy or 30 rads) | Symptoms are anorexia, nausea and vomiting. Onset occurs 1 hour to 2 days after exposure. Stage lasts for minutes to days. | Stem cells in bone marrow are dying, although patient may appear and feel well. Stage lasts 1 to 6 weeks. | Symptoms are anorexia, fever, and malaise. Drop in all blood cell counts occurs for several weeks. Primary cause of death is infection and hemorrhage. Survival decreases with increasing dose. Most deaths occur within a few months after exposure. | in most cases, bone marrow cells will begin to repopulate the marrow. There should be full recovery for a large percentage of individuals from a few weeks up to two years after exposure. death may occur in some individuals at 1.2 Gy (120 rads). the LD50/60[†] is about 2.5 to 5 Gy (250 to 500 rads) |
| Gastrointestinal (GI) | >10 Gy (>1000 rads) (some symptoms may occur as low as 6 Gy or 600 rads) | Symptoms are anorexia, severe nausea, vomiting, cramps, and diarrhea. Onset occurs within a few hours after exposure. Stage lasts about 2 days. | Stem cells in bone marrow and cells lining GI tract are dying, although patient may appear and feel well. Stage lasts less than 1 week. | Symptoms are malaise, anorexia, severe diarrhea, fever, dehydration, and electrolyte imbalance. Death is due to infection, dehydration, and electrolyte imbalance. Death occurs within 2 weeks of exposure. | the LD100 is about 10 Gy (1000 rads) |
| Cardiovascular (CV)/ Central Nervous System (CNS) | >50 Gy (5000 rads) (some symptoms may occur as low as 20 Gy or 2000 rads) | Symptoms are extreme nervousness and confusion; severe nausea, vomiting, and watery diarrhea; loss of consciousness; and burning sensations of the skin. Onset occurs within minutes of exposure. Stage lasts for minutes to hours. | Patient may return to partial functionality. Stage may last for hours but often is less. | Symptoms are return of watery diarrhea, convulsions, and coma. Onset occurs 5 to 6 hours after exposure. Death occurs within 3 days of exposure. | No recovery is expected |

"Solid tumors" generally refers to the presence of cancer of body tissues other than blood, bone marrow, or the lymphatic system.

"Hematopoietic disorders (cancers)" generally refers to the presence of cancerous cells originated from hematopoietic system.

"Ameliorate the deficiency" refers to a reduction in the hematopoietic deficiency, i.e., an improvement in the deficiency, or a restoration, partially or complete, of the normal state as defined by currently medical practice. Thus, amelioration of the hematopoitic deficiency refers to an increase in, a stimulation, an enhancement or promotion of, hematopoiesis generally or specifically. Amelioration of the hematopoietic deficiency can be observed to be general, i.e., to increase two or more hematopoietic cell types or lineages, or specific, i.e., to increase one hematopoietic cell type or lineages.

"Bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, supporting cells (stromal cells), including but not limited to the associated stem and/or progenitor cells for these and other cell types and lineages.

"Hematopoietic cell type" generally refers to differentiated hematopoietic cells of various types, but can also include the hematopoietic progenitor cells from which the particular hematopoietic cell types originate from, such as various blast cells referring to all the cell types related to blood cell production, including stem cells, progenitor cells, and various lineage cells, such as myeloid cells, lymphoid cell, etc.

"Hematopoietic cell lineage" generally refers to a particular lineage of differentiated hematopoietic cells, such as myeloid or lymphoid., but could also refer to more differentiated lineages such as dendritic, erythroid, etc.

"IL-12 facilitated proliferation" of cells refers to an increase, a stimulation, or an enhancement of hematopoiesis that at least partially attributed to an expansion, or increase, in cells that generally reside or home to the bone marrow of a mammal, such as hematopoietic progenitor and/or stem cells, but includes other cells that comprise the microenviroment of the bone marrow niche.

"Stimulation or enhancement of hematopoiesis" generally refers to an increase in one or more hematopoietic cell types or lineages, and especially relates to a stimulation or enhancement of one or more hematopoietic cell types or lineages in cases where a mammal has a deficiency in one or more hematopoietic cell types or lineages.

"Hematopoietic long-term repopulating cells" are generally the most primitive blood cells in the bone marrow; they are the blood stem cells that are responsible for providing life-long production of the various blood cell types and lineages.

"Hematopoietic stem cells" are generally the blood stem cells; there are two types: "long-term repopulating" as defined above, and "short-term repopulating" which can produce "progenitor cells" for a short period (weeks, months or even sometimes years depending on the mammal).

"Hematopoietic progenitor cells" are generally the first cells to differentiate from (i.e., mature from) blood stem cells; they then differentiate (mature) into the various blood cell types and lineages.

"Hematopoietic support cells" are the non-blood cells of the bone marrow; these cells provide "support" for blood cell production. These cells are also referred to as bone marrow stromal cells.

"Bone marrow preservation" means the process whereby bone marrow that has been damaged by radiation, chemotherapy, disease or toxins is maintained at its normal, or near normal, state; "bone marrow recovery" means the process whereby bone marrow that has been damaged by radiation, chemotherapy, disease or toxins is restored to its normal, near normal state, or where any measurable improvement in bone marrow function are obtained; bone marrow function is the process whereby appropriate levels of the various blood cell types or lineages are produced from the hematopoietic (blood) stem cells.

"Bone marrow failure" is the pathologic process where bone marrow that has been damaged by radiation, chemotherapy, disease or toxins is not able to be restored to normal and, therefore, fails to produce sufficient blood cells to maintain proper hematopoiesis in the mammal

EXAMPLES

The invention is now described with reference to the following Examples. These Examples are provided for the purpose of illustration only, and the invention is not limited to these Examples, but rather encompasses all variations that are evident as a result of the teaching provided herein.

Prior to the experiments described herein, there were no published protocol that allows for compositions and methods comprising IL-12, including therapeutically effective recombinant human interleukin-12 (IL-12) preparation for treating radiation induced damage effects, including acute radiation syndrome in a subject and/or radiation induced cytotoxicity associated with local and/or total skin electron beam therapy in the treatment of CTCL.

Aspects and embodiments of the instant disclosure stem from the unexpected discovery that certain IL-12 formulations have surprising and unexpected utility and efficacy when administered to a subject following exposure to acute radiation exposure, including exposure associated with local and total skin electron beam therapy. The therapeutic compositions provide potent mitigation of radiation injury to multiple tissues, including the immune, bone marrow, and GI compartments, leading to significant increases in survival and/or mitigation of radiation-induced cytotoxicity associated with CTCL therapy.

By way of example, a method to prepare therapeutically effective radioprotective IL-12 formulation was developed.

Example 1

Exemplary Recombinant Murine IL-12 and Exemplary Recombinant Human IL-12

Exemplary recombinant murine IL-12 (e.g. any suitable recombinant-murine IL-12 preparation, including, for example, a glycosylated version of recombinant murine IL-12 produced in CHO cells; hereinafter "recombinant murine IL-12) was obtained from Peprotech (Rocky Hill, N.J., USA) or provided by SBH Sciences (Natick, Mass., USA) exclusively to Neumedicines. Exemplary recombinant human IL-12, rHuIL-12 (e.g. any suitable recombinant-human IL-12 preparation, including, for example, a glycosylated version of recombinant human IL-12 produced in CHO cells; hereinafter "recombinant human IL-12") was provided by SBH Sciences (Natick, Mass., USA) to Neumedicines. In the initial mouse survival studies, lyophilized exemplary murine recombinant IL-12 (e.g. recombinant murine IL-12) was dissolved in phosphate buffer saline (PBS), pH=7.2. In all other studies, exemplary murine recombinant IL-12 (e.g. recombinant murine IL-12 and exemplary recombinant human IL-12 (e.g. recombinant human IL-12) were dissolved in a trehalose formulation (P5.6TT). In these embodiments, the recipe for the trehalose formulation is as follows: formulation Recipe for 200 mL: 186 mL of dH20, 12 g of Trehalose, 1.6 mL of 5% Tween 20, 1.0 g of Sodium Phosphate Monobasic Anhydrous, 0.24 g of Sodium Phosphate Dibasic Anhydrous, adjust to pH 5.6 with 12.1 M HCL. Studies in mice and rhesus monkeys utilized recombinant murine IL-12 and recombinant human IL-12, respectively. PBS was used as vehicle in the initial mouse survival studies as indicated. P5.6TT was used as vehicle in all other studies.

Example 2

Survival Studies

Mouse survival studies were carried out at either BATTS Laboratories (Northridge, Calif., USA; HHS OLAW A4475-01) or the Roy E. Coats Research Laboratories (University of California, Los Angeles, Calif., USA; HHS OLAW A3196-01). Mouse bone marrow isolations were carried out at BATTS Laboratories. Female C57BL/6 mice were obtained from The Jackson Laboratory (Sacramento, Calif., USA), and male mice from Harlan Laboratories (Placentia, Calif., USA), or were bred at the Roy E. Coats Research Laboratories (Coats mice). Coats mice are gnobiotic, and consequently have are less radiosensitive than the Harlan mice. Differences in radiation doses in experiments using the different mice consequently differed with higher radiation amounts used in the Coats mice experiments. Coats mice exposed to radiation doses of 8.6, 8.8 and 9.0 Gy in these studies whereas Harlan mice were subjected to 8 Gy unless otherwise specified. Mouse pharmacokinetic (PK) and pharmacodynamic (PD) studies and gastrointestinal (GI) tissue isolations were carried out at LAB Research, Inc. (Laval, Québec, Canada; HHS OLAW A5525-01). Male C57BL/6 mice were obtained from Charles River Canada, Inc. (Saint-Constant, Québec, Canada). In PK/PD studies involving radiation Charles River mice were subjected to 8.6 Gy TBI (LD100/30). At all study sites, mice were maintained in quarantine for at least one week. Mice used in the survival and PK/PD studies were 9 weeks to 10 weeks old and weighed approximately 20 g with no signs of disease.

Survival Assessment

At day 0, TBI was carried out at a lethal dose of 8.0 Gy (Harlan mice) or 9.0 Gy (Coats mice)—doses that are expected to cause death in about 90% of animals within 30 days—using Gammacell® 40 with 137Cs source (Theratronics, Ontario Canada with a rate of 71 cGy/min in Coats mice studies and 85 cGy/min in the Harlan mice studies) in a specially constructed "pie-box" designed to keep mice in the center of the irradiator for even distribution of radiation. Mice received subcutaneous injections of either vehicle or recombinant murine IL-12 at the indicated doses at 24 hours, 48 hours, and/or 72 hours after irradiation. Mice were monitored for survival up to day 30. During this period, mice were deprived of all supportive care, including antibiotics, to increase the stringency of the survival protocol. The mice had access to food and acidified water ad libitum.

Radiation dose dependency of the recombinant murine IL-12 effect was evaluated in mice (n=10 per group; Coats mice), which were irradiated at lethal doses of about 8.6 Gy, 8.8 Gy, and 9.0 Gy, which resulted in LD70/30, LD90/30, and LD100/30, respectively. Animals received vehicle or recombinant murine IL-12 at a dose of 20 ng/mouse 24 hours after TBI. Mice were monitored for survival up to day 30. No supportive care, including antibiotics, was allowed during this period. The mice had access to food and acidified water ad libitum.

Example 3

Plasma PK and PD of Recombinant Murine IL-12 in Irradiated and Non-Irradiated Subjects By way of example, a method for assessing Plasma PK and PD of recombinant murine IL-12 in Irradiated and Non-Irradiated subjects was developed.

Mice (n=3 per group) received recombinant murine IL-12 subcutaneously at a dose of 10 ng/mouse, 20 ng/mouse, 40 ng/mouse, or 200 ng/mouse either in the absence of irradiation or 24 hours after an LD100/30 (8.6 Gy; Charles River mice) of TBI. Two additional control groups of animals (n=3 per group), which did not receive recombinant murine IL-12, were either not exposed to radiation or irradiated at 8.6 Gy. The concentrations of recombinant murine IL-12 and IFN-γ were determined in plasma from blood samples withdrawn at 45 minutes and 1.5, 3, 6, 12, 24, 48 and 72 hours after recombinant murine IL-12 administration by enzyme-linked immunosorbent assay (ELISA). Plasma erythropoietin (EPO) levels were measured only at the 12 hour timepoint because of limited sample availability.

Example 4

Bone Marrow and GI Histopathology

By way of example, a method for assessing Bone Marrow and GI histopathology was developed.

For bone marrow histopathology studies, mice (n=2 per group) were subjected to TBI at 8.0 Gy (Harlan mice, ~LD40/30 in this experiment) and were subsequently administered either vehicle (P5.6TT) or recombinant murine IL-12 (20 ng/mouse) subcutaneously at either (a) 24 hours, (b) 24 hours and 2 days, (c) 24 hours and 3 days, (d) 24 hours and 4 days, or (e) 24 hours and 5 days after irradiation. An additional group of mice (n=2) received recombinant human IL-12 at 24 hours after TBI. Mice were sacrificed 12 days after irradiation, and femoral bone marrow was provided as paraffin-embedded, sectioned tissues by Cyto-Pathology Diagnostic Center, Inc (Duarte, Calif., USA).

For GI histopathology studies, mice (n=3 per group) received vehicle (P5.6TT) or recombinant murine IL-12 subcutaneously at doses from 10 ng/mouse to 200 ng/mouse either in the absence of irradiation or 24 hours after a TBI at 8.6 Gy (Charles River mice, LD100/30). Mice were sacrificed 3 days after irradiation, and jejunum was provided as paraffin-embedded, sectioned tissues by Cytopathology Diagnostics Center, Inc. (Duarte, Calif., USA).

Sectioned tissues were deparaffinized with xylene, rehydrated with decreasing concentrations of ethanol, and subjected to the heat-induced epitope retrieval (HIER) to recover antigens. Endogenous peroxidase was inhibited with 0.3% H2O2, and background staining was blocked with the Background Sniper (Biocare Medical, LLC.; Concord, Calif.).

In the bone marrow histopathology studies, tissue sections were incubated with either rabbit anti-mouse IL-12 receptor beta 2 subunit (IL-12R β 2) (Sigma; St Louis, Mo.), rabbit anti-mouse osteocalcin (Millipore; Billerica, Mass.), a marker of osteoblasts, or rabbit anti-mouse Sca-1 (Epitomics; Burlingame, Calif.), a marker of hematopoietic stem cells. In the GI histopathology studies, tissue sections were incubated with rabbit anti-mouse IL-12R β 2, or rabbit anti-mouse leucine-rich-repeat-containing G-protein-coupled receptor 5 (LGR5), a GI stem cell marker that is expressed upon GI injury. After removing the primary antibodies, tissue sections were incubated with peroxidase conjugated anti-rabbit IgG (ImmPRESS; Vector Laboratories; Burlingame, Calif.). Red coloring of peroxidase labeled cells developed following incubation with AEC substrate (ImmPACT AEC; Vector Laboratories; Burlingame, Calif.) and were counterstained with CAT Hematoxylin (Biocare Medical, Concord, Calif.). Tissue sections were then immersed in Vectamount (Vector Laboratories; Burlingame, Calif.), covered with a cover slip, sealed with clear nail polish, and visualized using an Olympus Compound microscope (Olympus America, Inc; Center Valley, Pa.) at 100× magnification for bone marrow sections and 400× for jejunum.

Co-expression of Sca-1 and IL-12Rβ2 on hematopoietic stem cells was evaluated by incubating bone marrow tissue sections first with rabbit anti-mouse Sca-1 (Epitomics, Burlingame, Calif.) followed by incubation with Rabbit on Rodent HRP-Polymer (Biocare Medical; Concord, Calif.) and 3,3'-diaminodbenzidine substrate (Biocare Medical; Concord, Calif.). After treatment with denaturing solution (Biocare Medical; Concord, Calif.), tissue sections were incubated with rabbit anti-mouse IL-12R β 2 (Sigma; St Louis, Mo.) followed by incubation with Rabbit on Rodent AP polymer (Biocare Medical; Concord, Calif.) and Warp Red substrate (Biocare Medical; Concord, Calif.). Tissue sections were then counterstained in CAT Hematoxylin and visualized as described above. Using this method, cells expressing Sca-1 and IL-12Rβ2 were stained in brown and pink, respectively.

Example 5

Assessment with Non-Human Primates (NHP)

Male rhesus monkeys, Macaca mulatta, were purchased from Worldwide Primates, Inc., (Miami, Fla., USA). Animals of 3 to 4 years of age weighing 3. 5 to 5.8 Kg were acclimatized for at least 7 weeks. All rhesus monkeys included in the experiments were in good health by physical examination, were negative for Herpes B-virus, simian immunodeficiency virus, simian T-lymphotropic virus, and simian type retrovirus, and were vaccinated against hepatitis A and measles. Animals were housed individually in stainless steel monkey cages equipped with automatic watering systems. The animal room environment was continuously controlled for temperature (21±3° C.), humidity (30% to 70%), light cycle (12 hours light:12 hours dark), and air change (10 to 15 air changes/hour). A standard certified commercial primate chow was available to each monkey twice a day. Food was withdrawn overnight prior to irradiation and necropsy Animals were acclimated to the various procedures with positive reinforcement prior to study initiation. Health status was extensively evaluated to ensure animals were in good condition for the studies. All animals were provided prophylactic analgesia (buprenorphine) from day 5 to study completion. Specific euthanasia criteria were included in each experimental protocol to minimize suffering. Continuous clinical care (24 hours/7 days) were provided throughout the study to ensure prompt intervention when needed. A team of technicians and veterinarians trained in NHP medicine was responsible for clinical monitoring and provided state-of-the-art medical care.

Example 6

Allometric Dose Conversion from Mice to Rhesus Monkey

Recombinant murine IL-12 doses that were found effective against lethal TBI in mice were converted to their equivalent doses in rhesus monkey based on body surface area. Pharmacological equivalency of the species-specific equivalent doses were evaluated in relation to the recombinant human IL-12 stimulation of IFN-γ secretion from peripheral blood mononuclear cells (PBMC) in vitro and the PK and PD characteristics of recombinant human IL-12 in vivo.

Example 7

Isolation of CD14− PBMC and Quantification of IFN-γ Secretion

Human PBMC collected by apheresis were purchased from AllCells (Emeryville, Calif., USA). Mouse and rhesus monkey PBMC were from Bioreclamation (Liverpool, N.Y., USA). CD14− PBMC were isolated as follows. Red blood cells were removed from human PBMC by a single step gradient with Ficoll-Hypaque premium (Density=1.077; GE Healthcare Lifesciences; Piscataway, N.J., USA) and from rhesus monkey and mouse PBMC by lysis using ACK lysis buffer (Invitrogen; Carlsbad, Calif., USA). To remove IL-12-secreting endogenous monocyte populations, human and rhesus monkey PBMCs were labeled with mouse anti-human CD14PE antibody (AbD Serotec; Raleigh, N.C., USA), and mouse PBMCs were labeled with mouse anti-mouse CD14PE (AbD Serotec; Raleigh, N.C., USA). The excess antibody was removed and cells were incubated with magnetic beads conjugated with anti-PE antibody (Miltenyi Biotec; Auburn, Calif., USA). After removing the excess antibody, CD14+ cells were captured by adsorption to an LD column (Miltenyi Biotec; Auburn, Calif., USA) immobilized in a magnetic field (Quadro MACS®; Miltenyi Biotec; Auburn, Calif., USA). CD14− cells in the flow-through were collected, and those from humans were resuspended at a density of 14×106 cells/mL in cold fetal bovine serum (FBS) containing 20% dimethyl sulfoxide whereas those from rhesus monkey and mouse were resuspended at a density of 2.14×106 cells/mL in RPMI medium containing 10% FBS and antibiotics. IFN-γ was quantified by ELISA in supernatants from 2.5×105 human, rhesus monkey, or mouse CD14− PBMC incubated with various concentrations (range: 0 to 1000 pM) of recombinant human IL-12 or recombinant murine IL-12 for 16 hours at 37° C. All experiments were carried out in triplicate. The half maximal effective concentration (EC50) of IL-12 for stimulating IFN-γ secretion was calculated by SoftMax Pro® software version 3.1 (Molecular Devices; Sunnyvale, Calif., USA) using a 4-parameter logistic fit.

Example 8

Plasma PK and PD of Recombinant Human IL-12 in NHP

Radiation-naive rhesus monkeys received recombinant human IL-12 subcutaneously at a dose of either 250 ng/Kg (n=3) or 1000 ng/Kg (n=3). The concentrations of recombinant human IL-12, IFN-γ, and other potential biomarkers of recombinant human IL-12 were determined by ELISA in plasma samples withdrawn prior to the recombinant human IL-12 administration and at 2, 6, 12, 18, 24, 30, 36, 48, 72, 96, 120, 144 and 168 hours after recombinant human IL-12 administration.

Example 9

IL-12R BETA2 Expression 1N NHP and Human Bone Marrow and Small Intestine

Paraffin-embedded, sectioned tissues from NHP and human femoral bone marrow and jejunum/ileum were obtained from Biomax, Inc (Rockville, Md.). NHP and human tissue sections were immunohistochemically stained for IL-12Rβ2 using rabbit anti-human IL-12Rβ2 according to the procedures described in the section for mice histopathology studies.

Example 10

Survival Studies in NHP

At day 0, rhesus monkeys acclimated to the restraining procedure with positive reinforcement were subjected to TBI at an LD50/30 of 6.7 Gy. Irradiation was performed in two half-dose fractions (anteroposterior and posteroanterior) at the rate of 55 cGy/minute using a Cobalt-60 unit (Theratron 780; Theratronics; Ontario, Canada). The irradiation dose was monitored with 2 dosimeters (Thermoluminescent or NanoDot dosimeters; Landauer Inc.; Glenwood, Ill., USA) placed at the apex of the sternum and at the corresponding level in the interscapular area of each animal. Following TBI, animals were randomly assigned to receive subcutaneously either (a) vehicle at 24 hours post TBI (n=8), (b) 100 ng/Kg of recombinant human IL-12 at 24 hours post TBI (n=8), (c) 100 ng/Kg of recombinant human IL-12 at 24 hours and 7 days post TBI (n=8), (d) 250 ng/Kg of recombinant human IL-12 at 24 hours post TBI (n=8), or (e) 250 ng/Kg of recombinant human IL-12 at 24 hours and 7 days post TBI (n=8). Animals were monitored for survival and clinical and physical characteristics for up to day 30. The primary outcome measure was the percentage of survival. Peripheral blood cell counts, body weight, and clinical signs were evaluated as secondary outcome measures.

During the study, blood transfusions or antibiotic use was prohibited. Evidence of pain or discomfort was treated with intramuscular buprenorphine (0.01 mg/Kg to 0.05 mg/Kg at least every 8 hours). Nutritive support (e.g. liquid diets) was provided if animals presented with decreased appetite. Throughout the study, clinical signs were monitored at least twice a day, and complete blood counts and body weight were monitored once every other day. Hematology samples were analyzed with an automated hematology analyzer (Advia 120; Bayer Diagnostics; Tarrytown, N.Y., USA).

During the study, animals were euthanized if they had respiratory distress, anorexia/decreased appetite (complete anorexia for 3 days), weight loss (in excess of 20% of baseline body weight in 72 hours), unresponsiveness to touch, acute gross blood loss, generalized seizure, or abnormal vital signs. The euthanized animals or those found dead were subjected to a full macroscopic necropsy examination, including bacteriology testing. All animals were euthanized at the end of the study on day 31.

Example 11

Quantification of Recombinant Murine IL-12 and Recombinant Human IL-12 and their Biomarkers in Plasma Blood samples from mice and rhesus monkeys were collected into tubes containing ethylenediaminetetraacetic acid and were kept on ice (<30 minutes) until centrifugation. Samples were centrifuged at 1500×g for 10 minutes at 4° C. Plasma was aliquoted and stored at −70° C. until use. Plasma recombinant murine IL-12, recombinant human IL-12, and their potential biomarkers were assayed by ELISA. The ELISA kits for mouse IL-12 (p70) and IFN-γ were obtained from BioLegend (San Diego, Calif., USA), for NHP IL-12 from BioLegend (San Diego, Calif., USA), MabTech (Mariemont, Ohio, USA), and R&D Systems (Minneapolis, Minn., USA), for NHP IFN-γ from MabTech (Mariemont, Ohio, USA), for human EPO, IL-18, and IL-15 from R&D Systems (Minneapolis, Minn., USA), and for Neopterin from GenWay (San Diego, Calif., USA). All assays were carried out in triplicate according to the manufacturers' instructions except those for NHP IL-12 in which an in-house reference standard was used instead of the standard provided by the manufacturer.
Statistical Analyses Data were presented as mean±standard error (SE). Between-group differences in survival were evaluated with Kaplan-Meier survival analysis, followed by the Mantel-Cox Test for survival time and Pearson's chi-square test for percentage of survival. Between-group differences in blood cell counts were evaluated by analysis of variance (ANOVA), except for the number of platelet counts dropping below the transfusion level of 20,000 platelets/µl, which was analyzed by Pearson's chi-square test. Between group differences in clinical signs were evaluated by ANOVA. A P value of <0.05 was defined as the level of statistical significance.

Example 12

Figure 1B:
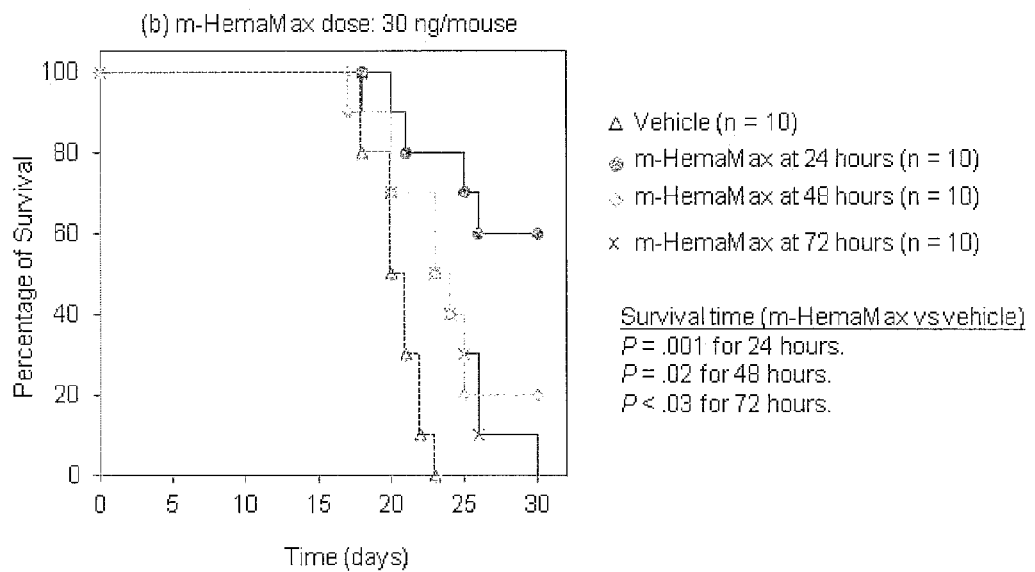
Figure 1C:
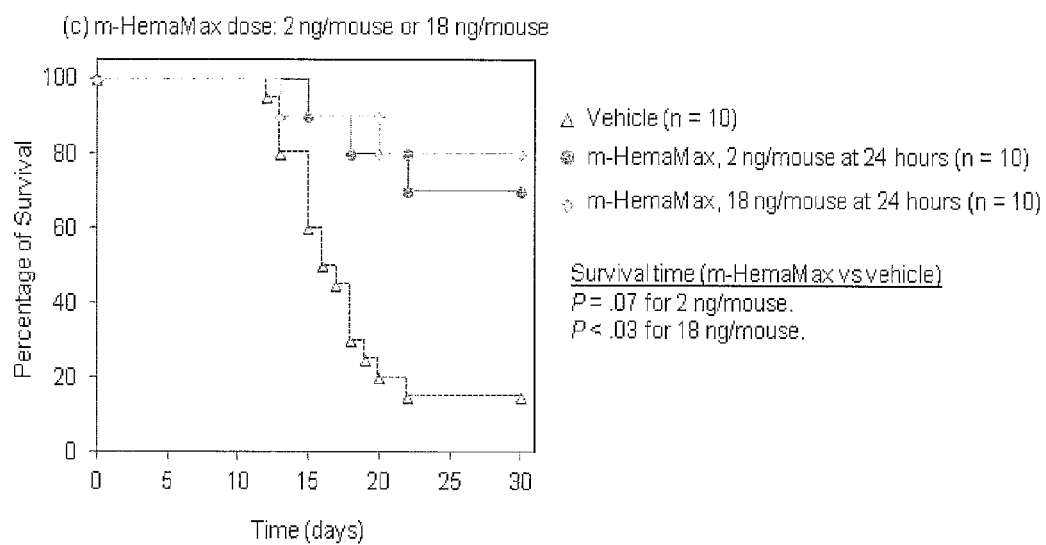

Single, Low Doses of Recombinant Murine IL-12 Administered 24 Hours Post TBI Increased Survival in Irradiated Mice In the initial studies, 87.5% of mice receiving a subcutaneous ostensible dose of 100 ng/mouse of recombinant murine IL-12 at 24 hours and 72 hours post TBI survived an 8 Gy for up to 30 days, whereas only 14% of vehicle mice survived lethal TBI by day 30 (P<0.005) (FIG. 1a). The actual recombinant murine IL-12 dose delivered in these studies was 10 ng/mouse. Subsequent studies evaluated whether a single dose of recombinant murine IL-12 was sufficient to provide similar radiomitigation effect. In these studies, a single, ostensible dose of recombinant murine IL-12 (300 ng/mouse; the actual delivered dose was 20-30 ng/mouse) significantly increased survival time when administered at either 24 hours (P=0.001), 48 hours (P=0.02), or 72 hours (P<0.03) after a 9 Gy TBI resulting in the LD 100/30 (FIG. 1b). Mice treated with recombinant murine IL-12 had a higher percentage of survival when recombinant murine IL-12 was administered at 24 hours compared to 48 hours post TBI (FIG. 1b). The difference in percentage of survival between the vehicle group and mice treated with recombinant murine IL-12 at 24 hours post TBI was statistically significant (0% vs 60%, respectively; P<0.05) (FIG. 1b).

recombinant murine IL-12 was reconstituted in P5.6TT, which increased dose delivery to nearly 90% of the intended dose. With this improvement, a single recombinant murine IL-12 dose of 2 ng/mouse or 18 ng/mouse provided significantly higher radiomitigation than did vehicle against a TBI dose of 7.9 Gy that resulted in an LD85/30 when administered 24 hours post radiation (FIG. 1c). At the dose of 2 ng/mouse, recombinant murine IL-12 significantly increased percentage of survival (P<0.02) and marginally increased survival time (P=0.07) compared to vehicle. At the dose of 18 ng/mouse, recombinant murine IL-12 significantly increased both the percentage of survival (P<0.005) and survival time (P<0.03) compared to vehicle. Animals treated with recombinant murine IL-12 at a higher dose, such as 160 ng/mouse, had modestly longer survival time compared to the vehicle group but a lower percentage of survival relative to animals treated with the 2 ng/mouse or 18 ng/mouse dose (data not shown). Thus, these findings indicate that a dose of approximately 20 ng/mouse is the optimal, efficacious dose of recombinant murine IL-12 to increase survival.

Figure 2:
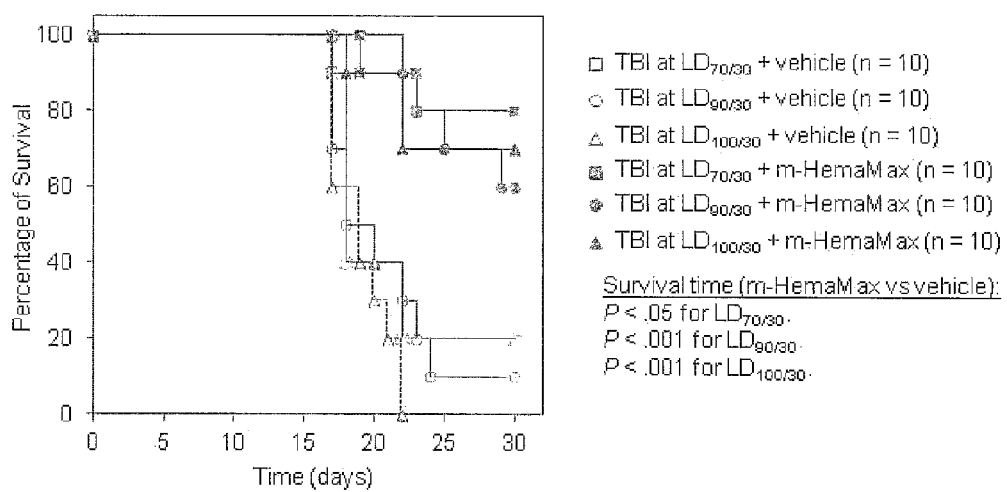
FIG. 2. Efficacy Of Recombinant Murine IL-12 In Increasing Survival Is Not Dependent On Radiation Dose In Mice. Animals were subjected to total body irradiation (TBI) at ascending radiation doses of 8.6 Gy ($LD_{70/30}$), 8.8 Gy ($LD_{90/30}$), and 9.0 Gy ($LD_{100/30}$) and subsequently received recombinant murine IL-12 at a dose of 20 ng/mouse 24 hours after irradiation. Mice were monitored for survival up to day 30. Vehicle was P5.6TT.
Figure 3A:
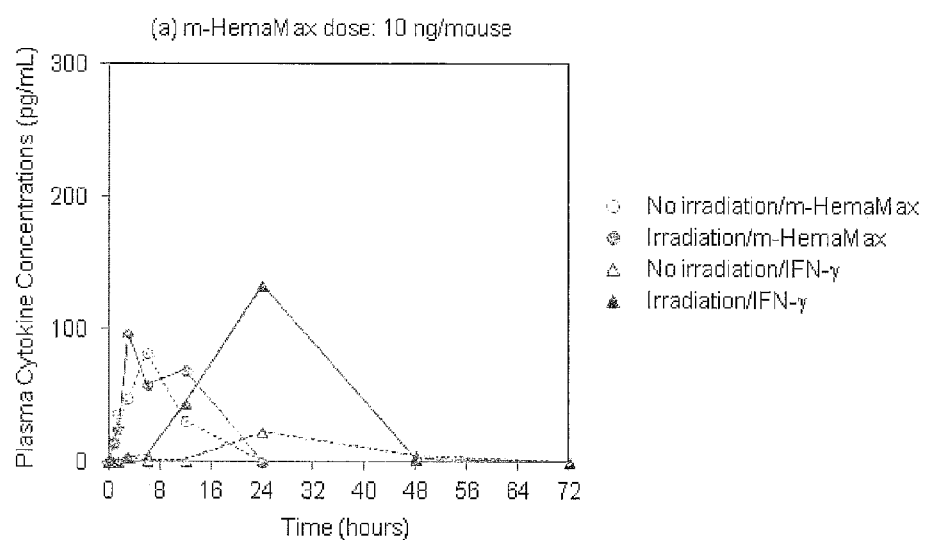
FIG. 3A-3D. Recombinant Murine IL-12 Administration Increased Plasma Recombinant Murine IL-12 And IFN-γ Levels In Irradiated And Non-Irradiated Mice. Animals received recombinant murine IL-12 subcutaneously at a dose of (a) 10 ng/mouse, (b) 20 ng/mouse, (c) 40 ng/mouse, or (d) 200 ng/mouse in the absence of irradiation or at 24 hours after an $LD_{90/30}$ of TBI. The plasma concentrations of recombinant murine IL-12 and IFN-γ were determined by ELISA in blood samples withdrawn at the indicated times. The y-axis scale in (d) is 8 times greater than those in (a) and (b) and 5 times greater than that in (c). n=3 per timepoint in each group.
Figure 3B:
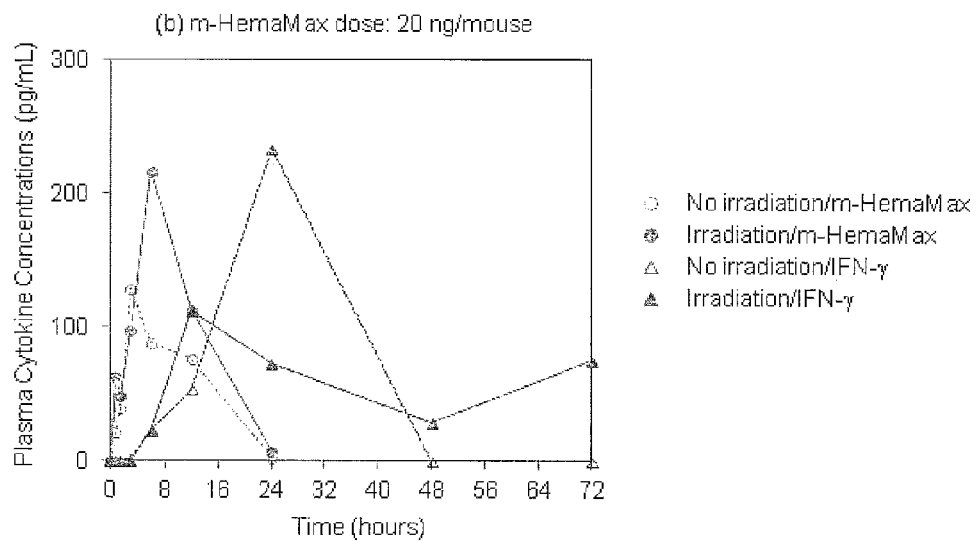
Figure 3C:
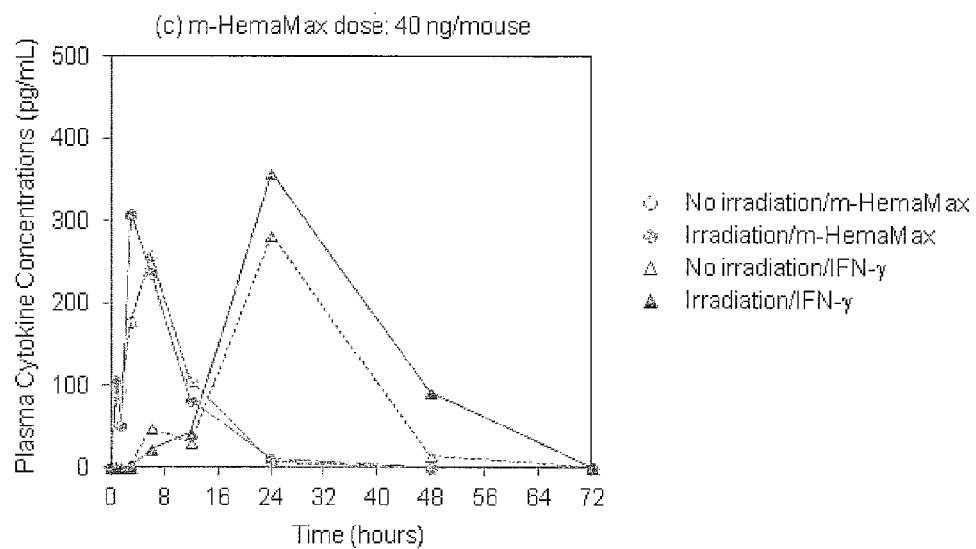
Figure 3D:
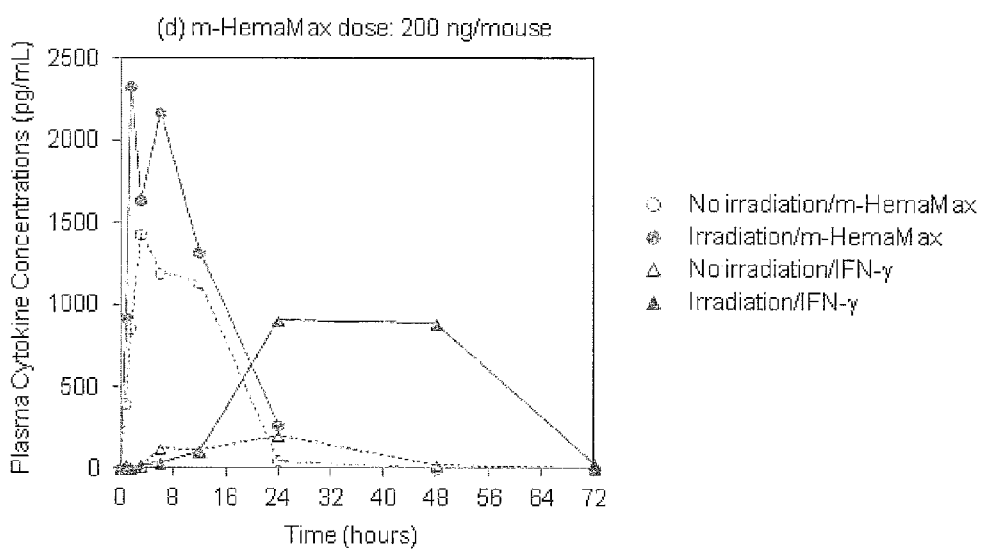

To evaluate the relationship between the radiation dose and percentage of survival upon treatment with recombinant murine IL-12, 3 ascending doses of radiation (8.6, 8.8, and 9.0 Gy corresponding to resultant LD 70/30, LD 90/30, and LD 100/30, respectively) were tested in mice. recombinant murine IL-12 at a dose of 20 ng/mouse administered 24 hours after TBI significantly increased survival time at all 3 levels of radiation intensities (FIG. 2). The percentage of survival in animals treated with vehicle was 20% at 8.6 Gy (LD70/30), 10% at 8.8 Gy (LD90/30), and 0% at 9.0 Gy (LD100/30) (FIG. 2). Compared to the vehicle groups, treatment with recombinant murine IL-12 resulted in significantly higher percentage of survival of 80% at LD70/30, 60% at LD90/30, and 70% at LD100/30 (P<0.05 for all) (FIG. 2), demonstrating a radiation dose-independence for recombinant murine IL-12 administration at 24 hours post TBI within the selected window of radiation exposures. Remarkably, comparable percentages of survival after a single, fixed dose of recombinant murine IL-12 at increasing radiation doses indicate that the efficacy of recombinant murine IL-12 is not decreased with increasing radiation dose. These data suggest that at radiation doses where immune, bone marrow, and GI damage overlap, recombinant murine IL-12 can provide mitigation of injury in all three radiosensitive tissues, thereby leading to an increase in survival that is relatively independent of radiation dose within a certain window of exposure.

Example 13

Plasma PK and PD of Recombinant Murine IL-12 in Irradiated and Non-Irradiated Mice Plasma concentrations of recombinant murine IL-12 and IFN-γ were determined over 72 hours in 2 groups of mice, which received increasing doses of recombinant murine IL-12 (from 10 ng/mouse to 200 ng/mouse) either in the absence of irradiation or 24 hours after an approximate LD90/30 of TBI (8.6 Gy). The recombinant murine IL-12 doses lower than 10 ng/mouse were not evaluated because of the limitations in recombinant murine IL-12 detection. recombinant murine IL-12 was detected in all plasma from animals receiving recombinant murine IL-12 (FIG. 3), but importantly, was not detectable in plasma samples from mice that did not receive recombinant murine IL-12 regardless of the presence or absence of irradiation (data not shown).

The exposure to recombinant murine IL-12 (area under the curve last; AUClast) increased dose proportionally from 10 ng/mouse to 40 ng/mouse regardless of the presence or absence of irradiation (FIG. 3 and Table 1).

TABLE 1

Plasma PK Characteristics of recombinant murine IL-12 in Irradiated and Non-Irradiated Mice.

| recombinant murine IL-12 | $C_{max}$ (pg/mL) | | $AUC_{last}$ (pg · h/mL) | | $T_{max}$ (hours) | | $t_{1/2}$ (hours) | |
|---|---|---|---|---|---|---|---|---|
| dose, ng/mouse | NR | R | NR | R | NR | R | NR | R |
| 10 | 82.8 | 96.4 | 628 | 728 | 6 | 3 | na | na |
| 20 | 129.5 | 217.2 | 1453 | 2364 | 3 | 6 | 3.7 | 3.5 |
| 40 | 257.8 | 308.8 | 2720 | 2701 | 6 | 3 | 3.5 | 4.2 |
| 200 | 1428 | 2332 | 21008 | 37059 | 3 | 1.5 | 4.8 | 7.2 |

Animals received recombinant murine IL-12 subcutaneously at a dose of 10 ng/mouse, 20 ng/mouse, 40 ng/mouse, or 200 ng/mouse in the absence of irradiation or at 24 hours after an $LD_{90/30}$ of TBI. The plasma concentrations of recombinant murine IL-12 were determined by ELISA.
AUC = area under the curve;
$C_{max}$ = maximum plasma concentrations;
NR = no irradiation;
R = irradiation;
TBI = total body irradiation;
$T_{max}$ = time to achieve the maximum plasma concentration;
$t_{1/2}$ = half life.

Interestingly, maximum plasma concentrations (Cmax) of recombinant murine IL-12 were consistently higher in irradiated mice as compared to non-irradiated mice at all doses (FIG. 3). The exposure to recombinant murine IL-12 (AUClast) at the dose of 200 ng/mouse was disproportionately higher than those at the lower doses (10 ng/mouse to 40 ng/mouse), suggesting that PK properties of recombinant murine IL-12 are non-linear at the higher dose ranges (Table 1). In the dose range of 10 ng/mouse to 40 ng/mouse, recombinant murine IL-12 reached Cmaxin 3 hours to 6 hours and was eliminated with a half-life of approximately 4 hours (Table 1).

Recombinant murine IL-12 administration increased plasma IFN-γ concentration with a lag time at all study doses (FIG. 3). Of significance, IFN-γ production was not abrogated in irradiated mice (FIG. 3). In fact, for all recombinant murine IL-12 doses, except the optimal dose of 20 ng/mouse dose, plasma IFN-γ levels were higher in irradiated mice compared to non-irradiated mice (FIG. 3). The exposure to IFN-γ dose proportionally increased as a function of increasing recombinant murine IL-12 dose from 10 ng/mouse to 200 ng/mouse (data not shown). Importantly, IFN- was not detected in plasma of mice, which did not receive recombinant murine IL-12 regardless of the presence or absence of irradiation.

Figure 4:
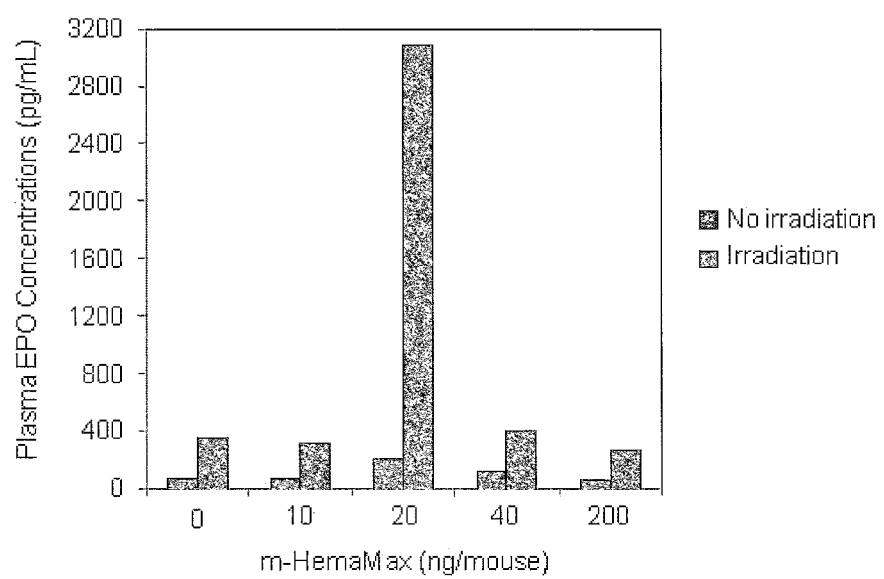
FIG. 4. Optimal Recombinant Murine IL-12 Dose Of 20 Ng/Mouse Increased Plasma EPO Concentration In Irradiated Mice. Animals received recombinant murine IL-12 subcutaneously at a dose of (a) 10 ng/mouse, (b) 20 ng/mouse, (c) 40 ng/mouse, or (d) 200 ng/mouse in the absence of irradiation or at 24 hours after an $LD_{90/30}$ of TBI. The plasma concentrations of EPO were determined by ELISA in blood samples withdrawn at 12 hours after recombinant murine IL-12 administration.

Since preliminary studies had shown that co-administration of recombinant murine IL-12 and EPO in a certain regimen led to a substantial increase in survival following lethal radiation exposure (data not shown), we sought to assess whether recombinant murine IL-12 may affect plasma levels of EPO in irradiated and non-irradiated mice. Because of the limited sample availability, plasma EPO levels could be measured in only 1 early timepoint, 12 hours after recombinant murine IL-12 administration (FIG. 4). In non-irradiated, untreated animals, EPO was detectable in plasma at low pg/mL range (FIG. 4). Irradiation increased plasma EPO levels nearly linearly up to 80 hours post TBI, suggesting that EPO is a part of the physiological response to radiation injury (data not shown). Remarkably, however, at the optimal dose of 20 ng/mouse at 12 hours post administration (36 hours post radiation exposure), recombinant murine IL-12 substantially increased plasma EPO concentrations over the radiation-induced levels (FIG. 4), indicating that recombinant murine IL-12 potentiates the EPO-mediated physiological response to radiation, but only at or near the optimal dosing level. It is noteworthy that, at this optimal dose, plasma EPO levels were also increased in non-irradiated mice (FIG. 4). It remains to be further evaluated as to whether the EPO response to recombinant murine IL-12 administration occurs at a narrow window of recombinant murine IL-12 dose range because a highly potentiated EPO response was observed only after administration of the 20 ng/mouse dose (FIG. 4). It is interesting to note that the IFN-γ response appeared to be subdued at the 20 ng/mouse dose of recombinant murine IL-12, the dose at which EPO was upregulated by recombinant murine IL-12, as compared to the other doses assessed. In a mice model of multiple sclerosis, administration of EPO was reported to downregulate the inflammatory response, and in particular, suppress IFN-γ. Thus, these findings suggest that the increased plasma EPO levels may play a role in the suppression of plasma IFN-γ levels in irradiated mice that received recombinant murine IL-12 at the dose of 20 ng/mouse (FIG. 3b), leading to a decrease in the inflammatory response to radiation.

Other biomarkers of recombinant murine IL-12 administration were also screened, namely tumor necrosis factor-alpha (TNF-α) and stem cell factor (SCF), but the plasma levels for these factors were found to be below the limit of quantitation.

Example 14

Administration of Recombinant Murine IL-12 at 24 Hours after TBI Mitigated Radiation-Induced Injury in Murine Bone Marrow and Small Intestine Femoral bone marrow from irradiated mice treated with vehicle or recombinant murine IL-12≥24 hours after TBI (LD30/30) were stained for IL-12Rβ2 and evaluated for histological signs of recovery from radiation-induced injury at 12 days post TBI. As a control, bone marrow from non-irradiated, untreated mice was characterized with the presence of IL-12Rβ2-expressing hematopoietic stem cells, identified by co-staining for Sca-1 (a murine stem cell marker; see below), immature megakaryocytes with lobulated nuclei surrounded by a narrow rim of cytoplasm, matured megakaryocytes with lobulated nuclei and voluminous cytoplasm, and myeloid progenitor cells in the metamyelocyte stage (FIG. 5a).

Figure 5:
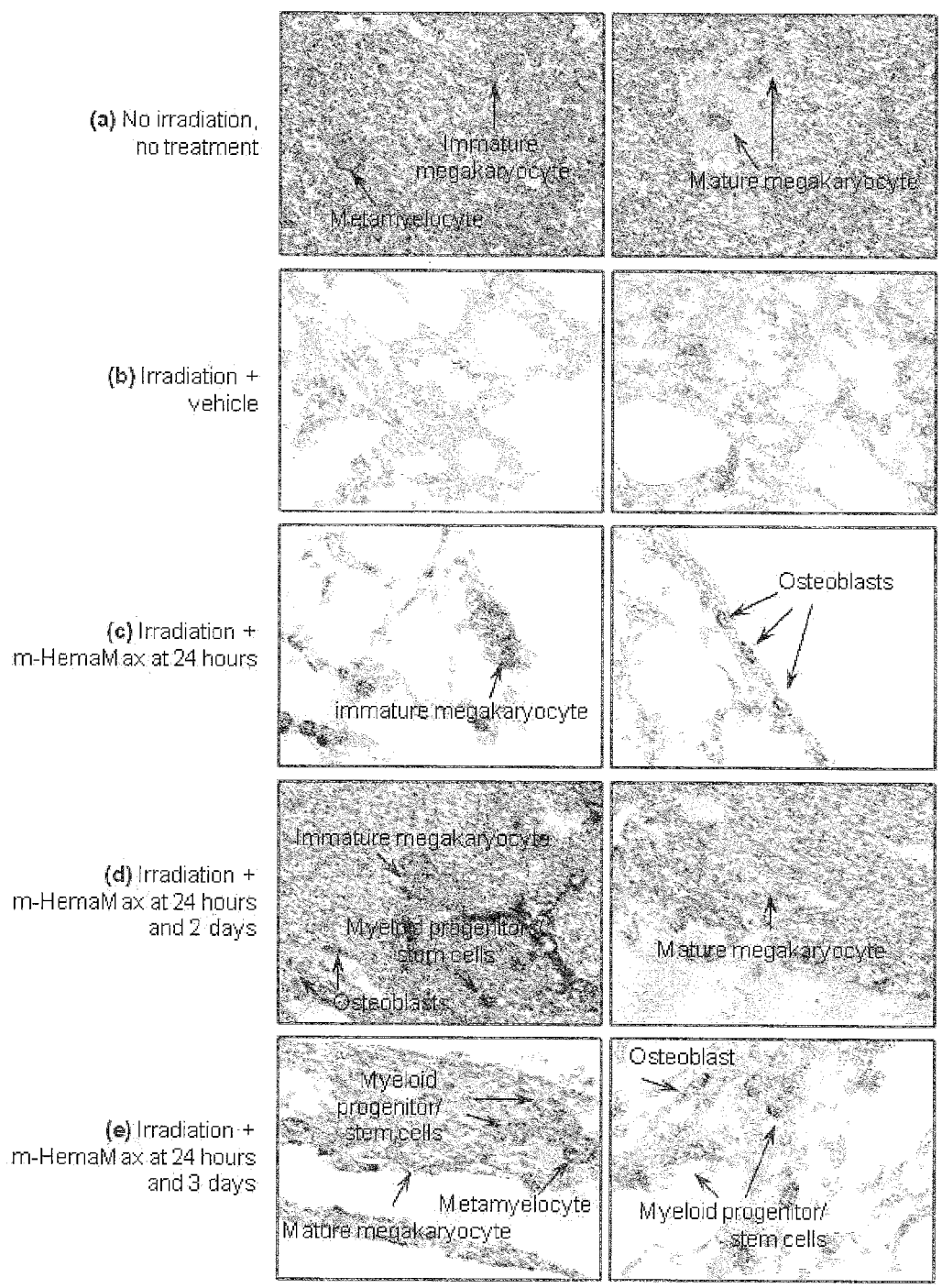
FIG. 5(a)-(g). Recombinant Murine IL-12 Promotes Hematopoietic Recovery In Irradiated Mice. Representative sections of femoral bone marrow from non-irradiated, untreated mice that were stained for IL-12Rβ2 (orange color) are shown in (a). Animals were subjected to TBI (8.0 Gy) and subsequently received vehicle (P5.6TT) or recombinant murine IL-12 (20 ng/mouse) subcutaneously at the indicated times post irradiation (b-f). An additional group of mice received recombinant human IL-12 at 24 hours after TBI (g). Femoral bone marrow was immunohistochemically stained for IL-12Rβ2 (orange color) 12 days after irradiation. While bone marrow from mice treated with vehicle lacked IL-12Rβ2-expressing cells and showed no signs of hematopoietic regeneration (b), mice treated with recombinant murine IL-12 showed hematopoietic reconstitution and the presence of IL-12Rβ2-expressing megakaryocytes, myeloid progenitors, and osteoblasts (c-f). Mice treated with recombinant human IL-12 showed IL-12Rβ2-expressing osteoblasts but lacked megakaryocytes (g). Magnification=100×.

Bone marrow from mice treated only with vehicle and subjected to an LD30/30 of TBI (8.0 Gy) was characterized with minimal signs of hematopoietic regeneration and the complete lack of IL-12Rβ2-expressing cells after 12 days following irradiation (FIG. 5b). In contrast, mice treated with various dosing regimens of recombinant murine IL-12 showed varying levels of hematopoietic reconstitution, which was characterized with the presence of IL-12Rβ2- expressing myeloid progenitors, megakaryocytes, and osteoblasts (FIG. 5c-f). Mice treated with recombinant human IL-12, which has been demonstrated to not cross react with the murine IL-12 receptor, showed some signs of regeneration, however, lacked megakaryocytes (FIG. 5g). For mice treated with recombinant human IL-12, however, no increase in the survival was observed, as compared with the vehicle control group.

In order to further evaluate as to whether morphologically identified cells were indeed hematopoietic stem cells and osteoblasts, bone marrow tissue sections were stained for the corresponding markers, respectively, Sca-1 and osteocalcin. As depicted in FIGS. 6 a and b, IL-12Rβ2 expression was observed on cells that were morphologically identified as hematopoietic stem cells and osteoblasts, which expressed Sca-1 and osteocalcin, respectively. Co-expression of IL-12Rβ2 and Sca-1 in bone marrow tissue sections was also evaluated by a dual staining approach. As depicted in FIG. 6c, a discrete subset of hematopoietic stem cells were co-stained for the presence of both IL-12Rβ2 and Sca-1. Both immature and mature megakaryocytes expressing IL-12Rβ2 was also evident in the bone marrow tissue sections (FIG. 6c). These findings suggest a direct role for IL-12 signaling pathway in hematopoietic reconstitution.

Figure 7:
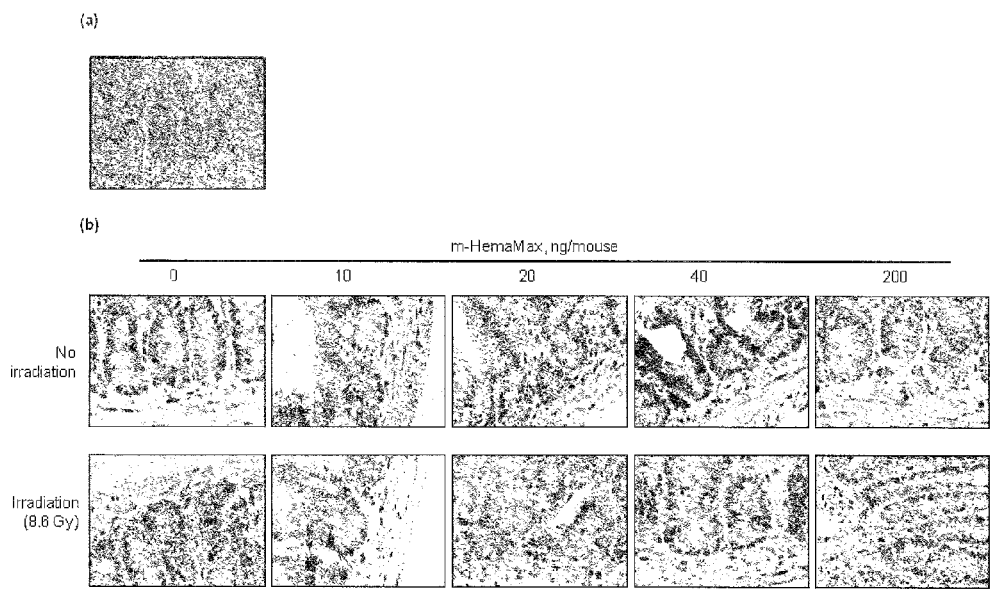
FIG. 7(a)-(b). Recombinant Murine IL-12 At Low Dose Suppresses Radiation-Induced Intestinal Injury In Mice. The IL-12Rβ2 expression in jejunal crypts (a) and the suppression of jejunal expression of LGR5 (b), a GI stem cell injury marker, are shown. Mice received vehicle (P5.6TT) or recombinant murine IL-12 subcutaneously at the indicated doses either in the absence of irradiation or 24 hours after TBI (8.6 Gy). Three days after irradiation, jejunum tissues were removed and immunohistochemically stained for IL-12Rβ2 (a) or LGR5 (b). Representative images show LGR5 in brown as indicated with arrows. Magnification=400.

Similar to hematopoietic stem cells and osteoblasts in femoral bone marrow, mice jejunal crypts expressed IL-12Rβ2 (FIG. 7a). In the absence of irradiation, recombinant murine IL-12 administration at doses up to 200 ng/mouse did not cause injury in jejunal crypts (FIG. 7b, upper panel). Exposure to TBI (8.6 Gy), however, resulted in substantial jejunal damage 3 days after irradiation, as evidenced by the widespread expression of LGR5, a GI stem cell marker shown to be expressed upon chemotherapy-induced GI injury. Remarkably, administration of recombinant murine IL-12 at the low dose range of 10 ng/mouse to 40 ng/mouse dose-dependently mitigated radiation-induced jejunal damage, with no LGR5 expression evident at the optimal, efficacious dose of 20 ng/mouse (FIG. 7b, lower panel). On the other hand, recombinant murine IL-12 at the high dose of 200 ng/mouse exacerbated jejunal injury (FIG. 7b, lower panel). As observed with the recombinant murine IL-12 dose ranges for optimal increases in survival, these data point to a window of opportunity for mitigation of radiation injury by recombinant murine IL-12 in a very low dose range of the drug that is also effective in alleviating bone marrow damage.

Example 15

Allometric Dose Conversion from Mice to NHP

In order to achieve a similar radiomigation effect in rhesus monkey, doses that are pharmacologically equivalent to those given to mice should be administered to rhesus monkeys. Based on the Food and Drug Administration (FDA) guidelines, the optimal 20 ng/mouse dose (1000 ng/Kg) and a non-optimal 80 ng/mouse (4000 ng/Kg) dose in mouse translate, respectively, to the 250 ng/Kg and 1000 ng/Kg doses in rhesus monkey. However, eliciting a pharmacologically equivalent response at species-specific equivalent doses depends on several factors including similar drug exposure and specific reactivity with the primary target site in both species. Therefore, prior to evaluating the efficacy of the radiomitigation effects of recombinant human IL-12 in NHP, we first examined the pharmacological equivalency of the species-specific equivalent doses.

Example 16

Recombinant Human IL-12 and Recombinant Murine IL-12 Potently Stimulated IFN-γ Secretion from Human, Rhesus Monkey, and Mouse CD14– PBMC In Vitro Target reactivity to recombinant human IL-12 was evaluated by comparing EC50 values of recombinant human IL-12 and recombinant murine IL-12 for stimulating the secretion of IFN-γ from CD14– PBMC. As reported previously [33], we observed that recombinant human IL-12 did not cross-react with PBMC isolated from mouse and rat (EC50>1000 pM). In contrast, recombinant human IL-12 potently stimulated IFN-γ secretion from both human and rhesus monkey PBMC with EC50 values of, respectively, 2.51±0.51 pM and 1.05±0.10 pM. The EC50 value of recombinant murine IL-12 for stimulating IFN-γ secretion from mouse PBMC was 0.35±0.29 pM. These findings suggest that the reactivities of monkey and mouse PBMC to, respectively, recombinant human IL-12 and recombinant murine IL-12 are similar in relation to IFN-γ secretion in vitro.

Plasma PK of Recombinant Human IL-12 in Rhesus Monkeys

Plasma PK of recombinant human IL-12 was examined in rhesus monkeys following a single administration of recombinant human IL-12 at two doses of 250 ng/Kg and 1000 ng/Kg in the absence of irradiation. Following administration, the exposure (AUClast) to recombinant human IL-12 increased in proportion to dose (Table 2).

TABLE 2

Plasma Pharmacokinetic Characteristics of recombinant human IL-12 in Non-Irradiated Rhesus Monkeys.

| Recombinant human IL-12 dose, ng/Kg | $C_{max}$ (pg/mL) | $AUC_{last}$ (pg · h/mL) | $T_{max}$ (hours) | $t_{1/2}$ (hours) |
|---|---|---|---|---|
| 250 | 38.3 ± 8.4 | 1192 ± 382 | 10 ± 3.5 | 20.4 ± 12.3 |
| 1000 | 193.3 ± 61.3 | 5708 ± 1488 | 8 ± 3.5 | 40.6 ± 24.1 |

Animals received recombinant human IL-12 subcutaneously at a dose of either 250 ng/Kg or 1000 ng/Kg in the absence of irradiation. The plasma concentrations of recombinant human IL-12 were determined by ELISA. AUC = area under the curve; $C_{max}$ = maximum plasma concentrations; $T_{max}$ = time to achieve the maximum plasma concentration; $t_{1/2}$ = half life.

Figure 8:
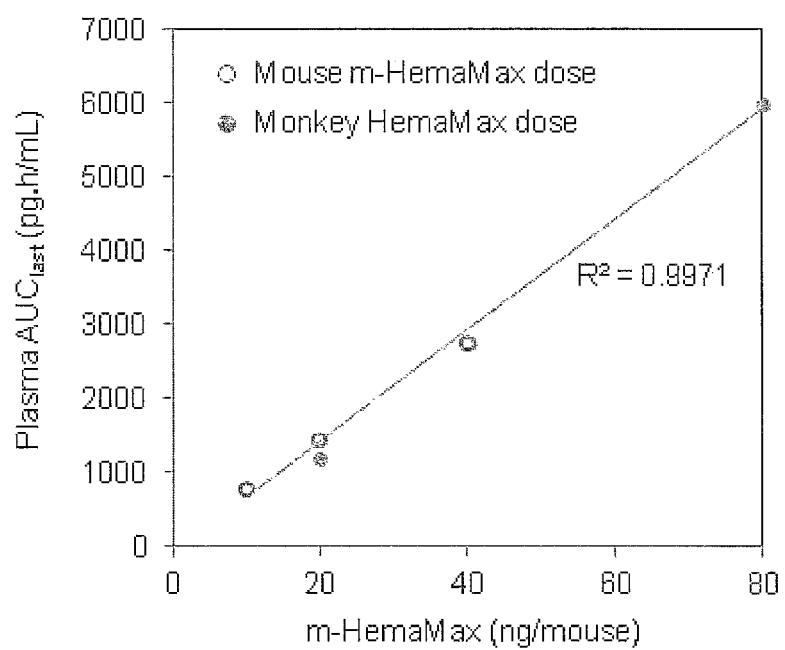
FIG. 8. Similar Exposures To Recombinant Murine IL-12 And Recombinant Human IL-12 At Species-Specific Equivalent Doses In Mice And Rhesus Monkeys. The plot of plasma $AUC_{last}$ of recombinant murine IL-12 versus the dose administered to mice in the absence of irradiation was linear at doses from 10 ng/mouse to 40 ng/mouse. The plasma $AUC_{last}$ of recombinant human IL-12 at monkey equivalent doses of 20 ng/Kg and 80 ng/Kg was in good agreement with the extend of dose-dependent increases in recombinant murine IL-12 exposure in mice.

The AUClast of recombinant human IL-12 in rhesus monkey was perfectly superimposed linearly for the AUClast of recombinant murine IL-12 in mice over the dose range of 10 ng/mouse to 80 ng/mouse (FIG. 8), suggesting that the species-specific equivalent doses calculated from mice studies provided similar drug exposure in monkeys. The 200 ng/mouse dose was not included in this analysis as it appeared that recombinant murine IL-12 exhibits different PK characteristics at higher doses (Table 1).

Recombinant human IL-12 at a single dose of 250 ng/Kg or 1000 ng/Kg was well tolerated and was not associated with overt signs of toxicity, except for the occurrences of transient decreases in appetite in the 1000 ng/Kg group.

Example 16

Figure 9A:
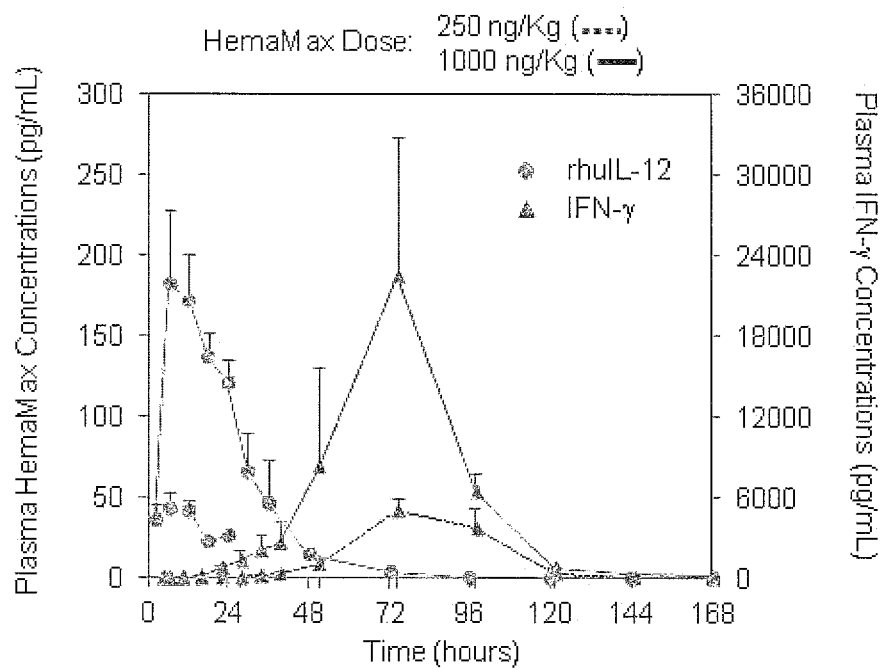
FIG. 9A-9C. Exemplary Recombinant Human IL-12 (e.g. HemaMax) Administration Increased Plasma IFN-γ, IL-18, EPO, IL-15, And Neopterin Concentrations In Non-Irradiated Rhesus Monkeys. (a) Temporal kinetics of IFN-γ relative to that of recombinant human IL-12. (b) Temporal kinetics of IL-18 and EPO. (c) Temporal kinetics of IL-15 and neopterin. Animals received recombinant human IL-12 subcutaneously at a dose of either 250 ng/Kg or 1000 ng/Kg in the absence of irradiation. The plasma concentrations of recombinant human IL-12, IFN-γ, IL-18, EPO, IL-15, and neopterin were determined by ELISA in blood samples withdrawn at the indicated times. n=3 per timepoint in each group, except for neopterin, which was n=1.

Recombinant Human IL-12 Administration Increased Plasma Concentrations of IFN-γ, IL-15, IL-18, Neopterin, and EPO in Non-Irradiated Rhesus Monkeys In monkeys, subcutaneous administration of recombinant human IL-12 appeared in plasma shortly after administration and was not detectable after 72 hours (FIG. 9a). Moreover, as observed in mice with recombinant murine IL-12, recombinant human IL-12 was observed to increase plasma IFN-γ concentration in proportion to dose (FIG. 9a). Temporal kinetics of IFN-γ response in rhesus monkey was, however, different from mouse in that the IFN-γ response was delayed for a longer period of time and was much higher in magnitude (FIG. 9a). Neither recombinant human IL-12, nor IFN-γ, was detected in plasma of monkeys that did not receive recombinant human IL-12.

Figure 9B:
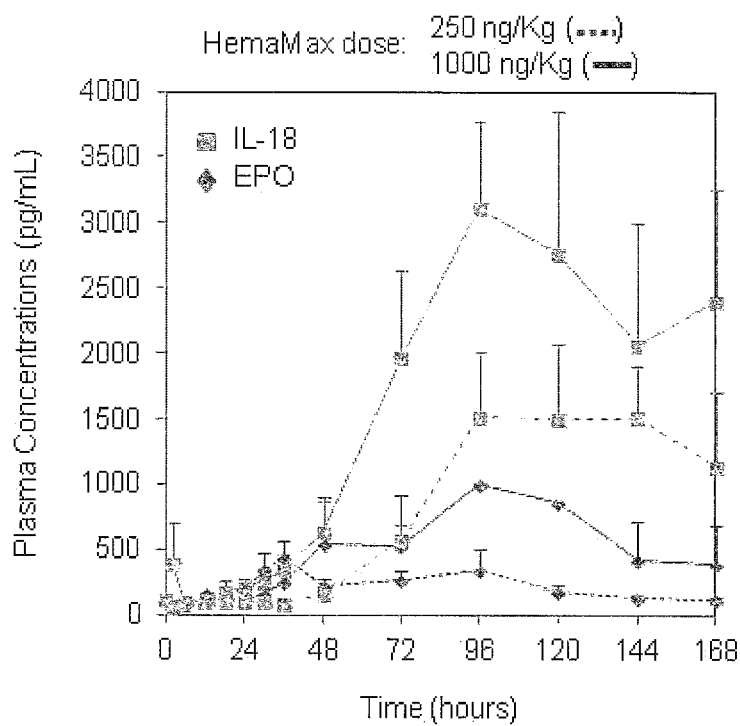
Figure 9C:
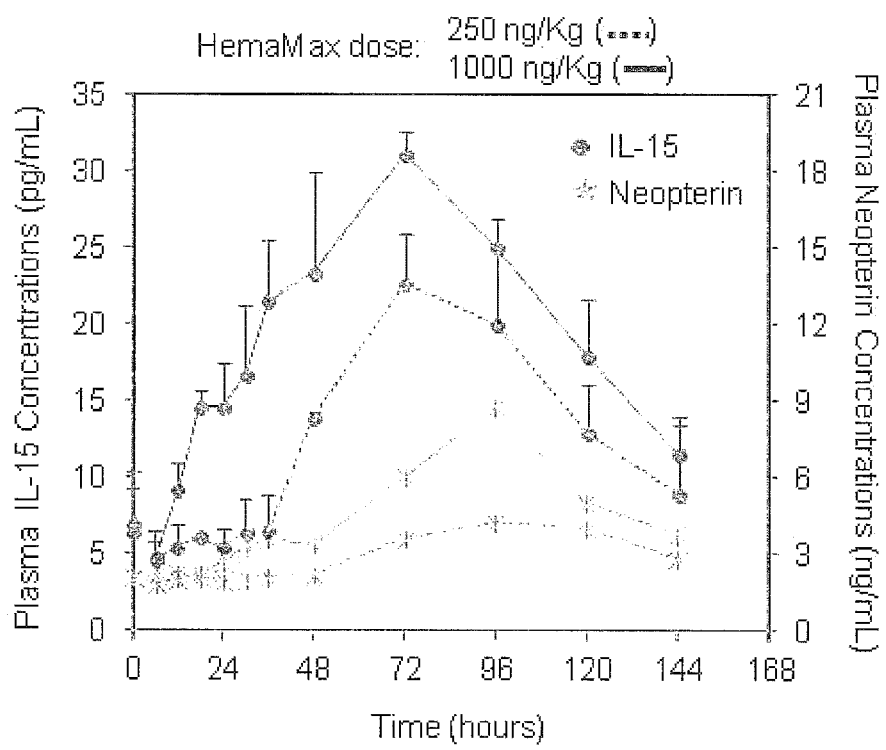

Of other potential biomarkers, the exposure (AUClast) to IL-18 and EPO was increased by 2.4-fold and 5.1-fold, respectively, as the recombinant human IL-12 dose was increased from 250 ng/Kg to 1000 ng/Kg (FIG. 9b). recombinant human IL-12 also increased plasma IL-15 and neopterin concentrations, peaking at 72 hours and 96 hours, respectively, post recombinant human IL-12 administration (FIG. 9c). In contrast to previous reports in humans, the plasma concentrations of rhesus monkey TNF-α and IL-10 were not changed.

Example 17

NHP and Human Bone Marrow and Small Intestine Express IL-12R2

Figure 10A:
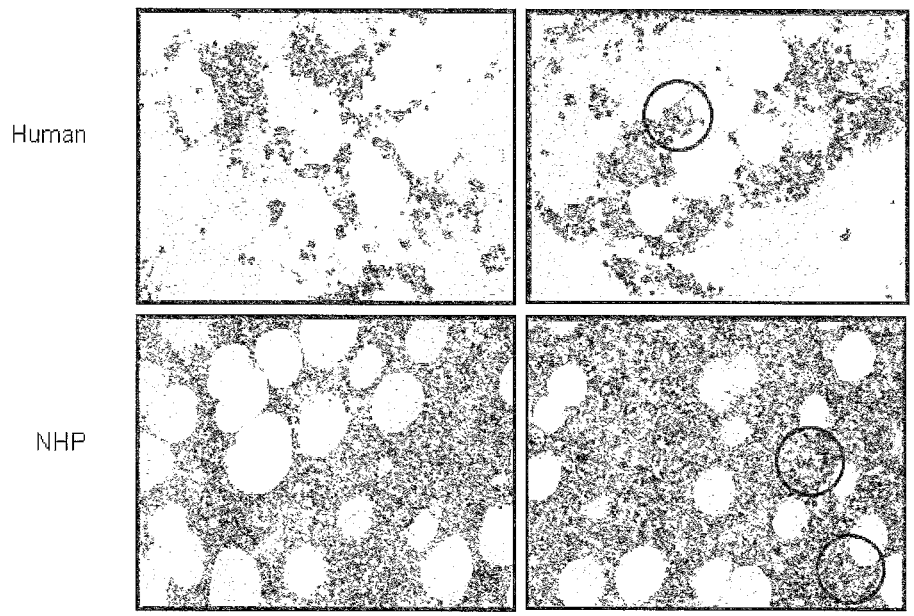
FIG. 10. NHP And Human Bone Marrow And Small Intestine Express IL-12Rβ2. Tissues from NHP and human femoral bone marrow (a) and jejunum/ileum (b) were immunohistochemically stained for IL-12Rβ2. (a) Progenitor cells and megakaryocytes expressing IL-12Rβ2 are shown. Adipocytes did not express IL-12Rβ2. (b) Intestinal crypts expressing IL-12Rβ2 are shown. Lymphoid cells in the lamina propria and submucosal regions also expressed IL-12Rβ2. C=crypt; LP=lamina propria. Magnification was 40× in (a) and 100× in (b).

The expression of IL-12Rβ2 in non-irradiated NHP (rhesus monkeys) and human femoral bone marrow and jejunum/ileum was evaluated by immunohistochemistry. As depicted in FIG. 10A, NHP, as well as human, progenitor cells and megakaryocytes expressed IL-12Rβ2. The expression of IL-12Rβ2 was also found on osteoblasts/osteoclasts from the bone marrow. However, it could not be determined as to whether these cells were osteoblasts and/or osteoclasts because the donated tissues were smears and did not include periosteum or other bone tissues. Bone marrow adipocytes were not stained positive for IL-12Rβ2.

Figure 10B:
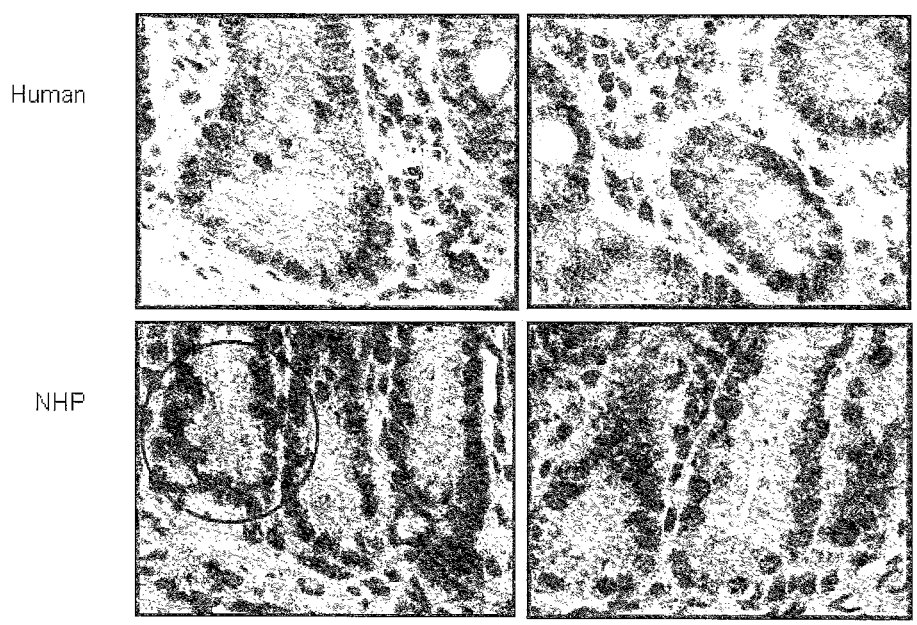

In the small intestine, IL-12Rβ2 was most commonly expressed in crypts (FIG. 10b). It is not known if IL-12Rβ2-expression in the intestinal crypt is localized to Paneth cells, multipotent stem cells, or both. IL-12Rβ2 expression was also noted in lymphoid cells populating the lamina propria and submucosal regions (FIG. 10B). Mucin secreting goblet cells did not express IL-12Rβ2. Both crypt and lamina propria IL-12Rβ2-expressing cells could represent multifunctional mesenchymal-origin myofibroblasts that can serve as crypt shape-forming cells that also occupy both a stem cell niche and act as non-professional antigen presenting cells to immunomodulatory cells in the lamina propria. Further studies will establish the cellular and functional identity of IL-12Rβ2-expressing cells in intestinal crypts and their supportive role in intestinal regeneration after radiation exposure.

Example 18

Figure 11A:
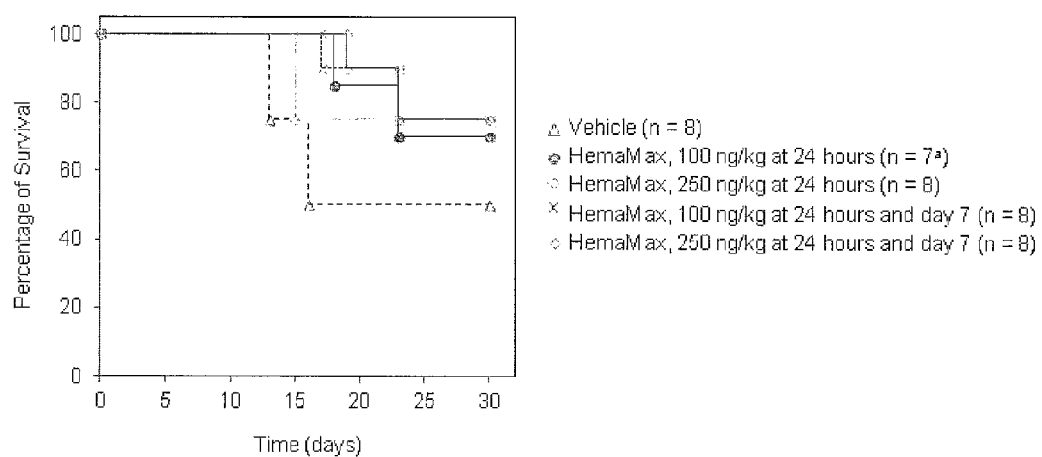
FIG. 11A-11B. Recombinant Human IL-12 Initiated At Least 24 Hours Post Irradiation Increased Percentage Of Survival Of Unsupported Monkeys. Individual dosing groups (a) and the pooled recombinant human IL-12 dosing group (b) are shown. Animals were subjected to an $LD_{50/30}$ of TBI at day 0 and subsequently received either vehicle (P5.6TT) or recombinant human IL-12 subcutaneously at the indicated dosing regimens. Supportive care was prohibited during the study. Animals were monitored for survival up to 30 days. $^a$One animal was excluded from the study due to a broken tooth.
Figure 11B:
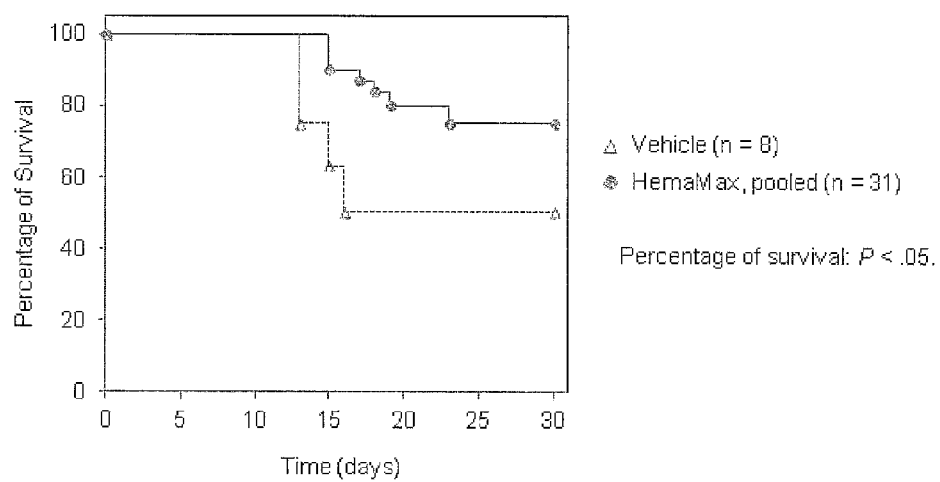

Recombinant Human IL-12 Administration Increased Survival in Irradiated, Unsupported Rhesus Monkeys In a pilot study of 40 animals, the percent survival of rhesus monkeys exposed to an LD50/30 of TBI (6.7 Gy) was determined following treatment with 100 ng/Kg or 250 ng/Kg of recombinant human IL-12 administered at 24 hours or at 24 hours and 7 days post TBI. This study was conducted in the absence of any supportive care, including antibiotics. The doses of recombinant human IL-12 were chosen based on PK/PD studies in rhesus monkeys and were equivalent to recombinant murine IL-12 doses of 8 ng/mouse and 20 ng/mouse, respectively. As is depicted in FIG. 11a, recombinant human IL-12 at both doses, following either single or two administrations, mitigated death due to irradiation to the same extent. Overall percentages of survival were 71% in the 100 ng/Kg single dose group (n=7) and 75% in all other groups receiving recombinant human IL-12 (n=8) compared to 50% in the vehicle group. Between-group differences in percentage of survival were not statistically significant, most likely because of the small number of animals in each group (n=8), but also because both recombinant human IL-12 doses were likely within the efficacious dose range. However, analysis of the percent survival regardless of the recombinant human IL-12 dosing regimen indicated that when pooled together, monkeys treated with recombinant human IL-12 had significantly higher percent survival than those receiving vehicle (75% vs 50%, respectively; P=0.05) (FIG. 11b).

Example 19

Figure 12A:
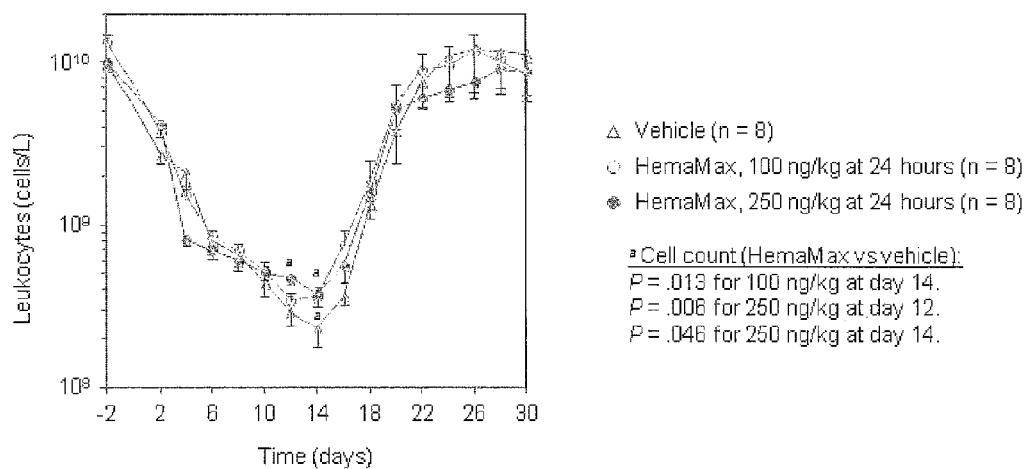
FIG. 12A-12B. Recombinant Human IL-12 Administration Decreased Leukopenia (A) And Thrombocytopenia (B) At Nadir In Irradiated, Unsupported Rhesus Monkeys. Animals were subjected to an $LD_{50/30}$ of TBI at day 0. Animals received subcutaneously either vehicle (P5.6TT) or recombinant human IL-12 at a dose of 100 ng/Kg or 250 ng/Kg at 24 hours post TBI. Blood samples were withdrawn at the indicated times, and leukocytes and platelets were counted by an automated hematology analyzer.
Figure 12B:
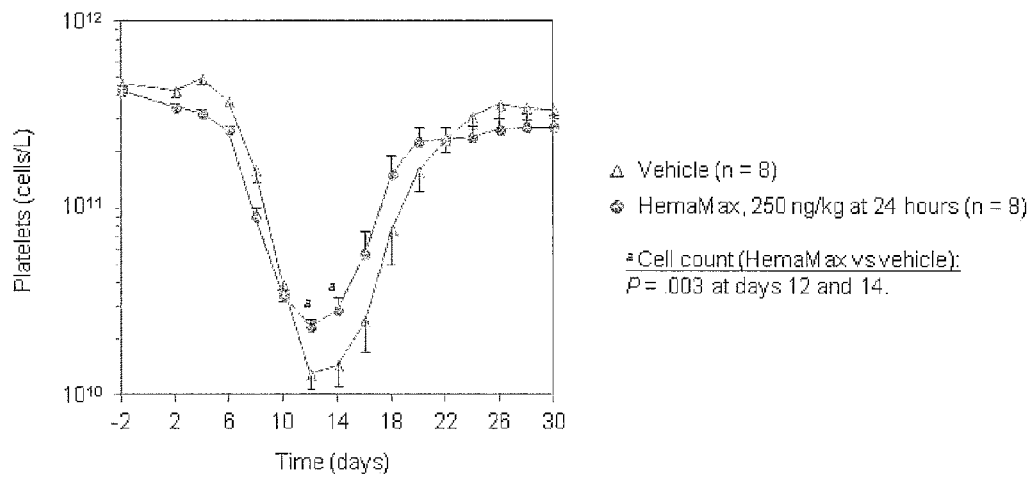

Changes in Blood Cell Counts of Irradiated, Unsupported Rhesus Monkeys Following Recombinant Human IL-12 Administration Three analyses were conducted to assess differences in blood cell counts during the study period. In the first analysis, where blood cell counts were analyzed from day 1 up to day 30, animals treated with recombinant human IL-12 had significantly higher numbers of leukocytes and thrombocytes at days 12 and 14, around the nadir, for the 100 ng/Kg and 250 ng/Kg doses, as compared to animals treated with vehicle (FIG. 12).

In a second analysis, where blood cell counts were analyzed from day 1 up to day 14, the day before any animals died, animals treated with recombinant human IL-12 had higher platelets counts compared to animals treated with vehicle (P=0.079 for the 250 ng/Kg group and P=0.02 for the 100 ng/Kg twice dosing group) during nadir (days 12 to 14). Additionally, in comparison to the vehicle group, animals treated with recombinant human IL-12 had significantly higher counts of leukocytes (P<0.01 for the 250 ng/Kg group and P<0.04 for the 100 ng/Kg twice dosing group) and reticulocytes (P<0.04 for the 250 ng/Kg group and P<0.001 for the 100 ng/Kg group) during nadir (days 12 to 14). The same trend was apparent for neutrophil, basophil, and lymphocyte counts, but they did not reach acceptable levels of statistical significance.

In a third analysis the number of animals that reached clinically low platelet counts during the study was assessed. This analysis revealed a remarkable difference between the vehicle and recombinant human IL-12 groups in the number of platelet counts dropping below a threshold level of 20,000 platelets/µL, a level generally necessitating platelet transfusion. In the recombinant human IL-12 250 ng/Kg group, only 4 out of 16 (25%) platelet counts at the nadir (day 12 to day 14) dropped below the transfusion threshold of less than 20,000 platelets/µL whereas 12 out of 15 (80%) platelet counts for the vehicle animals were below the threshold level during the same period of time (P=0.007).

Taken altogether, these findings indicate that recombinant human IL-12 increases leukocytes, platelet, and reticulocyte counts just prior to the days on which animals begin to die from radiation toxicity (day 13, FIG. 11a). Interestingly, vehicle-treated animals that survived up to day 30 also had a quick recovery of blood cell counts, which were statistically indistinguishable from those in the recombinant human IL-12 groups. These findings suggest that mortality likely occurs in animals that do not show a strong blood cell recovery around the nadir day(s). The validity of this hypothesis was evaluated by comparing blood cell counts of animals stratified by the mortality status, i.e., those surviving up to day 30 versus animals dying after day 12. In this analysis, the blood cell counts on the day before death was taken for animals that died after day 12. The comparison day for the surviving animals in each group was the average day on which the decedents in a particular group died (days 14 to 18). This analysis demonstrated that, regardless of the particular treatment group, animals surviving up to day 30 had significantly higher counts of platelets, neutrophils, leukocytes, reticulocytes, and lymphocytes than those that died after day 12 (P<0.001 to P<0.05). When compared by treatment group, animals treated with 100 ng/Kg recombinant human IL-12 had significantly higher counts of neutrophils, leukocytes, and lymphocytes than did those treated with vehicle in both survivors and decedent groups (P<0.001 for all three cell types). In addition, animals treated with 100 ng/Kg recombinant human IL-12 had a numerically higher platelet and reticulocyte counts. These findings suggest that recombinant human IL-12-induced increase in blood cell counts around nadir may play a key role in promoting survival following radiation exposure.

Example 20

Figure 13A:
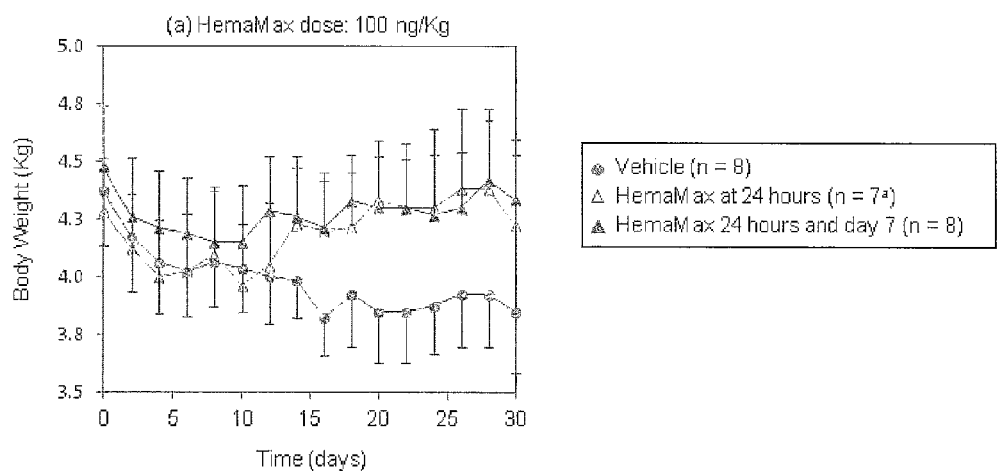
FIG. 13A-13D. Irradiated Rhesus Monkeys Receiving Recombinant Human IL-12 Had Less Body Weight Loss Than Animals Receiving Vehicle. Body weights in Kg (a and b) and in percentage (c and d) are shown for the 100 ng/Kg and 250 ng/Kg dose groups. Monkeys were subjected to an LD50/30 of TBI at day 0 and subsequently received either vehicle (P5.6TT) or recombinant human IL-12 subcutaneously at the indicated dosing regimens. Supportive care was prohibited during the study. Body weights were recorded every other day for up to day 30.
Figure 13B:
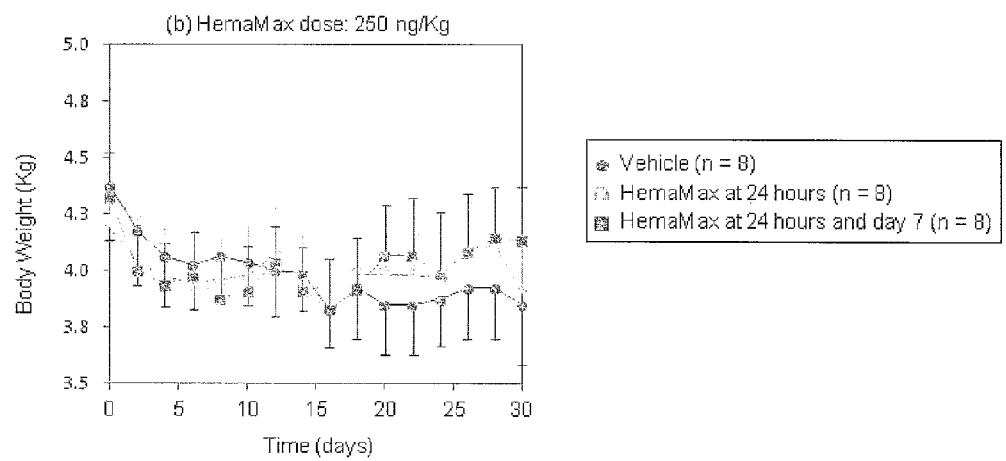
Figure 13C:
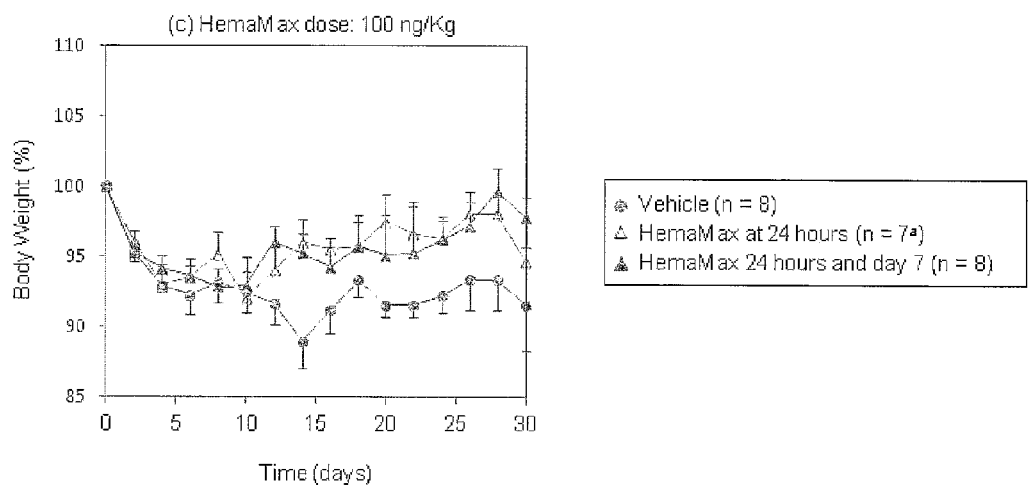
Figure 13D:
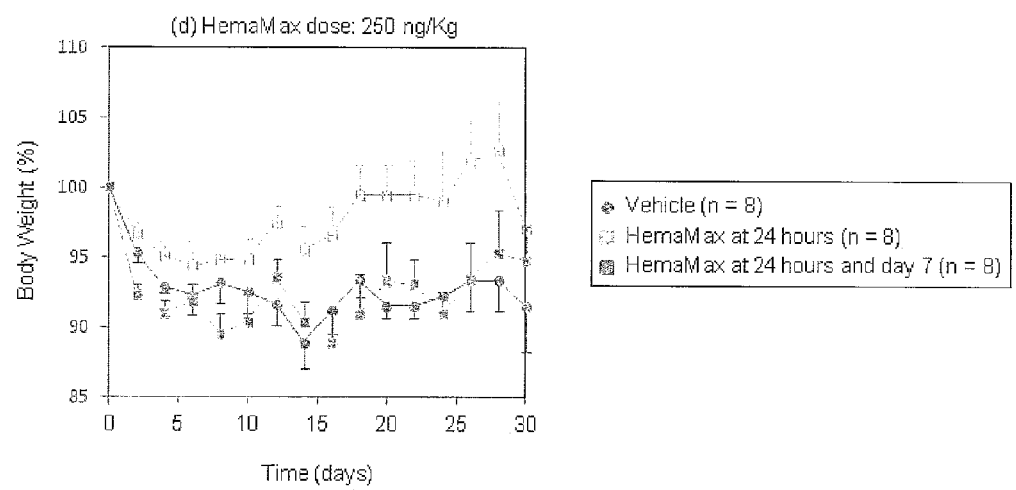

Clinical and Physical Characteristics of Irradiated, Unsupported Rhesus Monkeys Following Recombinant Human IL-12 Administration Animals receiving recombinant human IL-12 at the dose of 100 ng/Kg (once or twice) had consistently higher mean body weights than did those in the vehicle group from days 14 to day 30 (FIG. 13a). Animals treated with recombinant human IL-12 at the dose of 100 ng/Kg (once or twice) or 250 ng/Kg (once) had less weight loss than did animals treated with vehicle from days 14 to 30 (FIGS. 13 c and d). Although the between group differences in body weight or weight loss were not statistically significant, when the analysis of body weight loss was limited to day 12—the approximate day for blood cell nadir and the day after which animals began to die (FIG. 11a)—the pooled recombinant human IL-12-treated animals had significantly less body weight loss than those treated with vehicle (95. 3±0.8% versus 91.6±1.5%, respectively; P=0.04). Logistic regression demonstrated that weight loss after day 12 was a strong predictor of survival (P<0.001). Other clinical signs (appetite, physical activity, diarrhea, and feces color) were not significantly different from the vehicle group, although appetite and physical activity improved in recombinant human IL-12 treated animals, and the incidence of diarrhea and black or red feces declined in the 250 ng/Kg twice dosing regimen group. However, above-mentioned clinical signs did predict mortality after day 12 by logistic regression (P=0.002 for decreased appetite, P<0.001 for decreased physical activity, P=0.04 for incidence of diarrhea, and P=0.008 for incidence of red or black feces). Clinical signs of severe deterioration and stress, including chronic anorexia, sunken eyes, dehydration, hunched and/or crouching posture and weakness, started approximately at day 14 with no remarkable between-group differences in the incidence or onset. All adverse clinical signs were consistent with acute radiation syndrome following exposure to radiation.

Gross pathology along with organ and hemoculture bacteriology evaluation was conducted for all animals, which died or were euthanized before the end of study. There were no recombinant human IL-12—related macroscopic lesions. The incidence of hemorrhage was 12.5% (1/8 animals) in the pooled animals treated with 100 ng/Kg or 250 ng/Kg of recombinant human IL-12 compared to 50% (2/4) in the vehicle animals. In the vehicle group, all of the decedent animals (4/8 animals) were found dead while only 1 animal in the recombinant human IL-12 groups was found dead and 8 animals were humanely euthanized before the end of study. A diagnosis of septicemia was confirmed by isolation of the same bacterial strain in at least 2 organs of all 13 animals.

In the vehicle group, 75% (3/4) found dead animals presented a combination of bacteria most likely from the intestinal and cutaneous flora and 25% (1/4) presented organ infections with only bacteria most likely from the cutaneous bacterial flora. In the various recombinant human IL-12-treated groups, 8 out of 9 animals (89%) presented a combination of bacteria from the intestinal and cutaneous flora, including 2 which also presented organ infections with bacteria most likely from the environment. The other animal (1/9) presented organ infections with only bacteria most likely from the cutaneous flora. These results suggest that opportunistic infections were present in all animals that died preterminally in this animal model of acute radiation syndrome.

Aspects and embodiments of the present disclosure are generally based on the principle that radiation damage caused by TBI dose-dependently implicates immune, hematopoietic and the GI tissues, as these are the most radiosensitive targets in the body. Lymphocytes are the most sensitive cells to radiation toxicity and, at irradiation doses of greater than about 2 Gy, are the first to be depleted from circulation. The lymphocyte loss is followed by a decline in granulocytes and then platelet levels over a period of days. Acute-onset anemia may occur secondary to hemorrhage. At doses of >4 Gy, radiation adversely affects GI epithelium/endothelium, and the resulting clinical manifestation is due to a combination of the hematopoietic and GI toxicities, presenting with nausea, vomiting, diarrhea, headache, fatigue, fever, and abdominal pain.

It is also recognized that death originating from immune and hematopoietic toxicity occurs because of infection due to impaired immunity and/or hemorrhage due to thrombocytopenia, while death originating from GI toxicity is often because of multisystem organ failure, overwhelming sepsis, and complications of bleeding. In the event of a radiological attack, radiation mitigators with multi-tissue effects capable of alleviating immune, hematopoietic and GI toxicities when administered after radiation exposure, are useful.

The examples provided herein clearly demonstrated that an exemplary IL-12 preparation, recombinant human IL-12, mitigated death due to radiation-induced damage effects/toxicity in both mice and monkeys following administration of a single, low dose. In both mice and monkeys, recombinant human IL-12 increased survival when administered at protracted timepoints post radiation exposure, such as 24 hours or longer, in the absence of supportive care, including oral or topical antibiotics. In irradiated mice and monkeys, recombinant human IL-12 promoted survival at various levels by stimulating the immune system in the peripheral blood and extravascular spaces, promoting hematopoietic regeneration in bone marrow, decreasing tissue injury in the small intestine, and triggering a generalized anti-apoptotic and anti-inflammatory effect throughout the body.

In one embodiment, the optimal murine dose that provided these radiomitigation effects is approximately 20 ng/mouse. Method of extrapolating equivalent human dose are well known in the art. The dose is lower than previous reports for recombinant human IL-12 efficacy in radioprotection and as a hematological adjuvant in cancer therapy due to the use of formulated protein in the present studies.

Moreover, protracted administration of recombinant human IL-12 at 24 hours post irradiation appears to act via a somewhat different mechanism as compared with our previous studies where recombinant human IL-12 was administered either before, or shortly after, radiation exposure. Evidence for this comes from a comparison of the bone marrow recovery in the current murine radiomitigation studies, as compared to previous studies in mice. In the current studies, bone marrow recovery appeared to be much slower, likely due to the timing of recombinant human IL-12 administration (24 hours before TBI in previous studies versus 24 hours after TBI in this study).

Moreover, as further demonstration of efficacy, exemplary IL-12 (recombinant human IL-12, e.g. recombinant human IL-12) markedly decreased the radiation induced expression of LRG5, a stem cell marker which also serves as a marker of GI injury, when administered at 24 hours post radiation exposure. Exemplary IL-12 (recombinant human IL-12, e.g. recombinant human IL-12), at doses from about 10 ng/mouse to about 40 ng/mouse administered about 24 hours post TBI, reduced radiation-induced LGR5 expression. In contrast, with about 200 ng/mouse (recombinant murine 11-12 recombinant murine IL-12) administration about 24 hours after TBI, appeared to exacerbate radiation-induced GI injury as evidenced by an increase in LGR5 expression.

This finding is consistent with earlier reports that high doses of IL-12 exacerbated radiation injury to the GI tract. Data obtained in both mice and rhesus monkeys show significant increases in body weights for recombinant murine IL-12 and recombinant human IL-12-treated animals, respectively, after irradiation (FIG. 13), thereby providing further support for the protective GI effect of recombinant human IL-12 treatment.

Moreover, as further demonstration of efficacy, recombinant human IL-12 can reduce radiation toxicity and increase survival in mice was confirmed in monkeys. Recombinant human IL-12 administered to rhesus monkeys at 24 hours post radiation significantly increased survival (P=0.05, pooled treated groups vs. vehicle control). Recombinant human IL-12-treated monkeys had significantly higher numbers of platelets, leukocytes, and reticulocytes at the nadir, had lower incidence of hemorrhage, and had higher body weights from day 12 to day 30.

In addition, thrombocytopenia was less severe in animals treated with recombinant human IL-12 than in those treated with vehicle. Further, a remarkable difference was observed between the vehicle and recombinant human IL-12-treated groups in platelet counts dropping below the threshold level of 20,000 platelets/μL, a level that generally necessitates platelet transfusion. In the recombinant human IL-12-treated 250 ng/Kg group, only 4 out of 16 (25%) platelet counts at the nadir (day 12 to day 14) dropped below the transfusion threshold of less than 20,000 platelets/μL whereas 12 out of 15 (80%) platelet counts for the vehicle animals were below the threshold during the same period of time (P=0.007).

In a yet another example demonstrating the efficacy, recombinant human IL-12 was administered after TBI, the earliest at 24 hours post irradiation—a window of time considered minimally necessary for mobilization of medical personnel and resources to the affected area. This demonstrates the utility of recombinant human IL-12 as a life-saving intervention in the event of a radiological disaster. These findings provide evidence that when administered as single, low doses after TBI, recombinant human IL-12 mitigates radiation-induced toxicity in at least three major systems affected by radiation: the immune system, the bone marrow compartment, and the GI tract.

An additional event related to the recombinant human IL-12 mitigation of radiation toxicity is the stimulation of anti-apoptotic/anti-inflammatory effects via release of EPO, a known general protector of tissue against cytotoxic damage via anti-apoptotic/anti-inflammatory mechanisms. Several interdependent networks may underlie the radiomitigation effect of recombinant human IL-12. It is known that IL-12 is a central regulator of cell-mediated immune responses and modulates the synthesis and secretion of several immune mediators. In cancer patients, intraperitoneal/intravenous/subcutaneous administration of IL-12 increased peritoneal/serum levels of IFN-γ, TNF-α, IL-10, IL-8, VEGF, IP-10, and neopterin. In the disclosure provided herein, recombinant human IL-12 administration dose-dependently increased plasma IFN-γ levels in both mice and monkeys. IFN-γ orchestrates many distinct cellular programs through transcriptional control over large numbers of genes, resulting in heightened immune surveillance and immune system efficiency against infection.

In addition to IFN-γ, recombinant human IL-12 increased plasma levels of EPO in mice and IL-15, IL-18, neopterin, and EPO in monkeys. IL-15 and IL-18, alone and/or in combination, play important roles in the development, homeostasis, and functions of CD4+ T cells, CD8+ T cells, natural killer (NK) cells, and NK T cells. In synergism with IL-12, IL-18 stimulates the production of IFN-γ in T helper 1 cells. Neopterin, an auto-oxidation product of 7,8-dihydroneopterin, reflects IFN-γ activity and, as a corollary, is considered as an indicator of systemic immune activation.

The examples provided herein demonstrated that recombinant human IL-12 stimulated EPO production in mice and NHP. This finding indicate that EPO can play a central role in mediating the radiomitigation activity of recombinant human IL-12.

EPO can have immunomodulatory, neuroprotective, and cardioprotective activities. EPO enhances cell viability, modulates surface antigen expression, and increases IL-12 secretion in dendritic cells—the most potent antigen presenting cells—suggesting that immunomodulatory functions of EPO may partly be mediated through dendritic cells, which in turn induce specific T cell responses. Cytoprotective effects of EPO have at least in part, been linked to its antioxidant, anti-inflammatory and antiapoptotic activities. In various models of cytotoxicity induced by toxicants, ischemia, hypoxia, or oxidative stress, EPO increased cellular antioxidant capacity and/or decreased oxidant injury in kidney, neurons, and retinal pigment epithelial cells while it reduced apoptosis in neurons, vascular smooth muscle cells, cardiomyocytes, and endothelial cells.

The underlying mechanisms of radiomitigation conferred by exogenous recombinant human IL-12 indicate a multi-level response orchestrated by exogenous delivery of recombinant human IL-12 (FIG. 14). Current evidence indicated that that recombinant human IL-12 triggers responses at, at least, 4 levels by directly activating IL-12 receptors (a) on immune cells in peripheral blood and bone marrow (Level 1), (b) on hematopoietic stem cells and other key cells of the bone marrow niche, such as osteoblasts (Level 2), (c) on GI stem cells (Level 3), and likely (d) on kidney cells (Level 4), whereby EPO, a cytoprotective factor, is released following radiation exposure (FIG. 14).

The most immediate response is the recombinant human IL-12-induced Level 1 Response, which involves key radioresistant cells of the immune system. At the very early stages following radiation exposure, most immune cells undergo apoptosis with a rank order according to their radiosensitivity (B cells>T regulatory cells>T helper cells>T cytotoxic cells>T memory cells>NK cells). The immune cells that are likely to remain functional at 24 hours or longer post irradiation are those that are the least radiosensitive, namely NK cells and differentiated cells, such as macrophages and dendritic cells. Thus, recombinant human IL-12 administered after radiation can initiate the Level 1 response by promoting the proliferation and activation of the surviving NK cells, macrophages, and dendritic cells. The tridirectional cross-talk between NK cells, macrophages and dendritic cells further promotes their maturation and expansion via cytokines identified as biomarkers of the restoration of innate immunity, namely IFN-γ, IL-15, IL-18 and neopterin. This tridirectional cross-talk further leads to the production of endogenous IL-12 secreted from dendritic cells (FIG. 14). As a consequence, early immune competence is established via innate immunity mechanisms following TBI. Continuous production of endogenous IL-12 from pathogen-activated dendritic cells also serves as a positive feedback loop and plays a key role in sustaining the initial response to exogenous recombinant human IL-12, perhaps for weeks after radiation exposure (FIG. 14). Evidence for the continued production of endogenous IL-12 following exogenous administration of recombinant human IL-12 is the presence of IL-12Rβ2 on hematopoietic cells 12 days after TBI only in mice that were treated with recombinant human IL-12.

Recombinant human IL-12 initiates the Level 2 Response through interaction with the primary bone marrow cells involved in hematopoiesis. In the bone marrow, residual hematopoietic stem cells, osteoblasts, and megakaryocytes are likely the cell types that remain extant and functional 24 hours following exposure to lethal doses of radiation. The presence of IL-12Rβ2—expressing stem/progenitor cells, megakaryocytes, and/or osteoblasts in bone marrow from mice, NHP, and humans indicates that these cells are direct targets of recombinant human IL-12. Through its receptors, recombinant human IL-12 initiates the Level 2 response by promoting proliferation and differentiation of the surviving stem cells following radiation exposure, leading to hematopoietic regeneration (FIG. 14). Activation of osteoblasts appears to be crucial for the survival, expansion, and homing of hematopoietic stem cells and megakaryocytes. It has been shown that exposure to lethal doses of radiation leads to a specific expansion of osteoblastic niche, whereby the surviving pool of radioresistant osteoprogenitors proliferates close to the endosteal bone areas. The relatively long-lived, surviving megakaryocytes were also observed close to the endosteal surface of trabecular bone rather than in their normal parasinusoidal site. Megakaryocytes release factors that stimulated the expansion of osteoblastic niche. Consistent with these findings, immunohistochemical examinations in our study revealed a similar cellular configuration in mice bone marrow, showing cellular islands consisting of osteoblastic niche, megakaryocytes, and hematopoietic stem cells close to the bone. In CD34+, IL-12Rβ2-positive bone marrow cells, recombinant human IL-12 increases EPO secretion while, in contrast to its traditional action in mature lymphocytes, it decreases IFN-γ secretion [unpublished data from our lab], providing a milieu that promotes expansion of hematopoietic stem cells, eventually leading to regeneration of mature blood cells including platelets and leukocytes (FIG. 14). EPO also contributes to the development of such optimal milieu by suppressing the over-production of inflammatory cytokines such as IFN-γ, IL-6, IL-2, and TNF-α from T cells Inhibition of IFN-γ production by EPO is in agreement with our findings showing that plasma IFN-γ levels were suppressed in irradiated mice at a recombinant human IL-12 dose (20 ng/mouse) that substantially increased plasma EPO levels. Furthermore, the increased plasma EPO concentrations may, at least in part, explain the lack of increases in monkey plasma levels of proinflammatory cytokines such as IL-2, IL-6, and TNF-α following recombinant human IL-12 administration.

Recombinant human IL-12 initiates the Level 3 Response by preserving GI stem cells, which regenerate intestinal crypt cells and ensure intestinal integrity (FIG. 14). Recombinant human IL-12-induces intestinal cell-cell border integrity, which reduces pathogen leakage, increases food absorption, and decreases diarrhea. The reduction of "leaky gut syndrome" provides further immune-related benefit by decreasing pathogen entry into peripheral blood circulation (FIG. 14). Recombinant human IL-12-induced GI recovery thus provides a greater chance of survival following lethal radiation exposure.

Recombinant human IL-12 initiates the Level 4 Response by increasing plasma levels of EPO, likely by enhancing EPO release from the kidneys following direct activation of its renal receptors. Given its antioxidant, anti-inflammatory, and antiapoptotic activities, EPO acts as a general cytoprotective factor in the body, enhancing cellular viability in a diverse set of organs/tissues including the brain, peripheral nerves, heart, kidney, skin, and intestine. EPO may also preserve key cells involved in Level 1 and 2 survival advantages of recombinant human IL-12, namely niche bone marrow cells, as well as mature and immature dendritic cells, macrophages, and NK cells against radiation toxicity. Matured dendritic cells may also release IL-12 in response to EPO and/or IFN-γ, providing a positive feedback loop that amplifies the events originally initiated by exogenous administration of recombinant human IL-12.

Finally, continuous generation of endogenous IL-12 induced by a single dose of exogenous recombinant human IL-12 in irradiated, immunocompromised hosts is another key survival advantage. Continuous endogenous production of IL-12 is primarily a result of the Level 1 recombinant human IL-12-induced response. In addition, bacterial and pathogenic products gaining access to the circulation following radiation injury can activate dendritic cells to promote innate and adaptive responses, and further lead to a release of endogenous IL-12. Thus, recombinant human IL-12 may promote proliferation of surviving immune cells, cells of the bone marrow niche, namely osteoblasts and megakaryocytes, hematopoietic stem cells, and provides protection against radiation injury to key intestinal stem cells through various feedback loops. These feedback loops promote the generation of soluble factors such as endogenous IL-12, IFN-γ, and EPO, allowing regeneration of hematopoietic system and recovery of immune and GI functions (FIG. 14).

These examples demonstrated that for the first time that recombinant human IL-12 mitigates radiation-induced injury in NHP, an animal model that is closely related to human. Importantly, for the FDA Animal Rule path to approval, allometric dose conversion from mice to rhesus monkey allowed identification of comparable doses that provided similar recombinant human IL-12 exposure in monkeys. Despite similar PK characteristics, the IFN-γ response to recombinant human IL-12 appeared to be stronger in monkeys compared to mice. The fact that the percentage of survival of rhesus monkeys was similar after receiving either a single dose or two doses of recombinant human IL-12 at either 100 ng/Kg or 250 ng/Kg suggest that recombinant human IL-12 is likely to be effective at even lower doses. Importantly, the recombinant human IL-12 doses used in the NHP studies correspond to human doses of about 30 ng/Kg and 80 ng/Kg, respectively. In cancer patients, IL-12 has been administered intravenously, intraperitoneally, or subcutaneously at a dose range of 3 ng/Kg to 600 ng/Kg as a monotherapy or part of a combination therapy for the treatment of various carcinomas.

Subcutaneously, IL-12 is generally well tolerated when it is administered twice weekly at a range of 300 ng/Kg to 500 ng/Kg for up to 3 years. In our studies, recombinant human IL-12 was also well tolerated in monkeys after a single dose or up to seven doses of 1000 ng/Kg (data not shown) with no overt sign of toxicity.

The studies in monkeys, coupled with the very low effective dose in both mice and monkeys, indicate that the requisite recombinant human IL-12 dose for radiomitigation will be substantially lower than the IL-12 doses previously used in cancer patients, thus suggesting a more favorable safety profile for recombinant human IL-12 in radiation victims Given the expected safety profile for recombinant human IL-12, it is envisioned that the drug could be disseminated to all individuals in the vicinity of a radiological event, even in the absence of any knowledge of the actual level of radiation exposure.

As shown in this study, potent radiomitigation effects in mice and NHP can be achieved using very low, nanogram per kilogram doses of recombinant human IL-12 given merely once. The single, very low dose of recombinant human IL-12 required for its radiomitigation effects underscores both its potency and its expected safety in humans.

These findings indicate that recombinant human IL-12 may serve as a novel intervention for use as a frontline treatment to mitigate death due to radiation injury. First-in-human, phase I studies are ongoing to assess the safety and pharmacokinetic and pharmcodynamic profiles of recombinant human IL-12, along with further efficacy studies in animals. The culmination of these human and animal studies will allow a determination of the predictive efficacious dose of recombinant human IL-12 in humans under the Animal Rule, where efficacy is determined in animal models and safety is determined in humans.

Example 21

Exemplary Tissue Radioprotection with Administration of IL-12

IL-12 is evaluated clinically as a radioprotective agent for the prevention of early and late effects and tissue responses following radiotherapy (RT) for cancer in suitable subjects. Suitable subjects may include, for example, human, mice, rats, guinea pigs, dogs, or primates, including rhesus monkeys. Radiotherapy (RT) can include single or fractionated doses of heavy charged particles (e.g. X-rays), fission-spectrum neutrons, or gamma rays.

For example, IL-12 is evaluated clinically as a radioprotective agent for the prevention of radiation induced damage, including alopecia, xerostomia and mucositis for subjects receiving radiotherapy (RT) for head and neck cancer, using a rat RT model to examine the protective effects of IL-12 after IV and subcutaneous (SC) administration in a mucositis model. Rats (5 per group) are given 1-100 ng/kg of human dose equivalent) of IL-12 in either IV or SC, and their head and neck regions are exposed to 15.3 Gy of gamma radiation at 0.5, 2, 4, and 8 hours after IL-12 administration. Doses of 1-50 Gy may also be used. For 1-10 days after treatment, the oral cavities of the rats are examined for signs of mucositis. Mucosal erythema and mucosal edema are scored according to 0 through 5 and 0 through 2 scales, respectively, with the scores added to indicate overall mucositis. The average mucositis score for the untreated animals is calculated. Rats are protected from mucositis up to a few hours when given 11-12 either IV or SC. Rats that receive IL-12 SC, but not IV, also are protected from mucositis a few hours after administration. Similar histopathological and functional assessment are performed in the determination of protection against alopecia and xerostomia.

Other radiation-induced damage from radiation therapy were also determined following single dose or fractionated irradiation, and include, for example, xerostomia, mucositis and/or alopecia to assess the protective effects of IL-12 treatment when administered in conjunction with irradiation therapy for head and neck cancer. The occurrence of esophagitis and pneumitis may be used, for example, to assess the protective effects of IL-12 treatment in conjunction with radiation treatment of thoracic cancers. Effects on lower gastrointestinal mucositis or dermatitis following irradiation treatment for pelvic cancers may be used, for example, to assess the protective effects of IL-12 treatment in conjunction with radiation treatment of abdominal or pelvic cancers, including kidney, stomach, pancreas (e.g. pancreatic), gall bladder, bladder, prostate or gynecologic cancers. Effects on lower gastrointestinal mucositis can include rectal and urinary toxicities. In addition, survival level, LRG5 expression (as measure of GI injury marker), bone marrow injury (as measured by platelet, leukocyte, and reticulocyte count), histopathology assessment, cell, tissue or organ specific proteomic or molecular markers, apoptosis, or tissue or organ edema may also be used to assess radiation protection effects. In one embodiment, exemplary IL-12 compositions and treatment methods were efficacious in preventing and/or mitigating the radiation-induced side-effects associated with various radiation based therapeutic modality in the treatment of pancreatic cancer.

The respective biological endpoints in subjects such as rhesus monkeys and mice exposed to about 5-50 Gy of TBI, e.g., 6.7 Gy of TBI or equivalent fractionation at clinically relevant doses (e.g. at about 0.1 to about 2 Gy per fraction) is determined following treatment with 100 ng/Kg or 250 ng/Kg of recombinant human IL-12 (or equivalent dose of recombinant murine IL-12 doses of 8 ng/mouse and 20 ng/mouse).

In one arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days prior to each radiation dose in fractionated regimens of 1 to 10 doses/day for up to 30 days, administered either as TBI or locally, using each respective radiation source.

In another arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days after each radiation dose in fractionated regimens of 1 to 10 doses/day for up to 30 days, administered either as TBI or locally, using each respective radiation source.

In another arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days both before and after each radiation dose in fractionated regimens of 1 to 10 doses/day for up to 30 days, administered either as TBI or locally, using each respective radiation source.

Example 22

Protection from Acute Radiation-Induced Mucositis

Oral mucositis is induced in test subjects (e.g. monkeys or mouse) by administering a radiation dose of 1 to 50 Gy, in either a single dose or multiple fractions. On day 0, under anesthesia the left buccal pouch is harvested, fixed, and radiated while the rest of the animal is shielded with lead cover. Radiation is generated using an X-ray, neutron, or gamma sources at appropriate focal distances.

IL-12 composition is administered according to example 21 in appropriate routes of administration (e.g. daily subcutaneous injection starting five days before (day −5) radiation, and 15 days afterwards (day +15). A control group consisted of irradiated animals dose with vehicle only on days −5 to +15.

Mucositis Evaluation:

The progression of mucositis is monitored daily. Every other day starting on day 6 postirradiation, animals are anesthetized and the left buccal pouch is harvested and photographed. At the conclusion of the study's clinical phase, film is developed, and resulting photos are randomly numbered and then scored in blinded fashion by two observers. A 0-5 scoring system is used that applied the following numerical score to buccal lesions:

0, normal mucosa;
1, erythema and vasodilation;
2, severe erythema and vasodilation, with erosion of superficial aspects of mucosa leaving denuded areas with decreased stippling of mucosa.
3, severe erythema, vasodilation, and formation of ulcers in one or more places. Cumulative size of ulcers involves 25% of the pouch mucosa. Pseudomembrane formation is evident.
4, severe erythema and vasodilation. Cumulative size of ulcers involves about half of the pouch mucosa. Loss of mucosal pliability.
5, diffuse, extensive ulceration. Loss of pliability, pouch can only partially be extracted from mouth.

In this model, a score of 3 coincides with a clinically significant National Cancer Institute or WHO score 3. Severity of oral mucositis (OM) is calculated using the scores per treatment group on each observation day (mean±SE). Using the severity scores, results are also represented as percentage of days with a score of three or above.

The initial results demonstrate significant radioprotection at the relevant dose by various administrations of IL-12 in all fractionation or single dose irradiation modalities.

Example 23

Radiation Protection of IL-12 in Esophagus

Esophagitis is a significant toxicity of radiation therapy of thoracic cancers. We examine the radiation protective effects of IL-12 in the mouse esophagus. IL-12 is administered to mice by tube-feed swallow of a liposome formulation. Normal mice are treated with IL-12 with a dose according to Example 21 immediately prior to 28 Gy upper body irradiation. Following irradiation, esophagitis is assessed by excising the esophagus, and separating esophageal progenitors (SP) and differentiated (NSP) cells by cell sorting. IL-12 may also be administered after radiation therapy, in combination with or instead of IL-12 administration before irradiation.

Additional mice are administered 3LL cells intratracheally to induce orthotopic carinal lung tumors. Mice with lung orthotopic tumors are treated with intraesophageal IL-12 prior to receiving 20 Gy upper body irradiation. IL-12 may also be administered after radiation therapy, in combination with or instead of IL-12 administration before irradiation. Il-12 uptake in liver, peripheral blood and lung orthotopic tumor at 10, 30 and 60 minutes after intraesophageal administration is quantified. The esophagus is excised and esophageal progenitors (SP) and differentiated (NSP) cells are separated by cell sorting.

Results are also obtained showing that IL-12 ameliorates radiation-induced esophagitis without compromising radiation therapeutic efficacy. Mice receiving IL-12 prior to 28 Gy upper body irradiation show increased survival compared to mice that receive irradiation only. Lung orthotopic tumor bearing mice that received IL-12 immediately prior to 20 Gy upper body irradiation demonstrate increased survival compared to mice that received irradiation alone.

Example 24

Exemplary Tissue Radioprotection with Administration of IL-12

IL-12 is evaluated clinically as a radioprotective agent for the prevention of radiation induced toxicity following radiotherapy, including electron beam irradiation, for the treatment of CTCL in suitable subjects. Suitable subjects may include, for example, human, mice, rats, guinea pigs, dogs, or primates, including rhesus monkeys. Radiotherapy (RT) can include local or total skin electron beam irradiation (including high dose rate and low dose rate). For example, IL-12 is evaluated clinically as a radioprotective agent for the prevention of radiation induced damage, including erythema, ulceration, alopecia, dry skin, hyperpigmentation, ocular irritation, and temporary loss of fingernails for subjects receiving electron beam therapy (local and total skin), using a rat RT model to examine the protective effects of IL-12 after IV and subcutaneous (SC) administration.

Rats (5 per group) are given 1-100 ng/kg of human dose equivalent) of IL-12 in either IV or SC, and their affected regions are exposed to 4 Gy to 36 Gy of electron beam radiation at 0.5, 2, 4, and 8 hours after IL-12 administration. Doses of 1-50 Gy may also be used. For 1-10 days after treatment, the relevant tissues of the rats are examined for signs of radiation cytotoxicity.

Radiation induced cytoxicity listed above are scored according to 0 through 5 and 0 through 2 scales, respectively, with the scores added to indicate overall condition.

The average score for the untreated animals is calculated. Rats are protected from the side effects up to a few hours when given Il-12 either IV or SC. Rats that receive IL-12 SC, but not IV, also are protected from the side effects a few hours after administration. Similar histopathological and functional assessment are performed in the determination of protection against other cytotoxic endpoints.

The respective biological endpoints in subjects such as rhesus monkeys and mice exposed to about 1-50 Gy of electron beam radiation, is determined following treatment with 100 ng/Kg or 250 ng/Kg of recombinant human IL-12 (or equivalent dose of recombinant murine IL-12 doses of 8 ng/mouse and 20 ng/mouse).

In one arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days prior to each radiation dose in fractionated regimens of 1 to 10 doses/day for up to 30 days, administered either as TSEBT or locally, using each respective radiation source.

In another arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days after each radiation dose in fractionated regimens of 1 to 10 doses/day for up to 30 days, administered either as TSEBT or locally, using each respective radiation source.

In another arm of the study, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days both before and after each radiation dose in fractionated regimens of 1 to 10 doses/day for up to 30 days, administered either as TSEBT or locally, using each respective radiation source.

Example 25

Exemplary TSEBT Treatment Regimen

In an exemplary protocol, TSEB is administered using a technique similar to the technique originally developed at Stanford University (Hoppe et al., Hematologic Therapy, v16, 347-354; 2003). An exemplary 6 MeV six dual field technique is used, with the patient standing in six angular orientations about a vertical axis so the entire body surface is exposed to the beam. The positions are divided into a two-day cycle. On day 1 the patient is treated with a perpendicular anterior field and two oblique posterior fields and on day 2 a perpendicular posterior field and two oblique anterior fields. For each of the six positions two gantry angles are used. The two gantry angles, 90° and 19°, are chosen so that the central axis would pass above and under the patient thus avoiding the x-ray fluence of a forward directed beam. The field size is set to 40 cm/40 cm, the dose rate is 888 MU/min (at a distance of 1.6 m), which corresponds to 1.3 Gy/min in the center of the patient plane. The treatment of one field would take approximately 30 s.

In fields where the patient's face is turned towards the accelerator, eye shielding consisting of 3 mm lead is used (except in patients who had been operated for cataract). Starting about midway through the treatment, the toes and fingers are shielded with 3 mm lead to avoid overdosing.

The treatment is given with a source to skin distance of 370 cm with the patient standing about 20 cm behind a 0.5 cm thick, 12 m 2 acrylic panel. The panel works as an energy degrader, which means that the depth dose falls off closer to the body surface yielding a better dose in the most superficial parts of the skin. The panel also improves the dose uniformity, especially on oblique surfaces. Supplemental treatment is given to portions of the body surface that are shadowed and received relatively lower doses, such as the scalp, the perineum, the soles of the feet, and areas underneath the breasts or other skin folds. Typically, 6 MeV electron therapy with 1 cm of bolus is given to these areas. Patients with thick (up to 2 cm) tumors were treated with local electron fields, usually 15 Gy in 5 fractions, before start of TSEBT. In this situation, in our experience, the tumors often shrunk during treatment and became so thin at the end of treatment that a complete remission was obtained. Patients treated with high-dose TSEBT received a total dose of 30 Gy with 20 Gy as supplemental treatment to shadowed areas. Patients treated with low-dose TSEBT received a total dose of 4 Gy with 4 Gy as supplemental treatment to shadowed areas.

Accordingly, radioprotective efficacy of the IL-12 treatment is determined for patients from each of the following categories: Mycosis fungoides; Mycosis fungoides variants and subtypes; Folliculotropic mycosis fungoides; Sezary syndrome; Primary cutaneous aggressive epidermotropic CD8_T-cell lymphoma (provisional); Cutaneous g/d T-cell lymphoma (provisional); Primary cutaneous CD4_small/medium size pleomorpic T-cell lymphoma (provisional).

Exemplary P6N Formulation

At least 100 µL of a 100 µg/mL solution of exemplary mouse recombinant IL-12, a heterodimer made up of subunits coded for by separate subunits p35 (IL-12A gene) and p40 (IL-12B gene), is formulated in 20 mL of the IL-12 vehicle P6N (Neumedicines, Pasadena, Calif.). Prior to injection, the 100 µg/mL solution of IL-12 is diluted with either (1) 1/100 with P6N to provide a 1 µg/mL, 1 ng/µL, dosing solution, or (2) 1/1000 with P6N to provide a 0.1 ng/mL, 100 µg/µL, dosing solution or (3) 1/10,000 with P6N to provide a 0.01 ng/mL, 10 pg/µL dosing solution. The resulting three solutions following dilution are swirled or tapped gently and then used (e.g. injected) immediately.

Example 26

Clinical Trial

A clinical trial was conducted, demonstrating the efficacy of human and mouse recombinant IL-12 in mitigating radiation-induced normal tissue damage while providing anti-tumor responses in synergy with the Electron beam therapy (EBT) for the treatment of CTCL.

In this study, healthy volunteers received a single subcutaneous injection of 2, 5, 10, 12, 15 or 20 ng recombinant human and/or murine IL-12 in 6 cohorts. Each cohort included 2 sentinel subjects (Group 1) followed by 4 more subjects (Group 2) if the sentinel subjects did not present with any dose-limiting toxicities following a 7-day observation period. Subjects in Group 1 in each cohort were randomized to receive placebo or recombinant human and/or murine IL-12 at the ratio of 1:1. Subjects in Group 2 in each cohort were randomized to receive placebo or recombinant human and/or murine IL-12 at the ratio of 1:3, respectively. Toxicities were graded according to the FDA-modified Toxicity Grading Scale for Healthy Adult and Adolescent Volunteers Enrolled in Preventive Vaccine Clinical Trials.

Patients suffering from CTCL were monitored for any dose-limiting toxicity before the dose escalation per the pre-defined Dose Escalation/Stopping Rules, which were defined in the protocol as a single Grade 3 (severe) adverse event or two or more Grade 2 (moderate) adverse events attributable to recombinant human and/or murine IL-12. Thirty-two subjects were enrolled and completed the study, including 19 males (59%) and 13 females (41%) ranging in age from 18 to 44 years. The majority of subjects were Caucasians (81%).

The safety and tolerability profile of recombinant human and/or murine IL-12 was found to be acceptable among healthy volunteers at single subcutaneous (sc) doses of 2, 5, 10 and 12 µg. There were no deaths, serious adverse events or withdrawals due to adverse events.

Pharmacokinetic parameters of recombinant human and/or murine IL-12 following increasing doses at 2, 5, 10, 12, 15 and 20 µg resulted in greater exposure as indicated by increasing values for Cmax. Pharmacodynamic response to recombinant human and/or murine IL-12 was measured by quantifying IFN-γ levels over time following 2, 5, 10, 12, 15 and 20 µg doses.

In this study, sixty subjects, 18 to 45 years of age, were randomized to receive either recombinant human and/or murine IL-12 or placebo in a 4:1 ratio. Results of blinded data to date from this study confirm the safety of the 12 µg subcutaneous dose of recombinant human and/or murine IL-12 (approximately 177 ng/kg for a 70 kg subject) found optimum in the Phase 1a study. Importantly, the equivalent monkey dose to the 12 µg human dose, which is about 500 ng/kg, was demonstrated to be efficacious in increasing survival of lethally irradiated monkeys, as well as providing radioprotection of certain tissues, such as the gastrointestinal and bone marrow tissues.

Moreover, additional secondary endpoints were determined in the trial. Secondary endpoints include 1) the response rate (complete/partial) in CTCL patients treated with recombinant human and/or murine IL-12; 2) the frequency of refractory disease in patients treated with recombinant human and/or murine IL-12; 3) immune and cytokine response over time in patients treated with this treatment regimen; and 4) the frequency of improved clinical response in patients treated with this treatment regimen.

Furthermore, the biologic correlates of response, including levels of IFN-γ production, natural killer cell activity, infiltration of skin lesions by CD8-positive cells, lymphocyte IL-12Rβ2 expression, signal transducers and activators of transcription protein levels and IL-12 signal transduction, and induction of apoptosis in tumor cells in the skin of patients treated with this dosing regimen are assessed.

Example 27

Efficacy Studies of Exemplary rIL-12 Using Various Endpoints

The efficacy studies of exemplary rIL-12 using various endpoints (survival 15, decreased hemorrhage 16, BM regeneration 17-19, desrease sepsis 20, secondary endpoints 21 (lymphocyte neutrophil, platelet counts), and RCI radiation combined injury were demonstrated.

In the Dose Range Finding Study: the survival benefit at LD90 in rhesus monkeys in the absence of supportive Care, GLP, blinded were shown:
1. sample No. n=90; 18/group (9 Male, 9 Female);
2. irradiation received=7.0 Gy, LD90;
3. exemplary recombinant human IL-12 (HemaMax Product) was prepared in accordance with GMP in P6NF formulation.
4. administration: 1× SC (subcutaneous) injection; 50-500 ng/kg of rIL-12 formulation at 24-25 hrs post-radiation;
5. no Supportive Care: Fluids, antibiotics, or blood products; and
6. statistical significance: each treated groups vs. control p<0.04.

Figure 15:
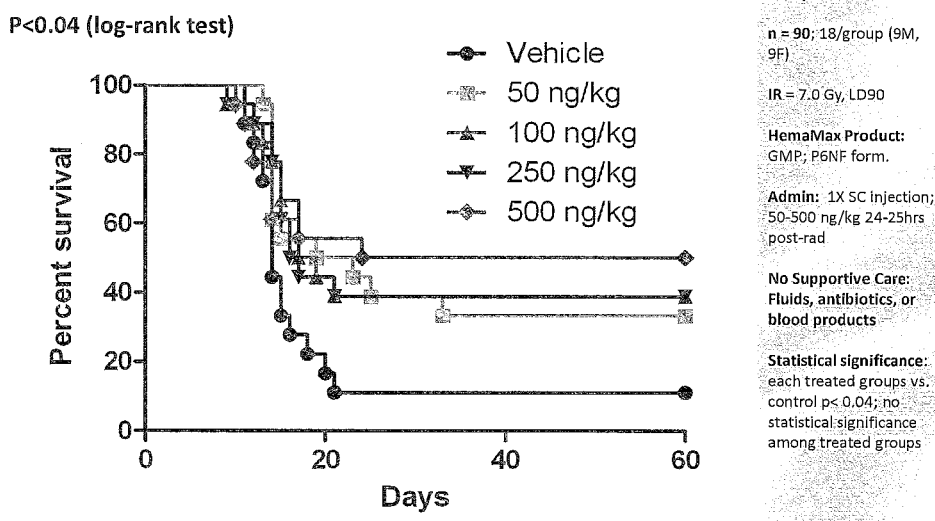
FIG. 15A-15B. Demonstration of efficacy of exemplary IL-12 in achieving 3. 5-Fold Increase In Survivors After Exposure To Radiation (LD90). Results from dose range finding study showed survival benefit at LD90 in Rhesus monkeys in the absence of supportive care. All protocols were carried out in accordance with GLP; data was obtained based on a Blinded study design.

As shown in FIG. 15, the efficacy of the exemplary IL-12 formulation/composition was demonstrated in its ability to achieve about 3. 5-fold Increase in survivors after exposure to radiation (LD90).

Figure 16:
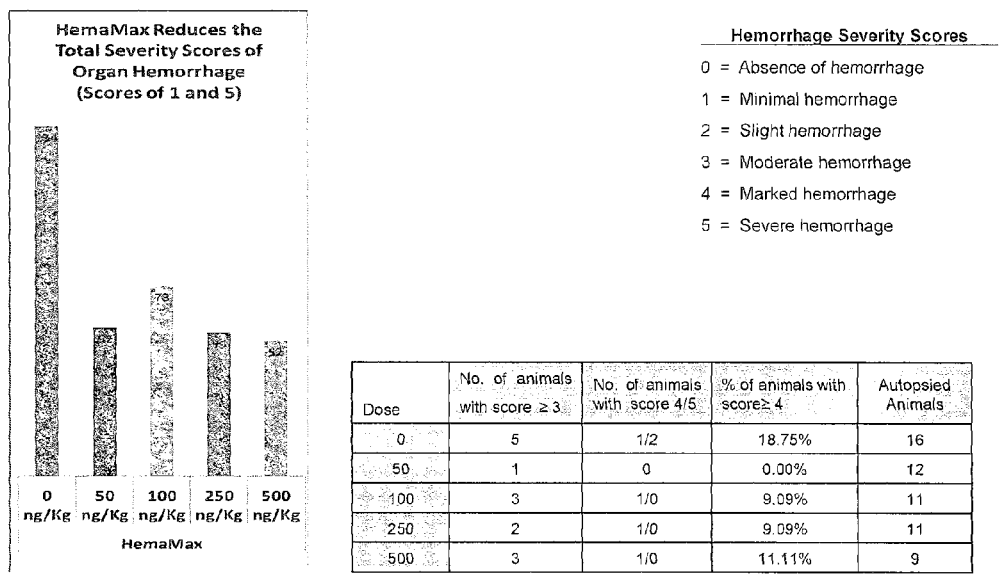
FIG. 16. Demonstration that Exemplary IL-12 (HemaMax) Treatment Is Associated with Decreased Hemorrhage Scores in Irradiated NHP (LD90/60).

As shown in FIG. 16, the efficacy of the exemplary IL-12 formulation/composition was demonstrated in its ability to decrease hemorrhage.

Figures 19A, 19B, 19C:
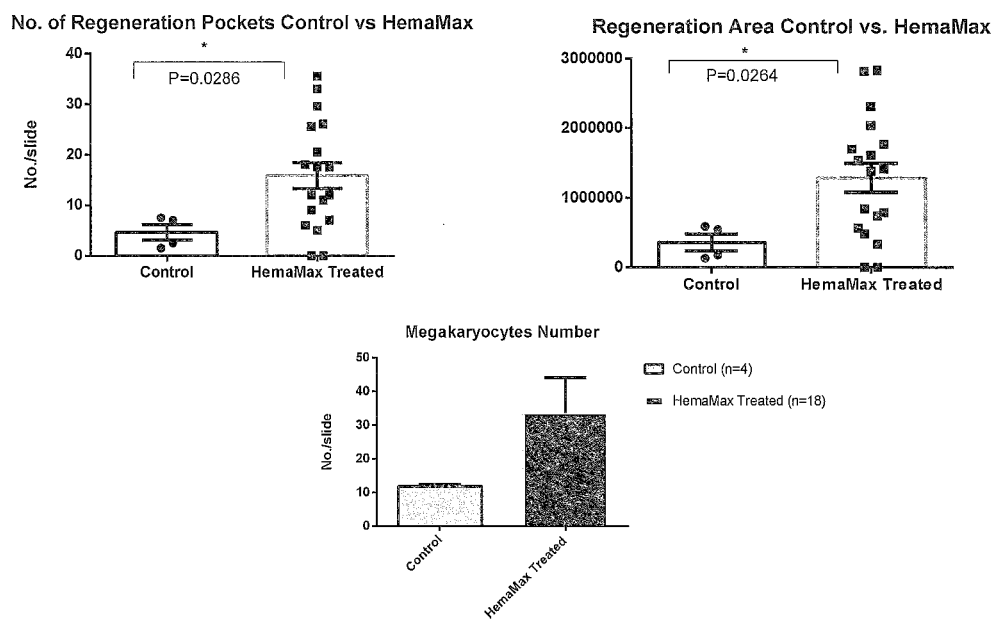
FIG. 19 A-19C. Another Illustration Of Efficacy Of rIL-12 HemaMax In Stimulating BM Regeneration Following Lethal Radiation Exposure.

As shown in FIGS. 17-19, the efficacy of the exemplary IL-12 formulation/composition was demonstrated in its ability to induce bone marrow regeneration.

Figure 20:
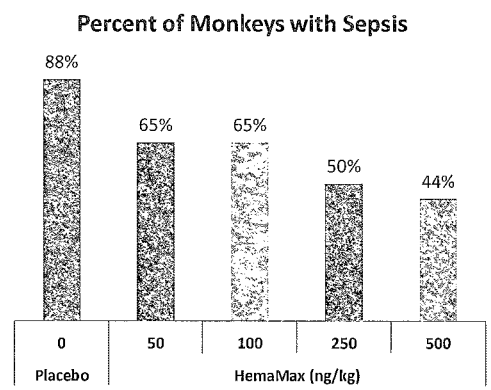
FIG. 20. Demonstration of efficacy: rIL-12 HemaMax Treatment is Associated with Decreased Incidence of Sepsis in Irradiated NHP.

As shown in FIG. 20, the efficacy of the exemplary IL-12 formulation/composition was demonstrated in its ability to decrease sepsis.

Figure 21A:
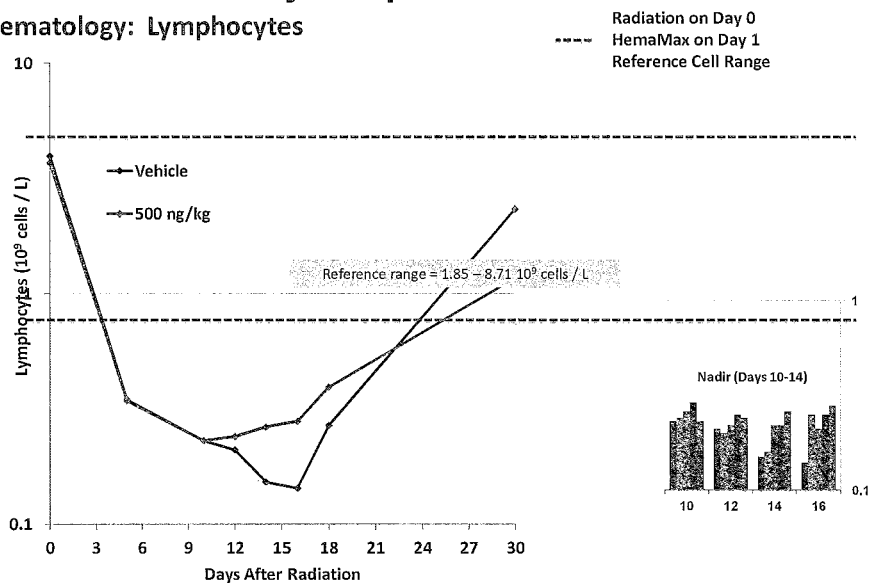
FIG. 21A-21C. Demonstration of rIL-12 efficacy based on various Secondary Endpoints.
Figure 21B:
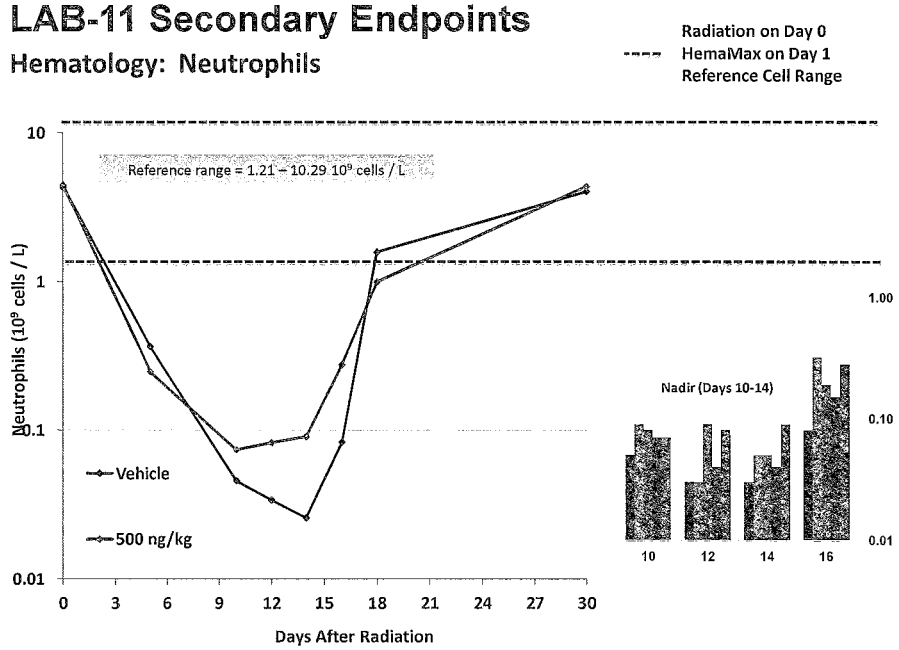
Figure 21C:
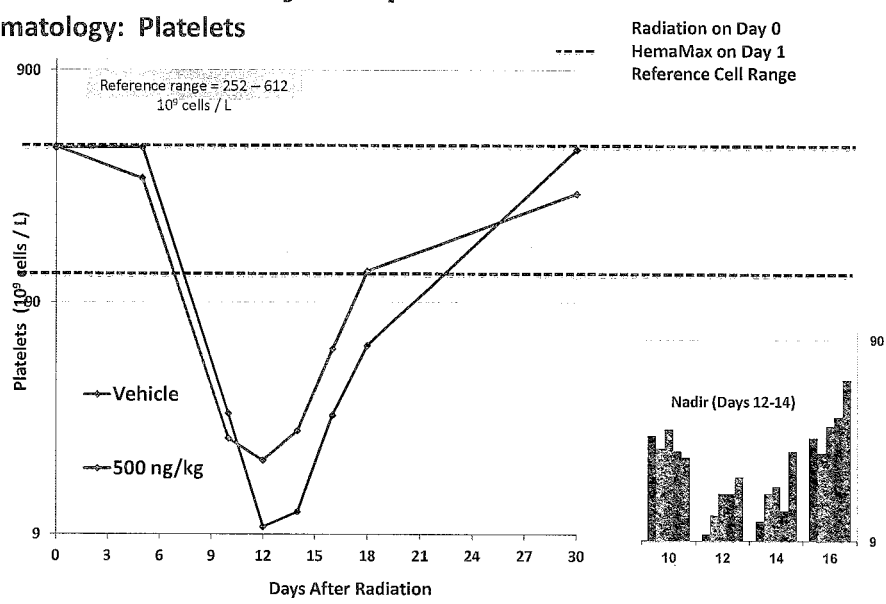

As shown in FIGS. 21A-C, the efficacy of the exemplary IL-12 formulation/composition was demonstrated in its ability to facilitate recovery of lymphocytes, neutrophils and platelets.

Figures 22A, 22B, 22C:
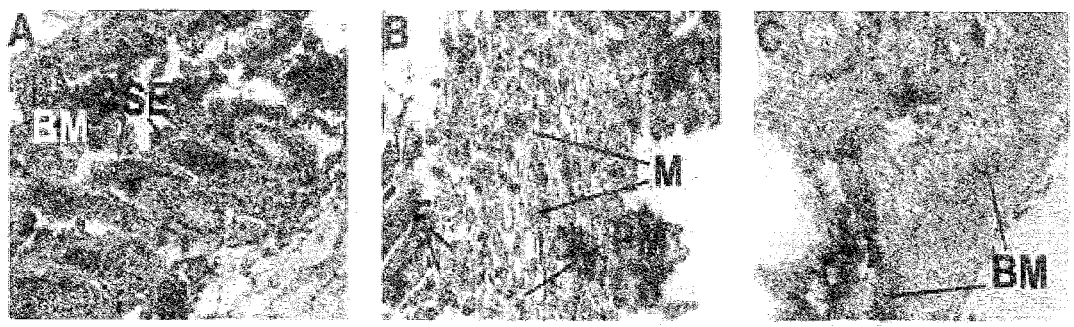
FIG. 22 A-22C. Demonstration of efficacy of HemaMax for Radiation Combined Injury (RCI).

As shown in FIG. 22, the efficacy of the exemplary IL-12 formulation/composition was demonstrated in its ability to facilitate recovery from RCI radiation combined injury. In RCI studies, a single, low dose of the murine counterpart to HemaMax (rMuIL-12) administered at 24 hours post radiation was found to increase the rate of wound closure, enhance skin remodeling, and increase survival following lethal radiation exposure, compared to placebo-treated mice. This is the first demonstration of the multipurpose, broad spectrum therapeutic potential of HemaMax as a Rad-MCM. In FIG. 22A-C, a previously unidentified role for IL-12 in the stimulation of wound healing is demonstrated in normal, uninjured (A) and wounded, irradiated skin tissue (B and C). In uninjured skin, the IL-12 receptor is found to be highly expressed on progenitor cells in the basement membrane of the dermis and in sebaceous glands underlying hair follicles. These progenitor cells are the primary mediators of re-epithelialization following cutaneous injury. The figure below further demonstrates that following full-thickness injury, which is equivalent to a third degree burn, the IL-12 receptor is highly upregulated in expression at the wound surface. These data show that injured skin is primed for stimulation by HemaMax (rHuIL-12) following cutaneous injury to yield early wound closure (see Data Quadrant of the attached Quad Chart). FIG. 1: Skin is "primed" for stimulation by murine IL-12: IL-12RB2, the receptor for HemaMax expression in (A) uninjured skin and (B, C) wound tissue from irradiated mice receiving full-thickness injury; (A) In non-irradiated, uninjured skin, IL-12RB2 is expressed in progenitor cells contained in the basement membrane (BM) of the dermis and in sebaceous glands (SEB) underlying hair follicles. BM and SEB derived progenitor cells are the primary mediators of re-epithelialization following cutaneous injury. (B) IL-12RB2, the receptor for HemaMax is upregulated in skin receiving full-thickness injury. Granulation tissue IL-12RB2 expressed predominately in macrophages (M), some expression noted in polymorphonuclear neutrophils (PMN), and fibroblasts (F). (C) Wound edge epithelium showing increased expression of IL-12RB2 in basement membrane cells 48 hrs post-irradiation/wounding. Data suggests accelerated entry into proliferative phase of wound healing.

Example 28

Efficacy Study in Wound Healing

Figure 23:
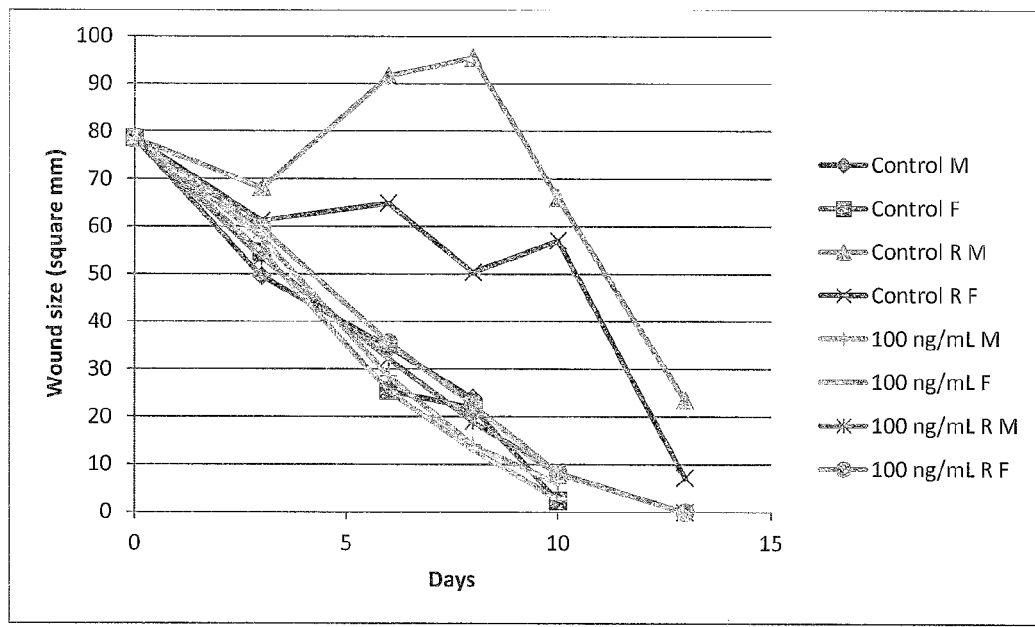
FIG. 23-25. Demonstration of the efficacies of rMuIL-12 in accelerating wound closure (decreasing wound size) and mitigating combined injury in irradiated mice (2-4 hrs Post-Exposure).
Figure 24:
Figure 25:
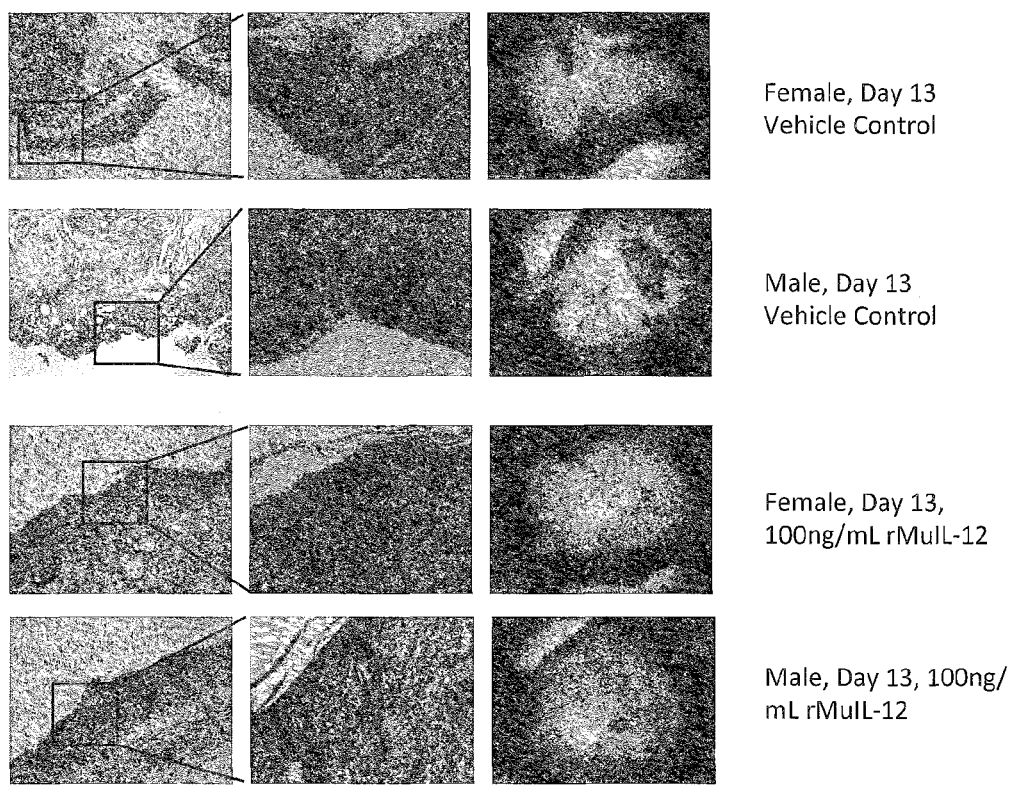

As shown in FIGS. 23, 24 and 25, the efficacies of rMuIL-12 in accelerating wound closure (decreasing wound size) and mitigating combined injury in irradiated mice (2-4 hrs Post-Exposure) were demonstrated.

Experimental model/protocol includes the following parameters:

C57Bl/6 mice (3-Female, 3-Male);

Subjects received 500cGy Total Body Irradiation;

10 mm full-thickness injury was induced on the back of the subjects and dressed with Tegaderm™;

Subjects were treated with topical administration of:

4% carboxymethylcellulose or 4% carboxymethylcellulose+rMuIL-12 (100 ng/mL) every 2-3 Days; and Subject wounds were measured, treated, and re-dressed as needed.

Example 29

24 Hour Mitigation Study: Wound Healing

Figure 26:
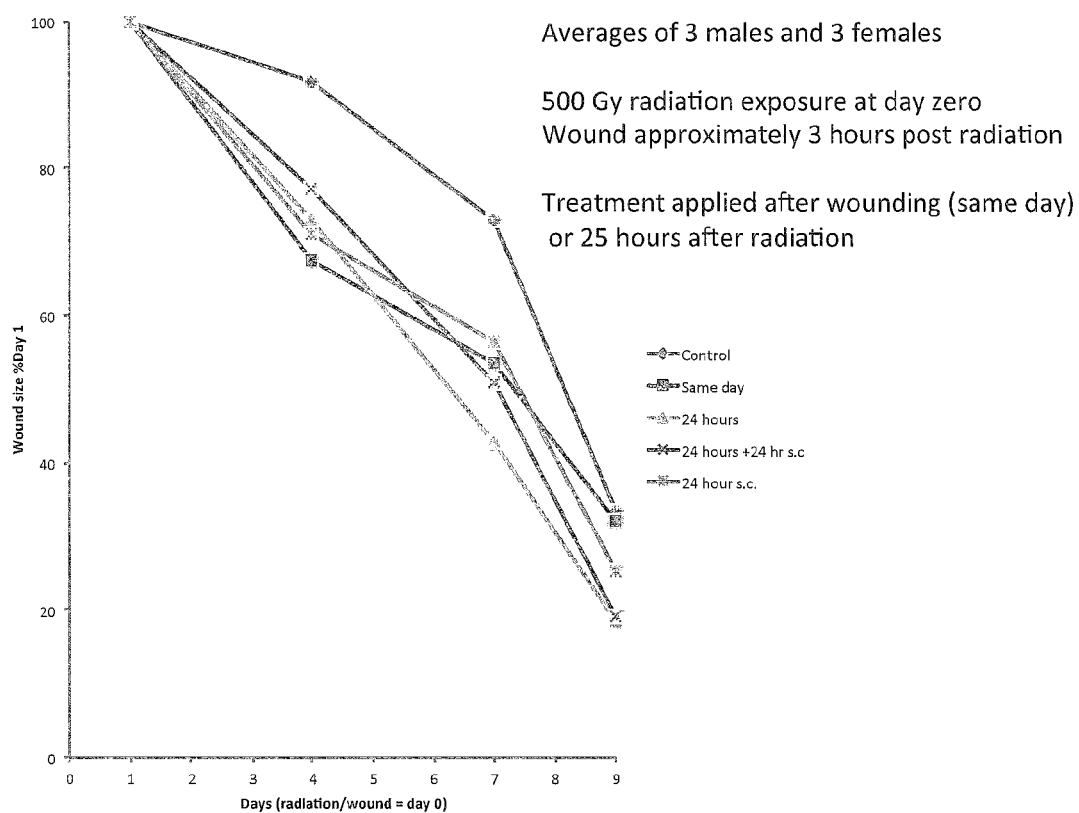
FIGS. 26-27. Demonstration of efficacy of rMuIL-12 in accelerating wound closure and mitigates combined injury in irradiated mice (24 hr Post-Exposure).
Figure 27:
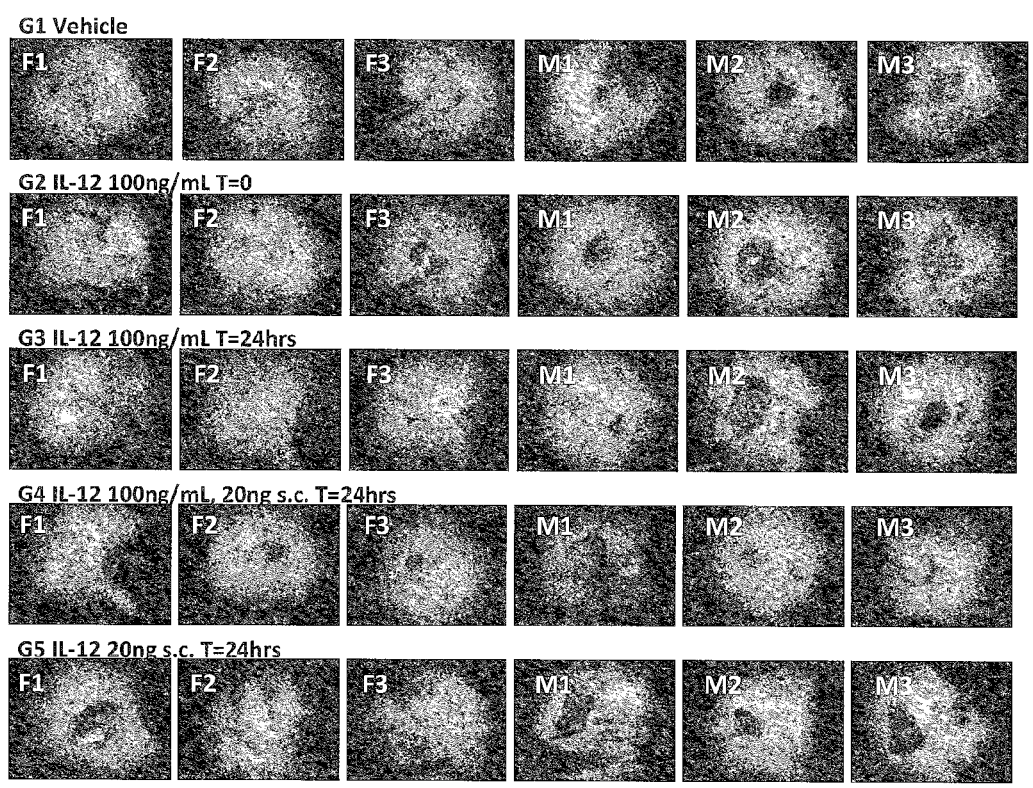
Figure 28:
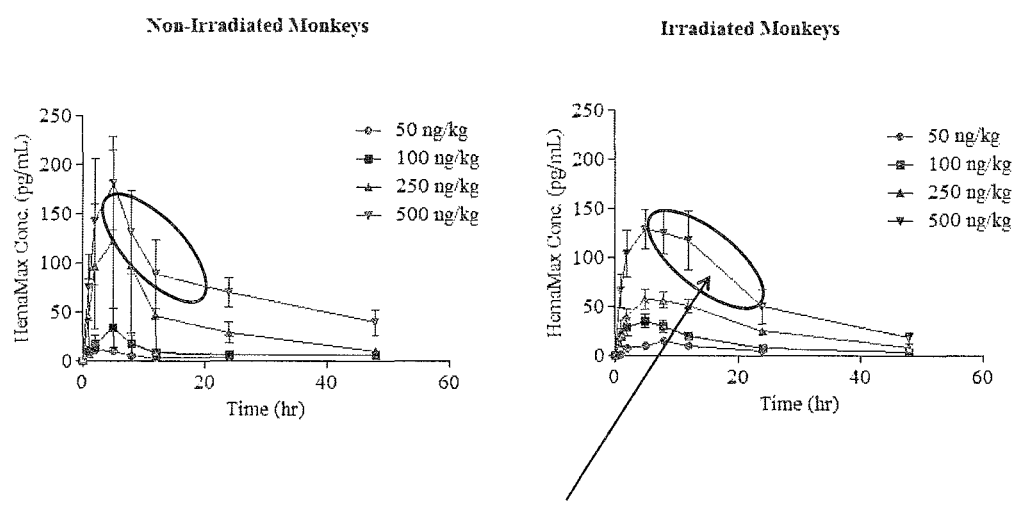
FIG. 28. Plasma Concentration-Time Profiles of HemaMax After a SC Dose in Non-Irradiated and Irradiated Monkeys.
Figure 29:
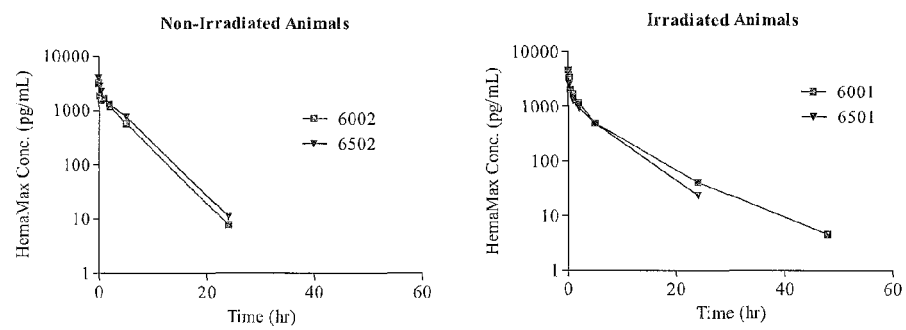
FIG. 29. Plasma Concentration-Time Profiles of HemaMax After an IV Dose (250 ng/kg) in Non-Irradiated and Irradiated Monkeys (Log Scale).
Figure 30:
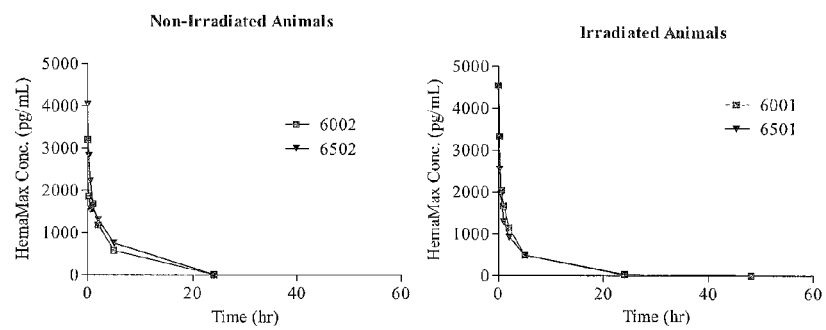
FIG. 30. Plasma Concentration-Time Profiles of HemaMax After an IV Dose (250 ng/kg) in Non-Irradiated and Irradiated Monkeys (Linear Scale).
Figure 32:
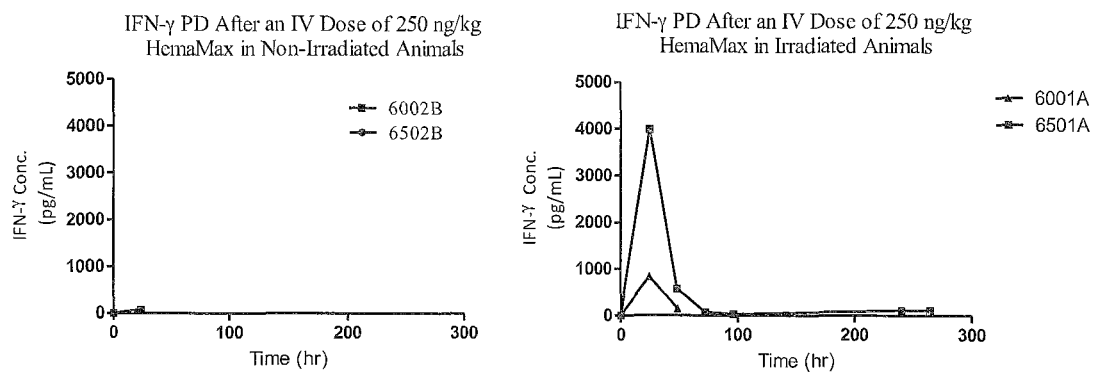
FIG. 32. Pharmacodynamics of IFN-γ After an IV Dose of HemaMax in Non-Irradiated and Irradiated Monkeys.
Figure 34:
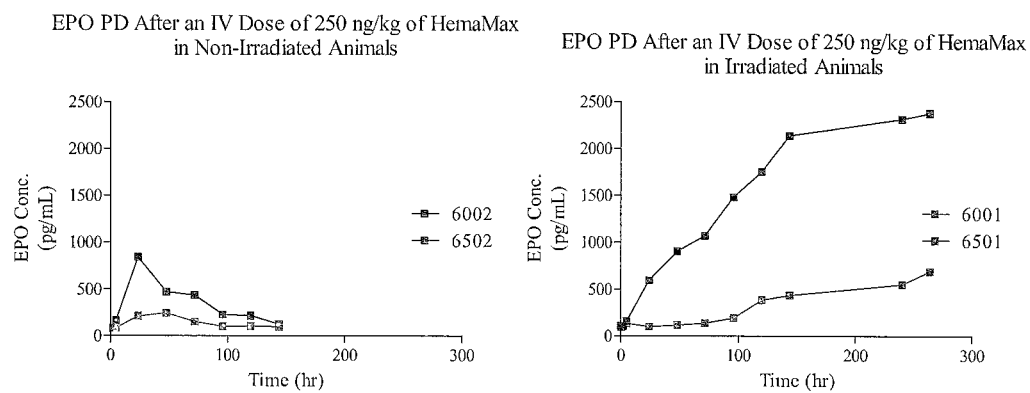
FIG. 34. Pharmacodynamics of EPO—After and IV Dose of HemaMax in Non-Irradiated and Irradiated Monkeys.
Figure 35:
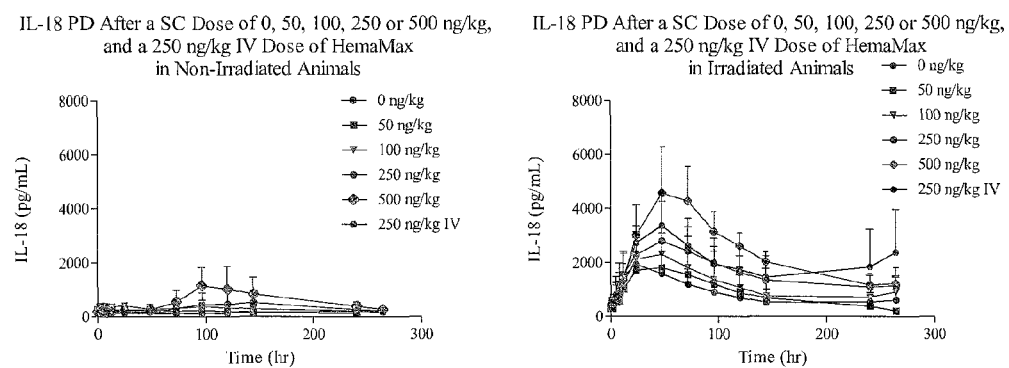
FIG. 35. Pharmacodynamics of IL-18—After a SC Dose of HemaMax in Non-Irradiated and Irradiated Monkeys.
Figure 36:
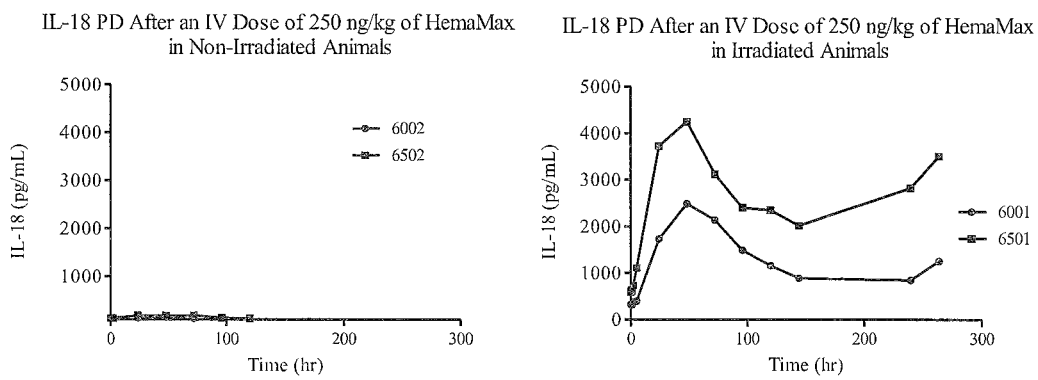
FIG. 36. Pharmacodynamics of IL-18—After an IV Dose of HemaMax in Non-Irradiated and Irradiated Monkeys.
Figure 37:
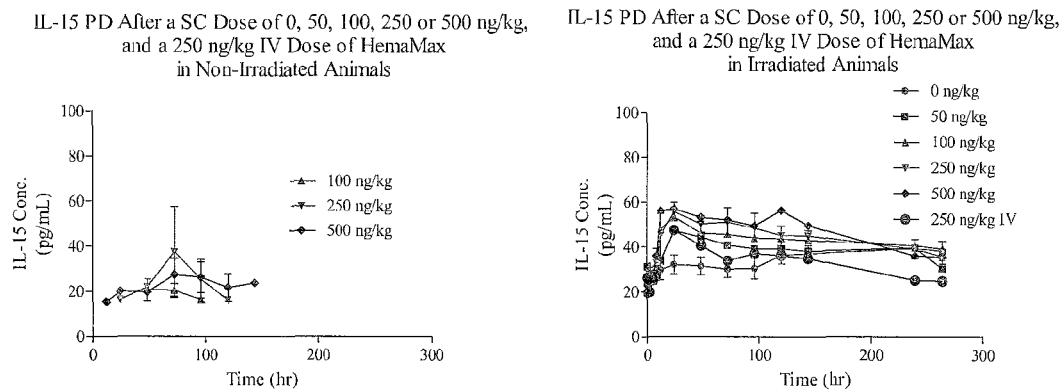
FIG. 37. Pharmacodynamics of IL-15—After a SC Dose of HemaMax in Non-Irradiated and Irradiated Monkeys.
Figure 38:
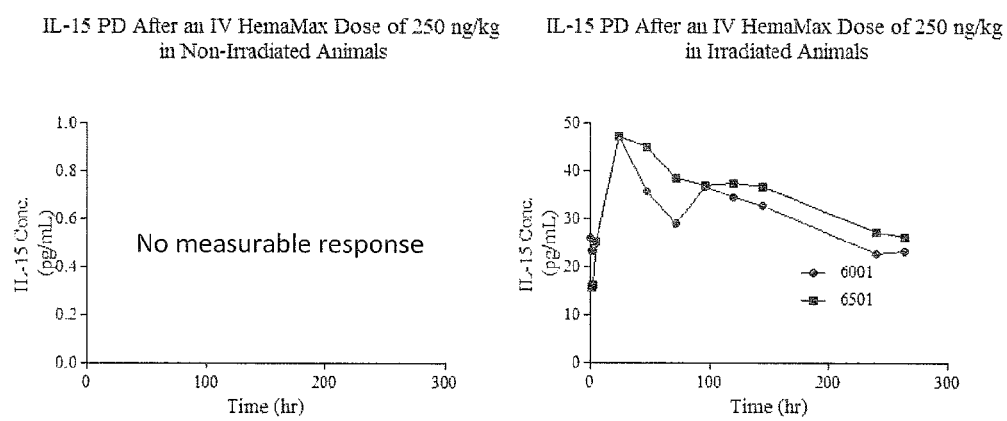
FIG. 38. Pharmacodynamics of IL-15—After an IV Dose of HemaMax in Non-Irradiated and Irradiated Monkeys.

As shown in FIG. 26-27, the efficacy of rMuIL-12 in accelerating wound closure and mitigates combined injury in irradiated mice (24 hr Post-Exposure) was demonstrated.

Model:Protocol Includes:

C57Bl/6 mice (3-Female, 3-Male)

Subjects were given 500cGy Total Body Irradiation 10 mm full-thickness injury were induced on the back of subjects;

Subjects were given Tegaderm™ dressing for cover wound area;

Treatments were given at 0-24 hrs post-Injury:

Treatment groups were treated as follows:

1. Group 1: 4% carboxymethylcellulose (Topical)
2. Group 2: 4% carboxymethylcellulose+Topical rMuIL-12 (100 ng/mL) Same Day
3. Group 3: 4% carboxymethylcellulose+Topical rMuIL-12 (100 ng/mL)×24 hrs
4. Group 4: 4% carboxymethylcellulose+Topical rMuIL-12 (100 ng/mL)×24 hrs+rMuIL-12 (20 ng) s. c.
5. Group 5: rMuIL-12 (20 ng) s. c.×24 hrs (single dose); and Subjects/wounds were measured, treated, and re-dressed as needed every 2-3 Days.

Example 30

Pharmacokinetic and Pharmacokinetic Studies

Recombinant human IL-12 (e.g. HemaMax™) pharmacokinetics (PK) and pharmacodynamics (PD) parameters in non-irradiated and irradiated monkeys were assessed. HemaMax was administered to monkeys with and without irradiation. In both sets of animals, the PK of HemaMax was similar; however, there was a slight trend for a longer half-life in irradiated animals. In general, pharmacodynamic markers suggested a more pronounced PD response after irradiation. In irradiated animals, the plasma concentrations of IFN-γ and IL-18 most clearly increased in a manner which reflected the corresponding increase in the HemaMax dose (see FIGS. 28-38).

Hemamax™ Pharmacokinetics and Pharmacodynamics in Non-Irradiated and Irradiated Monkeys Data:

Non-Irradiated Monkeys: HemaMax PK—SC Dosing

| Dose (ng/kg) | | $T_{max}$ (hr) | $C_{max}$ (pg/mL) | SC $T_{1/2}$ (hr) | $AUC_{last}$ (hr * pg/mL) | $AUC_{0-\infty}$ (hr * pg/mL) | AUC Extrap (%) | $V_z/F$ (mL/kg) | Cl/F (mL/hr/kg) | F (%) |
|---|---|---|---|---|---|---|---|---|---|---|
| 0 | Mean | NR | NR | NR | NR | NR | NR | NR | NR | NR |
|   | SD   | NR | NR | NR | NR | NR | NR | NR | NR | NR |
| 50 | Mean | 2.00 | 11.97 | 33.44 | 117.89 | 298.52 | 56.79 | 8079.54 | 167.49 | 7.02 |
|    | SD   | 0.00 | 3.35 | NR | 23.21 | NR | NR | NR | NR | NR |
| 100 | Mean | 5.00 | 33.62 | 31.14 | 357.18 | 782.83 | 29.20 | 4691.98 | 154.15 | 10.51 |
|     | SD   | 0.00 | 20.26 | NR | 239.46 | NR | NR | NR | NR | NR |
| 250 | Mean | 5.00 | 123.20 | 29.01 | 1875.17 | 1561.16 | 24.06 | 4666.41 | 102.24 | 15.53 |
|     | SD   | 0.00 | 92.51 | 17.56 | 948.56 | 718.46 | 19.49 | 3246.75 | 24.74 | 10.47 |
| 500 | Mean | 4.25 | 185.80 | 37.34 | 3756.09 | 6042.51 | 36.48 | 4532.00 | 86.70 | 13.28 |
|     | SD   | 1.50 | 50.73 | 14.30 | 909.47 | 1575.09 | 15.59 | 1761.08 | 20.53 | 3.91 |

Irradiated Monkeys: HemaMax PK—SC Dosing

| Dose (ng/kg) | | $T_{max}$ (hr) | $C_{max}$ (pg/mL) | SC $T_{1/2}$ (hr) | $AUC_{last}$ (hr * pg/mL) | $AUC_{0-\infty}$ (hr * pg/mL) | AUC Extrap (%) | $V_z/F$ (mL/kg) | Cl/F (mL/hr/kg) | F (%) |
|---|---|---|---|---|---|---|---|---|---|---|
| 0 | Mean | NR | NR | NR | NR | NR | NR | NR | NR | NR |
|   | SD   | NR | NR | NR | NR | NR | NR | NR | NR | NR |
| 50 | Mean | 8.00 | 14.65 | NR | 191.55 | NR | NR | NR | NR | 12.07 |
|    | SD   | 0.00 | 4.74 | NR | 90.08 | NR | NR | NR | NR | 4.12 |
| 100 | Mean | 5.00 | 39.03 | 9.06 | 535.09 | 599.22 | 12.53 | 2430.19 | 187.09 | 13.11 |
|     | SD   | 2.45 | 15.85 | 3.65 | 237.74 | 234.64 | 9.40 | 1471.26 | 72.54 | 4.42 |
| 250 | Mean | 7.50 | 69.49 | 15.82 | 1398.63 | 1579.89 | 13.08 | 3654.52 | 163.32 | 10.92 |
|     | SD   | 3.32 | 11.47 | 4.21 | 204.14 | 145.21 | 7.29 | 868.75 | 35.13 | 1.74 |

-continued

| Dose (ng/kg) | | $T_{max}$ (hr) | $C_{max}$ (pg/mL) | SC $T_{1/2}$ (hr) | $AUC_{last}$ (hr * pg/mL) | $AUC_{0-\infty}$ (hr * pg/mL) | AUC Extrap (%) | $V_z/F$ (mL/kg) | Cl/F (mL/hr/kg) | F (%) |
|---|---|---|---|---|---|---|---|---|---|---|
| 500 | Mean | 8.50 | 137.18 | 10.45 | 3019.79 | 2970.46 | 17.89 | 5003.27 | 198.38 | 12.23 |
|  | SD | 4.73 | 38.07 | NR | 1315.01 | NR | NR | NR | NR | 5.20 |

Non-Irradiated Monkeys: HemaMax PK—250 ng/kg IV

| Animal | $T_{1/2}$ (hr) | $AUC_{last}$ (hr * pg/mL) | $AUC_{0-\infty}$ (hr * pg/mL) | AUC Extrap (%) | $V_z$ (mL/kg) | Cl (mL/hr/kg) |
|---|---|---|---|---|---|---|
| 6002B | 3.04 | 8335.99 | 8370.11 | 0.41 | 131.18 | 29.87 |
| 6502B | 3.19 | 10267.32 | 10318.92 | 0.50 | 111.45 | 24.23 |
| Mean | 3.12 | 9301.66 | 9344.51 | 0.45 | 121.32 | 27.05 |

Irradiated Monkeys: HemaMax PK—250 ng/kg IV

| Animal | $T_{1/2}$ (hr) | $AUC_{last}$ (hr * pg/mL) | $AUC_{0-\infty}$ (hr * pg/mL) | AUC Extrap (%) | $V_z$ (mL/kg) | Cl (mL/hr/kg) |
|---|---|---|---|---|---|---|
| 6001A | 6.42 | 10090.08 | 10127.41 | 0.37 | 228.57 | 24.69 |
| 6501A | 4.21 | 8291.48 | 8432.41 | 1.67 | 180.03 | 29.65 |
| Mean | 5.31 | 9190.78 | 9279.91 | 1.02 | 204.30 | 27.17 |

Pharmacodynamics IFN-γ:
PD IFN-γ—Non-Irradiated Monkeys—IFN-γ Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 120.00 | 423.60 | 97.00 | 264.00 | 30199.20 | 91613.70 | 50.11 |
|  | SD | NR | NR | NR | NR | NR | NR | NR |
| 50 | Mean | 120.00 | 165.20 | 74.53 | 208.00 | 14250.40 | NR | NR |
|  | SD | 104.61 | 128.42 | 51.33 | 77.15 | 5967.28 | NR | NR |
| 100 | Mean | 56.00 | 776.40 | 287.07 | 264.00 | 99948.80 | 476796.36 | 54.49 |
|  | SD | 13.86 | 268.46 | 238.60 | 0.00 | 64826.62 | 571871.98 | 32.87 |
| 250 | Mean | 42.00 | 2372.90 | 39.50 | 198.00 | 97885.80 | 104759.42 | 13.61 |
|  | SD | 14.64 | 3419.37 | 8.29 | 76.84 | 113090.65 | 109655.68 | 18.95 |
| 500 | Mean | 75.00 | 4352.40 | 63.50 | 204.00 | 181754.10 | 159960.68 | 12.11 |
|  | SD | 42.00 | 3721.80 | 29.79 | 69.28 | 109175.84 | NR | NR |

Irradiated Monkeys IFN-γ Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 6.00 | 150.20 | 94.80 | 264.00 | 24868.80 | 57174.49 | 69.29 |
|  | SD | NR | NR | NR | NR | NR | NR | NR |
| 50 | Mean | 20.00 | 257.73 | 104.27 | 40.00 | 6239.20 | NR | NR |
|  | SD | 6.93 | 120.42 | 50.53 | 27.71 | 5395.40 | NR | NR |
| 100 | Mean | 18.00 | 709.60 | 98.40 | 126.00 | 22904.40 | 49025.62 | 33.71 |
|  | SD | 6.93 | 422.55 | 58.54 | 96.75 | 8449.72 | NR | NR |
| 250 | Mean | 21.00 | 1949.15 | 88.40 | 168.00 | 76621.50 | 74474.53 | 17.20 |
|  | SD | 6.00 | 1200.24 | 86.20 | 64.99 | 41016.18 | 41346.81 | 7.56 |
| 500 | Mean | 15.00 | 3094.00 | 87.40 | 228.00 | 123995.40 | 151638.12 | 11.13 |
|  | SD | 6.00 | 1195.79 | 55.13 | 57.13 | 42927.08 | 90874.26 | 16.06 |

Non-Irradiated Monkeys IFN-γ Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6002 | NC | 66.8 | NC | NC | NC | NC | NC |
| | 6502 | NC | 79.2 | NC | NC | NC | NC | NC |
| | Mean | NR | 73.0 | NR | NR | NR | NR | NR |

Irradiated Monkeys IFN-γ Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6001 | 24.00 | 836.00 | 150.00 | 48.00 | 21864.00 | NC | NC |
| | 6501 | 24.00 | 3984.00 | 112.80 | 264.00 | 124608.00 | 174153.42 | 28.45 |
| | Mean | 24.00 | 2410.00 | 131.40 | 156.00 | 73236.00 | 174153.42 | 28.45 |

Pharmacodynamics EPO:
Non-Irradiated Monkeys EPO Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 64.00 | 226.91 | 137.79 | 112.00 | 16556.78 | 28200.69 | 24.20 |
| | SD | 13.86 | 32.07 | 50.01 | 36.66 | 4288.68 | NR | NR |
| 50 | Mean | 88.00 | 935.12 | 145.04 | 176.00 | 62108.65 | 84325.87 | 7.82 |
| | SD | 27.71 | 736.19 | 79.40 | 55.43 | 32511.56 | 19575.65 | 6.05 |
| 100 | Mean | 72.00 | 320.30 | 113.37 | 184.00 | 37058.26 | 46237.55 | 21.88 |
| | SD | 63.50 | 179.40 | 8.53 | 69.28 | 12015.15 | 12660.13 | 15.36 |
| 250 | Mean | 54.00 | 1115.19 | 192.85 | 174.00 | 61387.60 | 108729.05 | 38.27 |
| | SD | 30.20 | 1089.58 | 147.21 | 60.00 | 50768.76 | 66907.34 | 28.14 |
| 500 | Mean | 66.00 | 797.89 | 164.19 | 168.00 | 58361.25 | 108731.00 | 30.01 |
| | SD | 53.22 | 562.57 | 83.84 | 48.00 | 38948.78 | 19702.13 | 38.44 |

Irradiated Monkeys EPO Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 264 | 3205.56 | 3205.56 | 264 | 324042.55 | NR | NR |
| | SD | 0 | 3095.86 | 3095.86 | 0 | 316845.53 | NR | NR |
| 50 | Mean | 258 | 1406.07 | 1343.73 | 264 | 174905.23 | NR | NR |
| | SD | 12 | 456.97 | 393.13 | 0 | 32466.81 | NR | NR |
| 100 | Mean | 264 | 3153.11 | 3153.11 | 264 | 401102.86 | NR | NR |
| | SD | 0 | 2357.37 | 2357.37 | 0 | 330930.55 | NR | NR |
| 250 | Mean | 228 | 2787.61 | 2783.31 | 234 | 281912.62 | NR | NR |
| | SD | 72 | 2565.27 | 2570.22 | 60 | 235460.61 | NR | NR |
| 500 | Mean | 228 | 2411.37 | 2342.82 | 264 | 227268.99 | NR | NR |
| | SD | 72 | 1927.46 | 2002.09 | 0 | 112616.83 | NR | NR |

Non-Irradiated Monkeys EPO Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6002 | 24.00 | 837.77 | 124.05 | 144.00 | 53763.75 | 63308.66 | 15.08 |
| | 6502 | 48.00 | 245.77 | 97.01 | 144.00 | 21064.05 | 38020.32 | 44.60 |
| | Mean | 36.00 | 541.77 | 110.53 | 144.00 | 37413.90 | 50664.49 | 29.84 |

Irradiated Monkeys EPO Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6001 | 264 | 699.21 | 699.21 | 264 | 90987.42 | NC | NC |
| | 6501 | 264 | 2375.92 | 2375.92 | 264 | 435130.08 | NC | NC |
| | Mean | 264 | 1533.07 | 1533.07 | 264 | 263058.75 | NR | NR |

Pharmacodynamics IL-18:

Non-Irradiated Monkeys IL-18 Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 140.00 | 176.61 | 167.87 | 264.00 | 34780.73 | NR | NR |
| | SD | 126.05 | 29.82 | 20.36 | 0.00 | 1686.55 | NR | NR |
| 50 | Mean | 84.00 | 235.63 | 137.67 | 192.00 | 31922.33 | 54287.14 | 40.62 |
| | SD | 16.97 | 22.41 | 24.78 | 67.88 | 1054.25 | 6716.47 | 9.29 |
| 100 | Mean | 88.00 | 381.93 | 176.60 | 224.00 | 60848.46 | 110626.75 | 48.46 |
| | SD | 13.86 | 230.90 | 59.24 | 69.28 | 49262.10 | 37814.82 | 32.78 |
| 250 | Mean | 96.00 | 477.56 | 199.08 | 228.00 | 75101.10 | 134995.86 | 31.85 |
| | SD | 19.60 | 458.64 | 120.09 | 72.00 | 70832.76 | 75601.59 | 19.21 |
| 500 | Mean | 108.00 | 1027.92 | 270.48 | 264.00 | 144166.64 | 220936.32 | 33.78 |
| | SD | 24.00 | 841.88 | 114.37 | 0.00 | 103218.01 | 74522.73 | 35.83 |

Irradiated Monkeys IL-18 Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 24.00 | 1920.75 | 608.64 | 264.00 | 229954.32 | 403606.35 | 37.11 |
| | SD | 0.00 | 1207.67 | 397.40 | 0.00 | 121667.16 | 242078.84 | 22.03 |
| 50 | Mean | 42.00 | 1831.76 | 202.87 | 264.00 | 239645.55 | 264117.59 | 12.42 |
| | SD | 12.00 | 1275.11 | 45.86 | 0.00 | 213187.43 | 213725.57 | 7.76 |
| 100 | Mean | 36.00 | 2362.16 | 908.42 | 264.00 | 310972.08 | 618552.56 | 42.52 |
| | SD | 13.86 | 1028.21 | 551.98 | 0.00 | 124168.97 | 432041.94 | 22.67 |
| 250 | Mean | 48.00 | 3037.33 | 1248.04 | 234.00 | 394319.12 | 933890.81 | 47.65 |
| | SD | 19.60 | 1339.84 | 370.71 | 60.00 | 152694.36 | 277204.49 | 34.07 |
| 500 | Mean | 60.00 | 4738.03 | 1220.06 | 264.00 | 627108.21 | 839263.68 | 23.01 |
| | SD | 13.86 | 1511.00 | 593.52 | 0.00 | 170509.27 | 305544.82 | 8.87 |

Non-Irradiated Monkeys IL-18 Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6002 | 24.00 | 133.17 | 123.67 | 72.00 | 7429.27 | NC | NC |
| | 6502 | 48.00 | 181.37 | 124.15 | 120.00 | 19078.48 | 35266.53 | 45.90 |
| | Mean | 36.00 | 157.27 | 123.91 | 96.00 | 13253.87 | 35266.53 | 45.90 |

Irradiated Monkeys IL-18 Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6001 | 48.00 | 2483.13 | 1252.97 | 264.00 | 335863.66 | 688686.37 | 51.23 |
| | 6501 | 48.00 | 4242.45 | 3503.23 | 264.00 | 717144.14 | NC | NC |
| | Mean | 48.00 | 3362.79 | 2378.10 | 264.00 | 526503.90 | 688686.37 | 51.23 |

Pharmacodynamics IL-15:
Non-Irradiated Monkeys IL-15 Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | NR | NR | NR | NR | NR | NR | NR |
| 50 | Mean | NR | NR | NR | NR | NR | NR | NR |
| 100 | Mean | 72.00 | 19.76 | 16.69 | 88.00 | 842.68 | NR | NR |
|  | SD | 24.00 | 4.90 | 0.87 | 13.86 | 581.70 | NR | NR |
| 250 | Mean | 72.00 | 37.34 | 17.70 | 108.00 | 2130.94 | NR | NR |
|  | SD | NR | NR | NR | NR | NR | NR | NR |
| 500 | Mean | 80.00 | 27.72 | 18.33 | 120.00 | 2071.10 | 6094.78 | 36.74 |
|  | SD | 13.86 | 12.42 | 4.64 | 24.00 | 1647.15 | NR | NR |

Irradiated Monkeys IL-15 Response after HemaMax SC Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 0 | Mean | 192.00 | 40.04 | 38.18 | 264.00 | 9184.74 | NR | NR |
|  | SD | 70.65 | 8.69 | 8.60 | 0.00 | 1953.14 | NR | NR |
| 50 | Mean | 120.00 | 50.50 | 30.26 | 264.00 | 10333.92 | 42184.00 | 65.42 |
|  | SD | 93.98 | 14.81 | 5.35 | 0.00 | 3747.37 | 18686.08 | 27.35 |
| 100 | Mean | 42.00 | 54.10 | 39.19 | 264.00 | 11403.73 | 36915.54 | 68.57 |
|  | SD | 22.98 | 17.17 | 8.50 | 0.00 | 2899.89 | 9074.88 | 1.64 |
| 250 | Mean | 33.00 | 59.57 | 37.85 | 234.00 | 10561.38 | 28598.31 | 60.96 |
|  | SD | 26.61 | 10.55 | 6.38 | 60.00 | 2843.59 | 10851.28 | 9.79 |
| 500 | Mean | 48.00 | 64.20 | 35.37 | 264.00 | 12362.95 | 24299.63 | 47.71 |
|  | SD | 50.91 | 18.45 | 10.40 | 0.00 | 3493.56 | 8333.47 | 7.49 |

Non-Irradiated Monkeys IL-15 Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6002 | NC | NC | NC | NC | NC | NC | NC |
|  | 6502 | NC | NC | NC | NC | NC | NC | NC |
|  | Mean | NR | NR | NR | NR | NR | NR | NR |

Irradiated Monkeys IL-15 Response after HemaMax IV Dosing

| Dose (ng/kg) | | $T_{max}$ (hr) | $C_{max}$ (pg/mL) | $C_{last}$ (pg/mL) | $T_{last}$ (hr) | $AUC_{last}$ (hr * pg/mL) | $AUC_{0-\infty}$ (hr * pg/mL) | AUC Extrap (%) |
|---|---|---|---|---|---|---|---|---|
| 250 IV | 6001 | 24.00 | 47.37 | 23.30 | 264.00 | 987191.70 | 15665.46 | 47.25 |
|  | 6501 | 24.00 | 47.39 | 26.20 | 264.00 | 1130070.73 | 18076.62 | 48.61 |
|  | Mean | 24.00 | 47.38 | 24.75 | 264.00 | 1058631.21 | 16871.04 | 47.93 |

Example 31

Demonstration of Efficacy in Human Subjects

The efficacy of an exemplary recombinant IL-12 treatment was demonstrated in human subjects in a clinical trial.

The hematopoietic syndrome of acute radiation syndrome (HSARS) is an acute illness caused by whole-body or significant partial-body irradiation. HemaMax™ (recombinant human interleukin-12 [rHuIL-12]) was developed as a single dose first line point-of-care radio-mitigation medical countermeasure (MCM) to stimulate multi-lineage hematopoiesis and mitigate the bone marrow damage following lethal radiation exposure in the event of a nuclear weapon detonation, industrial radiological accident, radiotherapy error, or the like. HemaMax has been granted fast track designation by the FDA for review and approval under the Animal Rule with safety determined in humans in parallel to the efficacy studies to mitigate radiation injury in Rhesus monkeys and mice.

The clinical results demonstrated that HemaMax was found to be safe and well tolerated at 2, 5, 10 and 12 ng doses in the First in Human (FIH) dose escalation study. this next phase 1b, single-dose, randomized, double-blind, placebo-controlled study was conducted to further evaluate and confirm the safety, tolerability, pharmacokinetics and pharmacodynamics of HemaMax™ (rHuIL-12) at 12 ng dose in 60 healthy subjects.

Subjects who satisfied the eligibility criteria were randomized on Day 1 to HemaMax or Placebo in a ratio of 4:1. A single 12 ng dose of HemaMax or Placebo was administered subcutaneously on Day 1. The subjects continued as inpatients through Day 16. They returned to the clinic for two outpatient visits on Days 28 and 45. The criteria for adverse events grading was based on the clinical significance and the fda toxicity grading scale for healthy adult and adolescent volunteers enrolled in preventive vaccine clinical trials. The Safety data was monitored throughout the study by the Safety Review Committee (SRC).

Primary end point was the safety and tolerability based on the number and percentage of subjects reporting adverse events. the criteria for adverse events grading was be based on the clinical significance and the FDA toxicity grading scale for healthy adult and adolescent volunteers enrolled in preventive vaccine clinical trials. the safety data was monitored throughout the study by the safety review committee (SRC).

Secondary end points evaluated pharmacokinetic (PK) and pharmacodynamics (PD) profiles and immunogenicity of HemaMax at 12 µg dose using validated bioanalytical methods. Exploratory end points included evaluation of biological response parameters relevant to stimulatory properties of HemaMax for multi-lineage hematopoiesis.

The study met its primary and secondary end points. No deaths, serious adverse events (SAEs), or withdrawals due to adverse events (AEs) were reported. There were no clinically significant abnormalities in vital signs, ECGs and laboratory safety tests. Transient decreases were seen in neutrophil, platelet and lymphocyte counts.

PK parameters were reproducible compared to FIH study. Mean Cmax and $AUC_{last}$ were 57±50 pg/mL and 1034±631 hr*pg/mL respectively with a Mean $T_{1/2}$ of 117±22 hr. PD profile indicated a robust response for IFN-γ after 12 µg HemaMax dose.

None of the subjects developed anti-HemaMax antibodies.

Among the biological response parameters, induction of IP-10, a chemotactic cytokine, was found to be promising after 12 µg HemaMax dose.

In conclusion, HemaMax was found to be safe and well tolerated in healthy subjects at single subcutaneous dose of 12 µg.

While this invention has been disclosed with reference to specific embodiments, it is apparent that other embodiments and variations of this invention can be devised by those skilled in the art without departing from the true spirit and scope of the invention. The appended claims include all such embodiments and equivalent variations.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

1. Drouet M, Herodin F (2010) Radiation victim management and the haematologist in the future: time to revisit therapeutic guidelines? Int J Radiat Biol 86: 636-648.

2. Donnelly E H, Nemhauser J B, Smith J M, Kazzi Z N, Farfan E B, et al. (2010) Acute radiation syndrome: assessment and management. South Med J 103: 541-546.
3. www.atomicarchive.com. Effects of radiation levels on human body. http://www.atomicarchive.com/Effects/radeffectstable.shtml. Accessed Jun. 19, 2011.
4. Williams J P, Brown S L, Georges G E, Hauer-Jensen M, Hill R P, et al. (2010) Animal models for medical countermeasures to radiation exposure. Radiat Res 173: 557-578.
5. Johnson S M, Torrice C D, Bell J F, Monahan K B, Jiang Q, et al (2010). Mitigation of hematologic radiation toxicity in mice through pharmacological quiescence induced by CDK4/6 inhibition. J Clin Invest. 120:2528-36.
6. Burdelya L G, Krivokrysenko V I, Tallant T C, Strom E, Gleiberman A S, et al. (2008). An agonist of toll-like receptor 5 has radioprotective activity in mouse and primate models. Science 320:226-30.
7. Vijay-Kumar M, Aitken J D, Sanders C J, Frias A, Sloane V M, et al. (2008). Flagellin treatment protects against chemicals, bacteria, viruses, and radiation. J Immunol. 180:8280-5.
8. Chen B J, Deoliveira D, Spasojevic I, Sempowski G D, Jiang C, et al. (2010). Growth hormone mitigates against lethal irradiation and enhances hematologic and immune recovery in mice and nonhuman primates. PLoS One. 5:e11056.
9. Singh V K, Yadav V S. (2005). Role of cytokines and growth factors in radioprotection. Exp Mol Pathol. 78:156-69.
10. Hérodin F, Drouet M. (2005). Cytokine-based treatment of accidentally irradiated victims and new approaches. Exp Hematol. 33:1071-80.
11. Weiss J F, Landauer M R. (2009). History and development of radiation-protective agents. Int J Radiat Biol. 85:539-73.
12. Dumont F, Le Roux A, Bischoff P. (2010). Radiation countermeasure agents: an update. Expert Opin Ther Pat. 20:73-101.
13. Basile L A, Gallaher T K, Shibata D, Miller J D, Douer D (2008) Multilineage hematopoietic recovery with concomitant antitumor effects using low dose Interleukin-12 in myelosuppressed tumor-bearing mice. J Transl Med 6: 26.
14. Chen T, Burke K A, Zhan Y, Wang X, Shibata D, et al. (2007) IL-12 facilitates both the recovery of endogenous hematopoiesis and the engraftment of stem cells after ionizing radiation. Exp Hematol 35: 203-213.
15. Colombo M P, Trinchieri G (2002) Interleukin-12 in anti-tumor immunity and immunotherapy. Cytokine Growth Factor Rev 13: 155-168.
16. Jacobsen S E, Veiby O P, Smeland E B (1993) Cytotoxic lymphocyte maturation factor (interleukin 12) is a synergistic growth factor for hematopoietic stem cells. J Exp Med 178: 413-418.
17. Bellone G, Trinchieri G (1994) Dual stimulatory and inhibitory effect of NK cell stimulatory factor/IL-12 on human hematopoiesis. J Immunol 153: 930-937.
18. Ploemacher R E, van Soest P L, Boudewijn A, Neben S (1993) Interleukin-12 enhances interleukin-3 dependent multilineage hematopoietic colony formation stimulated by interleukin-11 or steel factor. Leukemia 7: 1374-1380.
19. Ploemacher R E, van Soest P L, Voorwinden H, Boudewijn A (1993) Interleukin-12 synergizes with interleukin-3 and steel factor to enhance recovery of murine hemopoietic stem cells in liquid culture. Leukemia 7: 1381-1388.
20. Hirayama F, Katayama N, Neben S, Donaldson D, Nickbarg E B, et al. (1994) Synergistic interaction between interleukin-12 and steel factor in support of proliferation of murine lymphohematopoietic progenitors in culture. Blood 83: 92-98.
21. Broxmeyer H E, Lu L, Platzer E, Feit C, Juliano L, et al. (1983) Comparative analysis of the influences of human gamma, alpha and beta interferons on human multipotential (CFU-GEMM), erythroid (BFU-E) and granulocyte-macrophage (CFU-GM) progenitor cells. J Immunol 131: 1300-1305.
22. Gimble J M, Medina K, Hudson J, Robinson M, Kincade P W (1993) Modulation of lymphohematopoiesis in long-term cultures by gamma interferon: direct and indirect action on lymphoid and stromal cells. Exp Hematol 21: 224-230.
23. Means R T, Jr., Krantz S B (1991) Inhibition of human erythroid colony-forming units by gamma interferon can be corrected by recombinant human erythropoietin. Blood 78: 2564-2567.
24. Terrell T G, Green J D (1993) Comparative pathology of recombinant murine interferon-gamma in mice and recombinant human interferon-gamma in cynomolgus monkeys. Int Rev Exp Pathol 34 Pt B: 73-101.
25. Zoumbos N C, Djeu J Y, Young N S (1984) Interferon is the suppressor of hematopoiesis generated by stimulated lymphocytes in vitro. J Immunol 133: 769-774.
26. Kurz K, Gluhcheva Y, Zvetkova E, Konwalinka G, Fuchs D (2010) Interferon-gamma-mediated pathways are induced in human CD34(+) haematopoietic stem cells. Immunobiology 215: 452-457.
27. Zhao X, Ren G, Liang L, Ai P Z, Zheng B, et al. (2010) Brief report: interferon-gamma induces expansion of Lin (−)Sca-1(+)C-Kit(+) Cells. Stem Cells 28: 122-126.
28. U.S. Food and Drug Administration. Center for Drug Evaluation and Research. (2005) FDA guidance estimating the maximum safe starting dose in initial clinical trials for therapeutics in adult healthy volunteers. http://www.fda.gov/downloads/Drugs/GuidanceComplianceRegulatoryInformation/Guidances/ucm078932.pdf. Accessed Jun. 13, 2011.
29. Yuan R, Maeda Y, Li W, Lu W, Cook S, et al. (2008) Erythropoietin: a potent inducer of peripheral immuno/inflammatory modulation in autoimmune EAE. PLoS One 3: e1924.
30. Barker N, van Es J H, Kuipers J, Kujala P, van den Born M, et al. (2007) Identification of stem cells in small intestine and colon by marker gene Lgr5. Nature 449: 1003-1007.
31. Barker N, Huch M, Kujala P, van de Wetering M, Snippert H J, et al. (2010) Lgr5(+ve) stem cells drive self-renewal in the stomach and build long-lived gastric units in vitro. Cell Stem Cell 6: 25-36.
32. Garcia M I, Ghiani M, Lefort A, Libert F, Strollo S, et al. (2009) LGR5 deficiency deregulates Wnt signaling and leads to precocious Paneth cell differentiation in the fetal intestine. Dev Biol 331: 58-67.
33. Zou J J, Schoenhaut D S, Carvajal D M, Warrier R R, Presky D H, et al. (1995) Structure-function analysis of the p35 subunit of mouse interleukin 12. J Biol Chem 270: 5864-5871.
34. Bekaii-Saab T S, Roda J M, Guenterberg K D, Ramaswamy B, Young D C, et al. (2009) A phase I trial of paclitaxel and trastuzumab in combination with interleukin-12 in patients with HER2/neu-expressing malignancies. Mol Cancer Ther 8: 2983-2991.
35. Lenzi R, Edwards R, June C, Seiden M V, Garcia M E, et al. (2007) Phase II study of intraperitoneal recombinant interleukin-12 (rhIL-12) in patients with peritoneal carcinomatosis (residual disease <1 cm) associated with ovarian cancer or primary peritoneal carcinoma. J Transl Med 5: 66.
36. Little R F, Aleman K, Kumar P, Wyvill K M, Pluda J M, et al. (2007) Phase 2 study of pegylated liposomal doxorubicin in combination with interleukin-12 for AIDS-related Kaposi sarcoma. Blood 110: 4165-4171.
37. Melichar B, Lenzi R, Rosenblum M, Kudelka A P, Kavanagh J J, et al. (2003) Intraperitoneal fluid neopterin, nitrate, and tryptophan after regional administration of interleukin-12. J Immunother 26: 270-276.
38. Neta R, Stiefel S M, Finkelman F, Herrmann S, Ali N (1994) IL-12 protects bone marrow from and sensitizes intestinal tract to ionizing radiation. J Immunol 153: 4230-4237.
39. Trinchieri G (1998) Interleukin-12: a cytokine at the interface of inflammation and immunity. Adv Immunol 70: 83-243.
40. Langrish C L, McKenzie B S, Wilson N J, de Waal M R, Kastelein R A, et al. (2004) IL-12 and IL-23: master regulators of innate and adaptive immunity. Immunol Rev 202: 96-105.
41. Gattoni A, Parlato A, Vangieri B, Bresciani M, Derna R (2006) Interferon-gamma: biologic functions and HCV therapy (type I/II) (1 of 2 parts). Clin Ter 157: 377-386.
42. Macdougall I C, Cooper A C (2002) Erythropoietin resistance: the role of inflammation and pro-inflammatory cytokines. Nephrol Dial Transplant 17 Suppl 11: 39-43.
43. Morceau F, Dicato M, Diederich M (2009) Pro-inflammatory cytokine-mediated anemia: regarding molecular mechanisms of erythropoiesis. Mediators Inflamm 2009: 405016.
44. Dinarello C A, Fantuzzi G (2003) Interleukin-18 and host defense against infection. Infect Dis 187 Suppl 2: S370-S384.
45. Gracie J A, Robertson S E, McInnes I B (2003) Interleukin-18. J Leukoc Biol 73: 213-224.
46. Stonier S W, Schluns K S (2010) Trans-presentation: a novel mechanism regulating IL-15 delivery and responses. Immunol Lett 127: 85-92.
47. Nakanishi K, Yoshimoto T, Tsutsui H, Okamura H (2001) Interleukin-18 is a unique cytokine that stimulates both Th1 and Th2 responses depending on its cytokine milieu. Cytokine Growth Factor Rev 12: 53-72.
48. Werner E R, Werner-Felmayer G, Fuchs D, Hausen A, Reibnegger G, et al. (1990) Tetrahydrobiopterin biosynthetic activities in human macrophages, fibroblasts, THP-1, and T 24 cells. GTP-cyclohydrolase I is stimulated by interferon-gamma, and 6-pyruvoyl tetrahydropterin synthase and sepiapterin reductase are constitutively present. J Biol Chem 265: 3189-3192.
49. Fuchs D, Hausen A, Reibnegger G, Werner E R, Dierich M P, et al. (1988) Neopterin as a marker for activated cell-mediated immunity: application in HIV infection Immunol Today 9: 150-155.
50. Anagnostou A, Liu Z, Steiner M, Chin K, Lee E S, et al. (1994) Erythropoietin receptor mRNA expression in human endothelial cells. Proc Natl Acad Sci USA 91: 3974-3978.
51. Brines M, Cerami A (2005) Emerging biological roles for erythropoietin in the nervous system. Nat Rev Neurosci 6: 484-494.
52. Buemi M, Cavallaro E, Floccari F, Sturiale A, Aloisi C, et al. (2003) The pleiotropic effects of erythropoietin in the central nervous system. J Neuropathol Exp Neurol 62: 228-236.
53. Fraser J K, Tan A S, Lin F K, Berridge M V (1989) Expression of specific high-affinity binding sites for erythropoietin on rat and mouse megakaryocytes. Exp Hematol 17: 10-16.
54. Jaquet K, Krause K, Tawakol-Khodai M, Geidel S, Kuck K H (2002) Erythropoietin and VEGF exhibit equal angiogenic potential. Microvasc Res 64: 326-333.
55. Sela S, Shurtz-Swirski R, Sharon R, Manaster J, Chezar J, et al. (2001) The polymorphonuclear leukocyte—a new target for erythropoietin. Nephron 88: 205-210.
56. Lifshitz L, Prutchi-Sagiv S, Avneon M, Gassmann M, Mittelman M, et al. (2009) Non-erythroid activities of erythropoietin: Functional effects on murine dendritic cells. Mol Immunol 46: 713-721.
57. Prutchi S S, Lifshitz L, Orkin R, Mittelman M, Neumann D (2008) Erythropoietin effects on dendritic cells: potential mediators in its function as an immunomodulator? Exp Hematol 36: 1682-1690.
58. Cetin H, Olgar S, Oktem F, Ciris M, Uz E, et al. (2007) Novel evidence suggesting an anti-oxidant property for erythropoietin on vancomycin-induced nephrotoxicity in a rat model. Clin Exp Pharmacol Physiol 34: 1181-1185.
59. Genc S, Akhisaroglu M, Kuralay F, Genc K (2002) Erythropoietin restores glutathione peroxidase activity in 1-methyl-4-phenyl-1,2,5,6-tetrahydropyridine-induced neurotoxicity in C57BL mice and stimulates murine astroglial glutathione peroxidase production in vitro. Neurosci Lett 321: 73-76.
60. Kumral A, Gonenc S, Acikgoz O, Sonmez A, Genc K, et al. (2005) Erythropoietin increases glutathione peroxidase enzyme activity and decreases lipid peroxidation levels in hypoxic-ischemic brain injury in neonatal rats. Biol Neonate 87: 15-18.
61. Liu J, Narasimhan P, Song Y S, Nishi T, Yu F, et al. (2006) Epo protects SOD2-deficient mouse astrocytes from damage by oxidative stress. Glia 53: 360-365.
62. Wang Z Y, Shen U, Tu L, Hu D N, Liu G Y, et al. (2009) Erythropoietin protects retinal pigment epithelial cells from oxidative damage. Free Radic Biol Med 46: 1032-1041.
63. Akimoto T, Kusano E, Inaba T, Iimura O, Takahashi H, et al. (2000) Erythropoietin regulates vascular smooth muscle cell apoptosis by a phosphatidylinositol 3 kinase-dependent pathway. Kidney Int 58: 269-282.
64. Chong Z Z, Kang J Q, Maiese K (2002) Erythropoietin is a novel vascular protectant through activation of Akt1 and mitochondrial modulation of cysteine proteases. Circulation 106: 2973-2979.
65. Chong Z Z, Kang J Q, Maiese K (2002) Hematopoietic factor erythropoietin fosters neuroprotection through novel signal transduction cascades. J Cereb Blood Flow Metab 22: 503-514.
66. Parsa C J, Matsumoto A, Kim J, Riel R U, Pascal L S, et al. (2003) A novel protective effect of erythropoietin in the infarcted heart. J Clin Invest 112: 999-1007.
67. Gerosa F, Baldani-Guerra B, Nisii C, Marchesini V, Carra G, et al. (2002) Reciprocal activating interaction between natural killer cells and dendritic cells. J Exp Med 195: 327-333.
68. Lodoen M B, Lanier L L (2006) Natural killer cells as an initial defense against pathogens. Curr Opin Immunol 18: 391-398.

69. Varma T K, Lin C Y, Toliver-Kinsky T E, Sherwood E R (2002) Endotoxin-induced gamma interferon production: contributing cell types and key regulatory factors. Clin Diagn Lab Immunol 9: 530-543.
70. de Barros A P, Takiya C M, Garzoni L R, Leal-Ferreira M L, Dutra H S, et al. (2010) Osteoblasts and bone marrow mesenchymal stromal cells control hematopoietic stem cell migration and proliferation in 3D in vitro model. PLoS One 5: e9093.
71. Ahmed N, Khokher M A, Hassan H T (1999) Cytokine-induced expansion of human CD34+ stem/progenitor and CD34+ CD41+ early megakaryocytic marrow cells cultured on normal osteoblasts. Stem Cells 17: 92-99.
72. Hamada T, Mohle R, Hesselgesser J, Hoxie J, Nachman R L, et al. (1998) Transendothelial migration of megakaryocytes in response to stromal cell-derived factor 1 (SDF-1) enhances platelet formation. J Exp Med 188: 539-548.
73. Hodohara K, Fujii N, Yamamoto N, Kaushansky K (2000) Stromal cell-derived factor-1 (SDF-1) acts together with thrombopoietin to enhance the development of megakaryocytic progenitor cells (CFU-MK). Blood 95: 769-775.
74. Kiel M J, Morrison S J (2006) Maintaining hematopoietic stem cells in the vascular niche. Immunity 25: 862-864.
75. Wang J F, Liu Z Y, Groopman J E (1998) The alpha-chemokine receptor CXCR4 is expressed on the megakaryocytic lineage from progenitor to platelets and modulates migration and adhesion. Blood 92: 756-764.
76. Dominici M, Rasini V, Bussolari R, Chen X, Hofmann T J, et al. (2009) Restoration and reversible expansion of the osteoblastic hematopoietic stem cell niche after marrow radioablation. Blood 114: 2333-2343.
77. Savino R, Ciliberto G (2004) A paradigm shift for erythropoietin: no longer a specialized growth factor, but rather an all-purpose tissue-protective agent. Cell Death Differ 11 Suppl 1: S2-S4.
78. Zhang S, Wang Q (2008) Factors determining the formation and release of bioactive IL-12: regulatory mechanisms for IL-12p70 synthesis and inhibition. Biochem Biophys Res Commun 372: 509-512.
79. Lacy M Q, Jacobus S, Blood E A, Kay N E, Rajkumar S V, et al. (2009) Phase II study of interleukin-12 for treatment of plateau phase multiple myeloma (E1A96): a trial of the Eastern Cooperative Oncology Group. Leuk Res 33: 1485-1489.
80. Lenzi R, Rosenblum M, Verschraegen C, Kudelka A P, Kavanagh J J, et al. (2002) Phase I study of intraperitoneal recombinant human interleukin 12 in patients with Mullerian carcinoma, gastrointestinal primary malignancies, and mesothelioma. Clin Cancer Res 8: 3686-3695.
81. Leonard J P, Sherman M L, Fisher G L, Buchanan U, Larsen G, et al. (1997) Effects of single-dose interleukin-12 exposure on interleukin-12-associated toxicity and interferon-gamma production. Blood 90: 2541-2548.
82. Chao N J (2007) Accidental or intentional exposure to ionizing radiation: biodosimetry and treatment options. Exp Hematol 35: 24-27.
83. Kerkar S P, Restifo N P. The power and pitfalls of IL-12. Blood. 2012; 119(18):4096-7.
84. Mann B S, Johnson J R, He K, Sridhara R, Abraham S, Booth B P, Verbois L, Morse D E, Jee J M, Pope S, Harapanhalli R S, Dagher R, Farrell A, Justice R, Pazdur R. Vorinostat for treatment of cutaneous manifestations of advanced primary cutaneous T-cell lymphoma. Clin Cancer Res. 2007; 13(8): 2318-22.
85. Bradford P T, Devesa S S, Anderson W F, Toro J R. Cutaneous lymphoma incidence patterns in the United States: a population-based study of 3884 cases. Blood. 2009; 113(21):5064-73.
86. American Cancer Society. Cancer Facts & Figures 2012. Atlanta: American Cancer Society; 2012.
87. Imam, M H, Shenoy, P J, Flowers, C R, Phillips, A & Lechowicz, M J. Incidence and Survival Patterns of Cutaneous T-cell lymphomas in the United States. Leuk Lymphoma 2012; Sep. 24 [Epub ahead of print].
88. Criscione, V. D. & Weinstock, M. A. Incidence of cutaneous T-cell lymphoma in the United States, 1973-2002. Arch Dermatol 2007; 143, 854-859.
89. Olsen E, Vonderheid E, Pimpinelli N, Willemze R, Kim Y, Knobler R, Zackheim H, Duvic M, Estrach T, Lamberg S, Wood G, Dummer R, Ranki A, Burg G, Heald P, Pittelkow M, Bernengo M G, Sterry W, Laroche L, Trautinger F, Whittaker S; ISCL/EORTC. Revisions to the staging and classification of mycosis fungoides and Sezary syndrome: a proposal of the International Society for Cutaneous Lymphomas (ISCL) and the cutaneous lymphoma task force of the European Organization of Research and Treatment of Cancer (EORTC). Blood 2007; 110: 1713-1722.
90. Gardner J M, Evans K G, Musiek A, Rook A H, Kim E J. Update on treatment of cutaneous T-cell lymphoma. Curr Opin Oncol. 2009; 21(2):131-7.
91. Weberschock T, Strametz R, Lorenz M, Röllig C, Bunch C, Bauer A, Schmitt J. Interventions for mycosis fungoides. Cochrane Database Syst Rev 2012; 9: CD008946.
92. Paralkar V R, Nasta S D, Morrissey K, Smith J, Vassilev P, Martin M E, Goldstein S C, Loren A, Rook A H, Kim E J, Porter D L. Allogeneic hematopoietic SCT for primary cutaneous T cell lymphomas. Bone Marrow Transplant 2012; 47: 940-945.
93. Delioukina M, Zain J, Palmer J M, Tsai N, Thomas S, Forman S. Reduced-intensity allogeneic hematopoietic cell transplantation using fludarabine-melphalan conditioning for treatment of mature T-cell lymphomas. Bone Marrow Transplant 2012; 47: 65-72.
94. Duvic M, Donato M, Dabaja B, Richmond H, Singh L, Wei W, Acholonu S, Khouri I, Champlin R, Hosing C. Total skin electron beam and non-myeloablative allogeneic hematopoietic stem-cell transplantation in advanced mycosis fungoides and Sezary syndrome. J Clin Oncol 2010; 28: 2365-2372.
95. Schlaak M, Theurich S, Pickenhain J, Skoetz N, Kurschat P, von Bergwelt-Baildon M. Allogeneic stem cell transplantation for advanced primary cutaneous T-cell lymphoma: A systematic review. Crit Rev Oncol Hematol 2012; Jul. 17 [Epub ahead of print].
96. Akilov O E, Grant C, Frye R, Bates S, Piekarz R, Geskin L J. Low-dose electron beam radiation and romidepsin therapy for symptomatic cutaneous T-cell lymphoma lesions. Br J Dermatol 2012; 167: 194-197.
97. Yu J B, Khan A M, Jones G W, Reavely M M, Wilson L D. Patient perspectives regarding the value of total skin electron beam therapy for cutaneous T-cell lymphoma/mycosis fungoides: a pilot study. Am J Clin Oncol. 2009; 32(2):142-4.
98. Kamstrup M R, Lindahl L M, Gniadecki R, Iversen L, Skov L, Petersen P M, Loft A, Specht L. Low-dose total skin electron beam therapy as a debulking agent for cutaneous T-cell lymphoma: an open-label prospective phase II study. Br J Dermatol. 2012; 166(2):399-404.
99. Lindahl L M, Kamstrup M R, Petersen P M, Wirén J, Fenger-Grøn M, Gniadecki R, Iversen L, Specht L. Total skin electron beam therapy for cutaneous T-cell lymphoma: a nationwide cohort study from Denmark. Acta Oncol. 2011; 50(8):1199-205.

100. Hauswald H, Zwicker F, Rochet N, Uhl M, Hensley F, Debus J, Herfarth K, Bischof M. Total skin electron beam therapy as palliative treatment for cutaneous manifestations of advanced, therapy-refractory cutaneous lymphoma and leukemia. Radiat Oncol 2012; 7: 118.

101. Parida D K, Verma K K, Rath G K. Total skin electron irradiation treatment for mycosis fungoides with a new alternate daily treatment schedule to minimize radiation-associated toxicity: a preliminary experience. Clin Exp Dermatol. 2009; 34(5): e37-9.

102. Hinds, G. A., Alhariri, J., Klein, R. Q. & Wilson, L. D. Treatment of Mycosis Fungoides With Total Skin Electron Beam: Response and Relapse by Ethnicity and Sex. Am J Clin Oncol 2012; Jun. 14 [Epub ahead of print].

103. Navi D, Riaz N, Levin Y S, Sullivan N C, Kim Y H, Hoppe R T. The Stanford University experience with conventional-dose, total skin electron-beam therapy in the treatment of generalized patch or plaque (T2) and tumor (T3) mycosis fungoides. Arch Dermatol 2011; 147: 561-567.

104. Harrison C, Young J, Navi D, Riaz N, Lingala B, Kim Y, Hoppe R. Revisiting low-dose total skin electron beam therapy in mycosis fungoides. Int J Radiat Oncol Biol Phys 2011; 81: e651-657.

105. Funk A, Hensley F, Krempien R, Neuhof D, Van Kampen M, Treiber M, Roeder F, Timke C, Herfarth K, Helmbold P, Debus J, Bischof M. Palliative total skin electron beam therapy (TSEBT) for advanced cutaneous T-cell lymphoma. Eur J Dermatol 2008; 18: 308-312.

106. http://www.fda.gov/downloads/EmergencyPreparedness/MedicalCountermeasures/UCM283166.pdf. Under this rule, FDA can rely on the evidence from animal studies to provide substantial evidence of the effectiveness of these products when: (1) There is a reasonably well understood pathophysiological mechanism for the toxicity of the chemical, biological, radiological, or nuclear substance and its amelioration or prevention by the product; (2) The effect is demonstrated in more than one animal species expected to react with a response predictive for humans, unless the effect is demonstrated in a single animal species that represents a sufficiently well characterized animal model (meaning the model has been adequately evaluated for its responsiveness) for predicting the response in humans; (3) The animal study endpoint is clearly related to the desired benefit in humans, which is generally the enhancement of survival or prevention of major morbidity; and (4) The data or information on the pharmacokinetics and pharmacodynamics of the product or other relevant data or information in animals and humans is sufficiently well understood to allow selection of an effective dose in humans, and it is therefore reasonable to expect the effectiveness of the product in animals to be a reliable indicator of its effectiveness in humans.

107. Rook A H, Kuzel T M, Olsen E A Cytokine therapy of cutaneous T-cell lymphoma: interferons, interleukin-12, and interleukin-2. Hematol Oncol Clin North Am. 2003; 17:1435-48.

108. Cocco C, Pistoia V, Airoldi I. New perspectives for melanoma immunotherapy: role of IL-12. Curr Mol Med. 2009; 9: 459-69.

109. Yarchoan R, Pluda J M, Wyvill K M, Aleman K, Rodriguez-Chavez I R, Tosato G, Catanzaro A T, Steinberg S M, Little R F.

110. Treatment of AIDS-related Kaposi's sarcoma with interleukin-12: rationale and preliminary evidence of clinical activity. Crit Rev Immunol. 2007; 27: 401-14.

111. Schwarz T, Schwarz A. DNA repair and cytokine responses. J Investig Dermatol Symp Proc. 2009; 14: 63-6.

112. Zaki M H, Wysocka M, Everetts S E, Wang K S, French L E, Ritz J, Rook A H. Synergistic enhancement of cell-mediated immunity by interleukin-12 plus interleukin-2: basis for therapy of cutaneous T cell lymphoma. J Invest Dermatol 2002; 118: 366-371.

113. Rook A H, Wood G S, Yoo E K, Elenitsas R, Kao D M, Sherman M L, Witmer W K, Rockwell K A, Shane R B, Lessin S R, Vonderheid E. Interleukin-12 therapy of cutaneous T-cell lymphoma induces lesion regression and cytotoxic T-cell responses. Blood 1999; 94:902-908.

114. Duvic M, Sherman M L, Wood G S, Kuzel T M, Olsen E, Foss F, Laliberté R J, Ryan J L, Zonno K, Rook A H. A phase II open-label study of recombinant human interleukin-12 in patients with stage IA, IB, or IIA mycosis fungoides. J Am Acad Dermatol 2006; 55: 807-813.

115. Storkus, W. J. & Falo, L. D., Jr. A 'good death' for tumor immunology. Nat Med 2007; 13: 28-30.

116. Steding, C. E., et al. The role of interleukin-12 on modulating myeloid-derived suppressor cells, increasing overall survival and reducing metastasis. Immunology 2011; 133: 221-238.

117. Curti A, Pandolfi S, Aluigi M, Isidori A, Alessandrini I, Chiodoni C, Testoni N, Colombo M P, Baccarani M, Lemoli R M. Interleukin-12 production by leukemia-derived dendritic cells counteracts the inhibitory effect of leukemic microenvironment on T cells. Exp Hematol 2005; 33: 1521-1530.

118. Komita H, Zhao X, Katakam A K, Kumar P, Kawabe M, Okada H, Braughler J M, Storkus W J. Conditional interleukin-12 gene therapy promotes safe and effective antitumor immunity. Cancer Gene Ther 2009; 16: 883-891.

119. Dagher R, Johnson J, Williams G, Keegan P, Pazdur R. Accelerated approval of oncology products: A decade of experience. JNCI-2004; 96: 1500-1509.

120. Buchholz T A. Radiation therapy for early-stage breast cancer after breast-conserving surgery. N Engl J Med. 2009; 360: 63-70.

121. Matzinger O, Zouhair A, Mirimanoff R O, Ozsahin M. Radiochemotherapy in locally advanced squamous cell carcinomas of the head and neck. Clin Oncol (R Coll Radiol). 2009; 21: 525-31.

122. Videtic G M. Locally advanced non-small cell lung cancer: what is the optimal concurrent chemoradiation regimen?

123. Cleve Clin J Med. 2012; 79: Electronic Suppl 1:eS32-7.

124. For example: E. Senkus-Konefka, J. Jassem. Complications of breast-cancer radiotherapy, Clin Oncol (R Coll Radiol) 2006; 18: 229-235.

125. http://emedicine.medscape.com/article/2139720-overview 126. http://www.lls.org/content/nationalcontent/resource-center/freeeducationmaterials/lymphoma/pdf/cutaneoust cell lymphoma.pdf 127. Delfino C, Grandi V, Pileri A, Rupoli S, Quaglino P, Alterini R, Goteri G, Canafoglia L, Pimpinelli N. Combination treatment in CTCL: the current role of bexarotene.

128. G Ital Dermatol Venereol. 2012; 147: 573-80.

128. G Ital Dermatol Venereol. 2012 December; 147(6):573-80.

129. Zic J A. Photopheresis in the treatment of cutaneous T-cell lymphoma: current status. Curr Opin Oncol. 2012; 24 Suppl 1:S1-10.

130. Lindahl L M, Kamstrup M R, Petersen P M, Wirén J, Fenger-Grøn M, Gniadecki R, Iversen L, Specht L. Total skin electron beam therapy for cutaneous T-cell lymphoma: a nationwide cohort study from Denmark. Acta Oncol. 2011; 50: 1199-205.

131. Kamstrup M R, Specht L, Skovgaard G L, Gniadecki R. A prospective, open-label study of low-dose total skin electron beam therapy in mycosis fungoides. Int J Radiat Oncol Biol Phys. 2008 Jul. 15; 71(4):1204-7.

132. Hauswald H, Zwicker F, Rochet N, Uhl M, Hensley F, Debus J, Herfarth K, Bischof M. Total skin electron beam therapy as palliative treatment for cutaneous manifestations of advanced, therapy-refractory cutaneous lymphoma and leukemia. Radiat Oncol 2012; 7: 118.

133. Parida D K, Verma K K, Rath G K. Total skin electron irradiation treatment for mycosis fungoides with a new alternate daily treatment schedule to minimize radiation-associated toxicity: a preliminary experience. Clin Exp Dermatol. 2009; 34(5):e37-9.

134. Chinn D M, Chow S, Kim Y H, Hoppe R T. Total skin electron beam therapy with or without adjunct topical nitrogen mustard or nitrogen mustard alone as initial treatment of T2 and T3 mycosis fungoides. Int J Radiat Oncol Biol Phys. 1999; 43: 951-8.

135. Kuzel T M, Roenigk H H Jr, Rosen S T. Mycosis fungoides and the Sézary syndrome: a review of pathogenesis, diagnosis, and therapy. J Clin Oncol. 1991; 9:1298-313.

136. Querfeld C, Guitart J, Kuzel T M, Rosen S T. Primary cutaneous lymphomas: a review with current treatment options. Blood Rev. 2003 September; 17(3):131-42.

137. Burg G, Dummer R. Historical perspective on the use of retinoids in cutaneous T-cell lymphoma (CTCL). Clin Lymphoma. 2000; 1 Suppl 1: S41-4

138. Siakantaris M P, Tsirigotis P, Stavroyianni N, Argyropoulos K V, Girkas K, Pappa V, Chondropoulos S, Papadavid E, Sakellari I, Anagnostopoulos A, Antoniou C, Dervenoulas J.

139. Management of cutaneous T-Cell lymphoma patients with extracorporeal photopheresis. The Hellenic experience. Transfus Apher Sci. 2012; 46: 189-93.

140. Duvic M. Systemic monotherapy vs combination therapy for CTCL: rationale and future strategies. Oncology (Williston Park). 2007; 21(2 Suppl 1): 33-40.

141. Rook A H, Yoo E K, Grossman D J, Kao D M, Fox F E, Niu Z. Use of biological response modifiers in the treatment of cutaneous T-cell lymphoma. Curr Opin Oncol. 1998; 10: 170-4.

142. Lech-Maranda E, Robak E, Robak T. Novel systemic drugs for cutaneous T-cell lymphoma. Recent Pat Anticancer Drug Discov. 2011; 6: 70-93.

143. Koukourakis M I. Radiation damage and radioprotectants: new concepts in the era of molecular medicine. Br J Radiol. 2012; 85(1012): 313-30.

144. http://www.fda.gov/regulatoryinformation/legislation/federalfooddrugandcosmeticactfdcact/significantamendmentstothefdcact/orphandrugact/default.htm 145. FDA Center for Drug Evaluation and Research (CDER), Manual of Policies and Procedures; (MAPP) 6020.3, revised Jul. 18, 2007; Center for Biologics Evaluation and Research (CBER); Manual of Standard Operating Procedures and Policies (SOPP) 8405, revised Sep. 20, 2004; and "Oncology Tools: Fast Track, Priority Review and Accelerated Approval," at [http://www.accessdata.fda.gov/scripts/cder/onctools/Accel.cfm].

1. Drouet M, Herodin F (2010) Radiation victim management and the haematologist in the future: time to revisit therapeutic guidelines? Int J Radiat Biol 86: 636-648.

2. Donnelly E H, Nemhauser J B, Smith J M, Kazzi Z N, Farfan E B, et al. (2010) Acute radiation syndrome: assessment and management. South Med J 103: 541-546.

3. www.atomicarchive.com. Effects of radiation levels on human body. http://www.atomicarchive.com/Effects/radeffectstable.shtml. Accessed Jun. 19, 2011.

4. Williams J P, Brown S L, Georges G E, Hauer-Jensen M, Hill R P, et al. (2010) Animal models for medical countermeasures to radiation exposure. Radiat Res 173: 557-578.

5. Johnson S M, Torrice C D, Bell J F, Monahan K B, Jiang Q, et al (2010). Mitigation of hematologic radiation toxicity in mice through pharmacological quiescence induced by CDK4/6 inhibition. J Clin Invest. 120:2528-36.

6. Burdelya L G, Krivokrysenko V I, Tallant T C, Strom E, Gleiberman A S, et al. (2008). An agonist of toll-like receptor 5 has radioprotective activity in mouse and primate models. Science 320:226-30.

7. Vijay-Kumar M, Aitken J D, Sanders C J, Frias A, Sloane V M, et al. (2008). Flagellin treatment protects against chemicals, bacteria, viruses, and radiation. J Immunol. 180:8280-5.

8. Chen B J, Deoliveira D, Spasojevic I, Sempowski G D, Jiang C, et al. (2010). Growth hormone mitigates against lethal irradiation and enhances hematologic and immune recovery in mice and nonhuman primates. PLoS One. 5:e11056.

9. Singh V K, Yadav V S. (2005). Role of cytokines and growth factors in radioprotection. Exp Mol Pathol. 78:156-69.

10. Hérodin F, Drouet M. (2005). Cytokine-based treatment of accidentally irradiated victims and new approaches. Exp Hematol. 33:1071-80.

11. Weiss J F, Landauer M R. (2009). History and development of radiation-protective agents. Int J Radiat Biol. 85:539-73.

12. Dumont F, Le Roux A, Bischoff P. (2010). Radiation countermeasure agents: an update. Expert Opin Ther Pat. 20:73-101.

13. Basile L A, Gallaher T K, Shibata D, Miller J D, Douer D (2008) Multilineage hematopoietic recovery with concomitant antitumor effects using low dose Interleukin-12 in myelosuppressed tumor-bearing mice. J Transl Med 6: 26.

14. Chen T, Burke K A, Zhan Y, Wang X, Shibata D, et al. (2007) IL-12 facilitates both the recovery of endogenous hematopoiesis and the engraftment of stem cells after ionizing radiation. Exp Hematol 35: 203-213.

15. Colombo M P, Trinchieri G (2002) Interleukin-12 in anti-tumor immunity and immunotherapy. Cytokine Growth Factor Rev 13: 155-168.

16. Jacobsen S E, Veiby O P, Smeland E B (1993) Cytotoxic lymphocyte maturation factor (interleukin 12) is a synergistic growth factor for hematopoietic stem cells. J Exp Med 178: 413-418.

17. Bellone G, Trinchieri G (1994) Dual stimulatory and inhibitory effect of NK cell stimulatory factor/IL-12 on human hematopoiesis. J Immunol 153: 930-937.

18. Ploemacher R E, van Soest P L, Boudewijn A, Neben S (1993) Interleukin-12 enhances interleukin-3 dependent multilineage hematopoietic colony formation stimulated by interleukin-11 or steel factor. Leukemia 7: 1374-1380.
19. Ploemacher R E, van Soest P L, Voorwinden H, Boudewijn A (1993) Interleukin-12 synergizes with interleukin-3 and steel factor to enhance recovery of murine hemopoietic stem cells in liquid culture. Leukemia 7: 1381-1388.
20. Hirayama F, Katayama N, Neben S, Donaldson D, Nickbarg E B, et al. (1994) Synergistic interaction between interleukin-12 and steel factor in support of proliferation of murine lymphohematopoietic progenitors in culture. Blood 83: 92-98.
21. Broxmeyer H E, Lu L, Platzer E, Feit C, Juliano L, et al. (1983) Comparative analysis of the influences of human gamma, alpha and beta interferons on human multipotential (CFU-GEMM), erythroid (BFU-E) and granulocyte-macrophage (CFU-GM) progenitor cells. J Immunol 131: 1300-1305.
22. Gimble J M, Medina K, Hudson J, Robinson M, Kincade P W (1993) Modulation of lymphohematopoiesis in long-term cultures by gamma interferon: direct and indirect action on lymphoid and stromal cells. Exp Hematol 21: 224-230.
23. Means R T, Jr., Krantz S B (1991) Inhibition of human erythroid colony-forming units by gamma interferon can be corrected by recombinant human erythropoietin. Blood 78: 2564-2567.
24. Terrell T G, Green J D (1993) Comparative pathology of recombinant murine interferon-gamma in mice and recombinant human interferon-gamma in cynomolgus monkeys. Int Rev Exp Pathol 34 Pt B: 73-101.
25. Zoumbos N C, Djeu J Y, Young N S (1984) Interferon is the suppressor of hematopoiesis generated by stimulated lymphocytes in vitro. J Immunol 133: 769-774.
26. Kurz K, Gluhcheva Y, Zvetkova E, Konwalinka G, Fuchs D (2010) Interferon-gamma-mediated pathways are induced in human CD34(+) haematopoietic stem cells. Immunobiology 215: 452-457.
27. Zhao X, Ren G, Liang L, Ai P Z, Zheng B, et al. (2010) Brief report: interferon-gamma induces expansion of Lin (−)Sca-1(+)C-Kit(+) Cells. Stem Cells 28: 122-126.
28. U.S. Food and Drug Administration. Center for Drug Evaluation and Research. (2005) FDA guidance estimating the maximum safe starting dose in initial clinical trials for therapeutics in adult healthy volunteers. http://www.fda.gov/downloads/Drugs/GuidanceComplianceRegulatoryInformation/Guidances/ucm078932.pdf. Accessed Jun. 13, 2011.
29. Yuan R, Maeda Y, Li W, Lu W, Cook S, et al. (2008) Erythropoietin: a potent inducer of peripheral immuno/inflammatory modulation in autoimmune EAE. PLoS One 3: e1924.
30. Barker N, van Es J H, Kuipers J, Kujala P, van den Born M, et al. (2007) Identification of stem cells in small intestine and colon by marker gene Lgr5. Nature 449: 1003-1007.
31. Barker N, Huch M, Kujala P, van de Wetering M, Snippert H J, et al. (2010) Lgr5(+ve) stem cells drive self-renewal and build long-lived gastric units in vitro. Cell Stem Cell 6: 25-36.
32. Garcia M I, Ghiani M, Lefort A, Libert F, Strollo S, et al. (2009) LGR5 deficiency deregulates Wnt signaling and leads to precocious Paneth cell differentiation in the fetal intestine. Dev Biol 331: 58-67.
33. Zou J J, Schoenhaut D S, Carvajal D M, Warrier R R, Presky D H, et al. (1995) Structure-function analysis of the p35 subunit of mouse interleukin 12. J Biol Chem 270: 5864-5871.
34. Bekaii-Saab T S, Roda J M, Guenterberg K D, Ramaswamy B, Young D C, et al. (2009) A phase I trial of paclitaxel and trastuzumab in combination with interleukin-12 in patients with HER2/neu-expressing malignancies. Mol Cancer Ther 8: 2983-2991.
35. Lenzi R, Edwards R, June C, Seiden M V, Garcia M E, et al. (2007) Phase II study of intraperitoneal recombinant interleukin-12 (rhIL-12) in patients with peritoneal carcinomatosis (residual disease <1 cm) associated with ovarian cancer or primary peritoneal carcinoma. J Transl Med 5: 66.
36. Little R F, Aleman K, Kumar P, Wyvill K M, Pluda J M, et al. (2007) Phase 2 study of pegylated liposomal doxorubicin in combination with interleukin-12 for AIDS-related Kaposi sarcoma. Blood 110: 4165-4171.
37. Melichar B, Lenzi R, Rosenblum M, Kudelka A P, Kavanagh J J, et al. (2003) Intraperitoneal fluid neopterin, nitrate, and tryptophan after regional administration of interleukin-12. J Immunother 26: 270-276.
38. Neta R, Stiefel S M, Finkelman F, Herrmann S, Ali N (1994) IL-12 protects bone marrow from and sensitizes intestinal tract to ionizing radiation. J Immunol 153: 4230-4237.
39. Trinchieri G (1998) Interleukin-12: a cytokine at the interface of inflammation and immunity. Adv Immunol 70: 83-243.
40. Langrish C L, McKenzie B S, Wilson N J, de Waal M R, Kastelein R A, et al. (2004) IL-12 and IL-23: master regulators of innate and adaptive immunity. Immunol Rev 202: 96-105.
41. Gattoni A, Parlato A, Vangieri B, Bresciani M, Derna R (2006) Interferon-gamma: biologic functions and HCV therapy (type I/II) (1 of 2 parts). Clin Ter 157: 377-386.
42. Macdougall I C, Cooper A C (2002) Erythropoietin resistance: the role of inflammation and pro-inflammatory cytokines. Nephrol Dial Transplant 17 Suppl 11: 39-43.
43. Morceau F, Dicato M, Diederich M (2009) Pro-inflammatory cytokine-mediated anemia: regarding molecular mechanisms of erythropoiesis. Mediators Inflamm 2009: 405016.
44. Dinarello C A, Fantuzzi G (2003) Interleukin-18 and host defense against infection. J Infect Dis 187 Suppl 2: S370-S384.
45. Gracie J A, Robertson S E, McInnes I B (2003) Interleukin-18. J Leukoc Biol 73: 213-224.
46. Stonier S W, Schluns K S (2010) Trans-presentation: a novel mechanism regulating IL-15 delivery and responses. Immunol Lett 127: 85-92.
47. Nakanishi K, Yoshimoto T, Tsutsui H, Okamura H (2001) Interleukin-18 is a unique cytokine that stimulates both Th1 and Th2 responses depending on its cytokine milieu. Cytokine Growth Factor Rev 12: 53-72.
48. Werner E R, Werner-Felmayer G, Fuchs D, Hausen A, Reibnegger G, et al. (1990) Tetrahydrobiopterin biosynthetic activities in human macrophages, fibroblasts, THP-1, and T 24 cells. GTP-cyclohydrolase I is stimulated by interferon-gamma, and 6-pyruvoyl tetrahydropterin synthase and sepiapterin reductase are constitutively present. J Biol Chem 265: 3189-3192.
49. Fuchs D, Hausen A, Reibnegger G, Werner E R, Dierich M P, et al. (1988) Neopterin as a marker for activated cell-mediated immunity: application in HIV infection. Immunol Today 9: 150-155.

50. Anagnostou A, Liu Z, Steiner M, Chin K, Lee E S, et al. (1994) Erythropoietin receptor mRNA expression in human endothelial cells. Proc Natl Acad Sci USA 91: 3974-3978.
51. Brines M, Cerami A (2005) Emerging biological roles for erythropoietin in the nervous system. Nat Rev Neurosci 6: 484-494.
52. Buemi M, Cavallaro E, Floccari F, Sturiale A, Aloisi C, et al. (2003) The pleiotropic effects of erythropoietin in the central nervous system. J Neuropathol Exp Neurol 62: 228-236.
53. Fraser J K, Tan A S, Lin F K, Berridge M V (1989) Expression of specific high-affinity binding sites for erythropoietin on rat and mouse megakaryocytes. Exp Hematol 17: 10-16.
54. Jaquet K, Krause K, Tawakol-Khodai M, Geidel S, Kuck K H (2002) Erythropoietin and VEGF exhibit equal angiogenic potential. Microvasc Res 64: 326-333.
55. Sela S, Shurtz-Swirski R, Sharon R, Manaster J, Chezar J, et al. (2001) The polymorphonuclear leukocyte—a new target for erythropoietin. Nephron 88: 205-210.
56. Lifshitz L, Prutchi-Sagiv S, Avneon M, Gassmann M, Mittelman M, et al. (2009) Non-erythroid activities of erythropoietin: Functional effects on murine dendritic cells. Mol Immunol 46: 713-721.
57. Prutchi S S, Lifshitz L, Orkin R, Mittelman M, Neumann D (2008) Erythropoietin effects on dendritic cells: potential mediators in its function as an immunomodulator? Exp Hematol 36: 1682-1690.
58. Cetin H, Olgar S, Oktem F, Ciris M, Uz E, et al. (2007) Novel evidence suggesting an anti-oxidant property for erythropoietin on vancomycin-induced nephrotoxicity in a rat model. Clin Exp Pharmacol Physiol 34: 1181-1185.
59. Genc S, Akhisaroglu M, Kuralay F, Genc K (2002) Erythropoietin restores glutathione peroxidase activity in 1-methyl-4-phenyl-1,2,5,6-tetrahydropyridine-induced neurotoxicity in C57BL mice and stimulates murine astroglial glutathione peroxidase production in vitro. Neurosci Lett 321: 73-76.
60. Kumral A, Gonenc S, Acikgoz O, Sonmez A, Genc K, et al. (2005) Erythropoietin increases glutathione peroxidase enzyme activity and decreases lipid peroxidation levels in hypoxic-ischemic brain injury in neonatal rats. Biol Neonate 87: 15-18.
61. Liu J, Narasimhan P, Song Y S, Nishi T, Yu F, et al. (2006) Epo protects SOD2-deficient mouse astrocytes from damage by oxidative stress. Glia 53: 360-365.
62. Wang Z Y, Shen L J, Tu L, Hu D N, Liu G Y, et al. (2009) Erythropoietin protects retinal pigment epithelial cells from oxidative damage. Free Radic Biol Med 46: 1032-1041.
63. Akimoto T, Kusano E, Inaba T, Iimura O, Takahashi H, et al. (2000) Erythropoietin regulates vascular smooth muscle cell apoptosis by a phosphatidylinositol 3 kinase-dependent pathway. Kidney Int 58: 269-282.
64. Chong Z Z, Kang J Q, Maiese K (2002) Erythropoietin is a novel vascular protectant through activation of Akt1 and mitochondrial modulation of cysteine proteases. Circulation 106: 2973-2979.
65. Chong Z Z, Kang J Q, Maiese K (2002) Hematopoietic factor erythropoietin fosters neuroprotection through novel signal transduction cascades. J Cereb Blood Flow Metab 22: 503-514.
66. Parsa C J, Matsumoto A, Kim J, Riel R U, Pascal L S, et al. (2003) A novel protective effect of erythropoietin in the infarcted heart. J Clin Invest 112: 999-1007.
67. Gerosa F, Baldani-Guerra B, Nisii C, Marchesini V, Carra G, et al. (2002) Reciprocal activating interaction between natural killer cells and dendritic cells. J Exp Med 195: 327-333.
68. Lodoen M B, Lanier L L (2006) Natural killer cells as an initial defense against pathogens. Curr Opin Immunol 18: 391-398.
69. Varma T K, Lin C Y, Toliver-Kinsky T E, Sherwood E R (2002) Endotoxin-induced gamma interferon production: contributing cell types and key regulatory factors. Clin Diagn Lab Immunol 9: 530-543.
70. de Barros A P, Takiya C M, Garzoni L R, Leal-Ferreira M L, Dutra H S, et al. (2010) Osteoblasts and bone marrow mesenchymal stromal cells control hematopoietic stem cell migration and proliferation in 3D in vitro model. PLoS One 5: e9093.
71. Ahmed N, Khokher M A, Hassan HT (1999) Cytokine-induced expansion of human CD34+ stem/progenitor and CD34+CD41+ early megakaryocytic marrow cells cultured on normal osteoblasts. Stem Cells 17: 92-99.
72. Hamada T, Mohle R, Hesselgesser J, Hoxie J, Nachman R L, et al. (1998) Transendothelial migration of megakaryocytes in response to stromal cell-derived factor 1 (SDF-1) enhances platelet formation. J Exp Med 188: 539-548.
73. Hodohara K, Fujii N, Yamamoto N, Kaushansky K (2000) Stromal cell-derived factor-1 (SDF-1) acts together with thrombopoietin to enhance the development of megakaryocytic progenitor cells (CFU-MK). Blood 95: 769-775.
74. Kiel M J, Morrison S J (2006) Maintaining hematopoietic stem cells in the vascular niche. Immunity 25: 862-864.
75. Wang J F, Liu Z Y, Groopman J E (1998) The alpha-chemokine receptor CXCR4 is expressed on the megakaryocytic lineage from progenitor to platelets and modulates migration and adhesion. Blood 92: 756-764.
76. Dominici M, Rasini V, Bussolari R, Chen X, Hofmann T J, et al. (2009) Restoration and reversible expansion of the osteoblastic hematopoietic stem cell niche after marrow radioablation. Blood 114: 2333-2343.
77. Savino R, Ciliberto G (2004) A paradigm shift for erythropoietin: no longer a specialized growth factor, but rather an all-purpose tissue-protective agent. Cell Death Differ 11 Suppl 1: S2-S4.
78. Zhang S, Wang Q (2008) Factors determining the formation and release of bioactive IL-12: regulatory mechanisms for IL-12p70 synthesis and inhibition. Biochem Biophys Res Commun 372: 509-512.
79. Lacy M Q, Jacobus S, Blood E A, Kay N E, Rajkumar S V, et al. (2009) Phase II study of interleukin-12 for treatment of plateau phase multiple myeloma (E1A96): a trial of the Eastern Cooperative Oncology Group. Leuk Res 33: 1485-1489.
80. Lenzi R, Rosenblum M, Verschraegen C, Kudelka A P, Kavanagh J J, et al. (2002) Phase I study of intraperitoneal recombinant human interleukin 12 in patients with Mullerian carcinoma, gastrointestinal primary malignancies, and mesothelioma. Clin Cancer Res 8: 3686-3695.
81. Leonard J P, Sherman M L, Fisher G L, Buchanan L J, Larsen G, et al. (1997) Effects of single-dose interleukin-12 exposure on interleukin-12-associated toxicity and interferon-gamma production. Blood 90: 2541-2548.
82. Chao N J (2007) Accidental or intentional exposure to ionizing radiation: biodosimetry and treatment options. Exp Hematol 35: 24-27

What is claimed is:

1. A method of protecting a subject having a cutaneous T-cell lymphoma (CTCL) from system, organ, tissue, or cellular damage, following exposure of the subject to external beam radiation therapy for treatment of CTCL, the method comprising:
administering a therapeutically effective amount of a pharmaceutical composition comprising substantially isolated rIL-12 to the subject, whereby the system, organ, tissue, and/or cellular damage due to radiation is diminished.

2. The method of claim 1, wherein the radiation dose is between about 0.7 Gy and about 50 Gy.

3. The method of claim 1, wherein the effective dose of IL-12 protects more than one system, organ and/or tissue from radiation damage and the two organs protected are the bone marrow and skin.

4. The method of claim 1, wherein the systems, organs or tissues protected are selected from the group consisting of: bone marrow, lymphatic system, immune system, immune tissues, mucosal tissue, mucosal immune system, gastrointestinal system, cardiovascular system, nervous system, reproductive organs, prostate, ovaries, lung, kidney, skin, nails, sweat glands, dermal tissue, and brain.

5. The method of claim 1, wherein:
(a) the effective dose of IL-12 is less than 300 ng/kg;
(b) the effective dose of IL-12 is given in two or more doses of less than 50 ng/kg for each dose;
(c) the one or more effective dose(s) of IL-12 is less than 200 ng/kg;
(d) the one or more effective dose(s) of IL-12 is less than 100 ng/kg;
(e) each dose of IL-12 is between about 1 ng/kg and less than about 2000 ng/kg, and said dose is administered by a delivery route selected from the group consisting of intradermal, intramuscular, intraperitoneal, intravenous, topical, subcutaneous, and epidural routes; or
(f) the effective dose of IL-12 is given in two or more doses of less than 30 ng/kg for each dose.

6. The method of claim 1, wherein:
(a) the one or more effective dose(s) of IL-12 are given before radiation exposure; or
(b) the one or more effective dose(s) of IL-12 are given before and after radiation exposure.

7. The method of claim 1, wherein the one or more effective dose(s) of IL-12 are given:
(a) after radiation exposure;
(b) at greater than 24 hours after radiation exposure;
(c) at greater than 48 hours after radiation exposure;
(d) at greater than 72 hours after radiation exposure;
(e) at greater than 96 hours after radiation exposure; or
(f) at greater than 120 hours after radiation exposure.

8. The method of claim 1, wherein the one or more effective doses of IL-12 are administered subcutaneously, intravenously, intramuscularly, topically, intratumorally or intradermally.

9. The method of claim 1, wherein the IL-12 is administered at or near the site of irradiation.

10. The method of claim 1, wherein the external-beam radiation therapy is selected from the group consisting of intensity-modulated radiation therapy (IMRT), image-guided radiation therapy (IGRT), tomotherapy, stereotactic radiosurgery, stereotactic body radiation therapy, photon beam, electron beam and proton therapy.

11. The method of claim 1, wherein the administered IL-12 induces the production of at least one of erythropoietin, chemokine, cytokine, MCP-1, IFN-g, IL-15, IL-18, IP-10, MG, Mip1 beta, I-TAC, eotaxin, eotaxin-3, TARC, or IL-8.

12. The method of claim 1, wherein the pharmaceutical composition comprises substantially isolated rIL-12 in a pharmaceutically acceptable carrier.

13. The method of claim 1, wherein the CTCL is Mycosis Fungoides and/or Sezary syndrome.

14. The method of claim 13, wherein the external-beam radiation therapy is electron beam therapy.

15. The method of claim 14, wherein the electron beam therapy is local electron beam therapy or total skin electron beam therapy.

16. The method of claim 14, wherein the electron beam therapy is local electron beam therapy or total skin electron beam therapy and the radiation is received as high dose fractions.

17. The method of claim 14, wherein the electron beam therapy is local electron beam therapy or total skin electron beam therapy and the radiation is received as low dose fractions.

18. The method of claim 1, wherein administration of rIL-12 reduces skin damage due to the external-beam radiation therapy.

19. The method of claim 1, wherein administration of rIL-12 increases the anti-tumor response of the external-beam radiation therapy.

20. The method of claim 1, wherein administration of rIL-12 increases the increases the overall survival of the subject compared to external-beam radiation therapy alone.

* * * * *